United States Patent
Bonanomi et al.

(10) Patent No.: US 7,989,444 B2
(45) Date of Patent: Aug. 2, 2011

(54) COMPOUNDS HAVING AFFINITY FOR DOPAMINE D3 RECEPTOR AND USES THEREOF

(75) Inventors: Giorgio Bonanomi, Verona (IT); Federica Damiani, Verona (IT); Gabriella Gentile, Verona (IT); Dieter Wolfgang Hamprecht, Verona (IT); Fabrizio Micheli, Verona (IT); Luca Tarsi, Verona (IT); Giovanna Tedesco, Verona (IT); Silvia Terreni, Verona (IT)

(73) Assignee: Glaxo Group Limited, Greenford, Middlesex (GB)

( * ) Notice: Subject to any disclaimer, the term of this patent is extended or adjusted under 35 U.S.C. 154(b) by 606 days.

(21) Appl. No.: 11/569,880

(22) PCT Filed: May 31, 2005

(86) PCT No.: PCT/EP2005/005965
§ 371 (c)(1),
(2), (4) Date: Sep. 23, 2009

(87) PCT Pub. No.: WO2005/118549
PCT Pub. Date: Dec. 15, 2005

(65) Prior Publication Data
US 2010/0016287 A1    Jan. 21, 2010

(30) Foreign Application Priority Data
Jun. 2, 2004 (GB) .................................. 0412314.7

(51) Int. Cl.
A61P 25/18    (2006.01)
A61K 31/55    (2006.01)
C07D 487/04   (2006.01)
C07D 498/04   (2006.01)
C07D 513/04   (2006.01)

(52) U.S. Cl. ........ 514/215; 540/576; 540/578; 540/580; 540/586

(58) Field of Classification Search ................. 514/215; 540/576, 578, 580, 586
See application file for complete search history.

(56) References Cited

FOREIGN PATENT DOCUMENTS
| DE | 27 51 258 A | 6/1978 |
| WO | WO 94/20472 A | 9/1994 |
| WO | WO 00/42036 A | 7/2000 |
| WO | WO 02/40471 A | 5/2002 |

*Primary Examiner* — Brenda Coleman
(74) *Attorney, Agent, or Firm* — Bonnie L. Deppenbrock

(57) ABSTRACT

Compounds of formula (I)

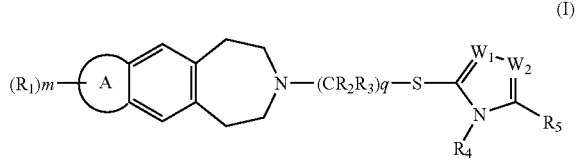

wherein A is a 5 or 6 membered heteroaromatic ring or a 5 or 6 membered heterocyclic ring, and which are useful for treating mental disorders such as schizophrenia are set out herein.

11 Claims, No Drawings

COMPOUNDS HAVING AFFINITY FOR DOPAMINE D3 RECEPTOR AND USES THEREOF

This application claims the benefit of International Application No. PCT/EP2005/005965, filed 15 Mar. 2005, which claims the priority of GB application number 0412314.7 filed 2 Jun. 2004.

The present invention relates to novel compounds, processes for their preparation, intermediates used in these processes, pharmaceutical compositions containing them and their use in therapy, as modulators of dopamine $D_3$ receptors, in particular as antipsychotic agents.

WO 2002/40471 (SmithKline Beecham) discloses certain benzodiazepine compounds having activity at the dopamine $D_3$ receptor.

A new class of compounds which have affinity for dopamine receptors, in particular the dopamine $D_3$ receptor, has been found. These compounds have potential in the treatment of conditions wherein modulation, especially antagonism/inhibition, of the $D_3$ receptor is beneficial, e.g. as antipsychotic agents or to treat drug dependency.

The present invention provides a compound of formula (I) or a salt thereof:

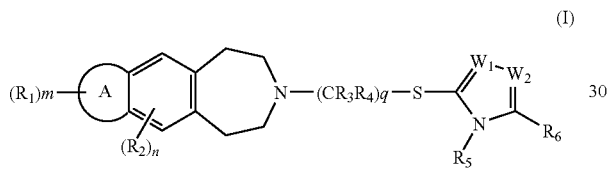

(I)

wherein
A is a 5 or 6 membered heteroaromatic ring or a 5 or 6 membered heterocyclic ring;
m is 0, 1, 2 or 3;
$R_1$ is independently halogen, oxo, hydroxy, cyano, nitro, $C_{1-4}$alkyl, halo$C_{1-4}$alkyl, $C_{3-6}$cycloalkyl, $C_{1-4}$alkoxy, halo$C_{1-4}$alkoxy, $C_{1-4}$alkoxy$C_{1-4}$alkoxy, $C_{1-4}$alkylenedioxy, $C_{1-4}$alkylthio, $C_{1-4}$alkoxy$C_{1-4}$alkyl, $C_{1-4}$cycloalkyl$C_{1-4}$alkoxy, $C_{3-6}$cycloalkyl$C_{1-4}$alkyl, $C_{1-4}$alkanoyl, $C_{1-4}$alkoxycarbonyl, $C_{1-4}$alkoxycarbonyl$C_{1-4}$alkyl, $C_{1-4}$alkylsulfonyl, $C_{1-4}$alkylsulfonyloxy, halo$C_{1-4}$alkylsulfonyl, halo$C_{1-4}$alkylsulfonyloxy, $C_{1-4}$alkylsulfonyl$C_{1-4}$alkyl, $C_{1-4}$alkylsulfonamido, $C_{1-4}$alkylsulfonamido$C_{1-4}$alkyl, heterocyclyl, aryl, aryl$C_{1-4}$alkoxy, aryloxy, arylthio, arylmethyl, aroyl, aryloxymethyl, arylsulfonyl, aryl-NR'— (wherein R is hydrogen or $C_{1-4}$alkyl), arylsulfonyloxy, arylsulfonyl$C_{1-4}$alkyl, arylsulfonamido, arylcarboxamido, arylsulfonamido$C_{1-4}$alkyl, arylcarboxamido$C_{1-4}$alkyl, aroyl$C_{1-4}$alkyl, aryl$C_{1-4}$alkanoyl, a group $NR_7R_8$, $R_7CON(R_8)(CH_2)_r$, $R_7R_8NCO(CH_2)_r$ or $R_7R_8NSO_2(CH_2)_r$ (in which r is 0, 1, 2, 3 or 4, and each of $R_7$ and $R_8$ is independently hydrogen or $C_{1-4}$alkyl, or in the groups $NR_7R_8$, $R_7CON(R_8)(CH_2)_r$, $R_7R_8NCO(CH_2)_r$ and $R_7R_8NSO_2(CH_2)_r$, $R_7CONR_8$ or $NR_7R_8$ together form a 4-, 5-, 6- or 7-membered azacyclic group optionally containing one additional O, N or S atom in the azacycle and having 3-8 carbon atoms (including the carbon atoms contained in any optional substituent(s) of the azacycle)); wherein in any group containing an aryl moiety, the aryl moiety is optionally substituted by one, two or three substituents selected from the group consisting of halogen, hydroxy, cyano, nitro, amino, $C_{1-4}$alkyl, halo$C_{1-4}$alkyl, $C_{1-4}$alkoxy, halo$C_{1-4}$alkoxy, $C_{1-4}$alkylenedioxy, $C_{1-4}$alkanoyl, $C_{1-4}$alkylsulfonyl, halo$C_{1-4}$ alkylsulfonyl, $C_{1-4}$alkylamino, $C_{1-4}$dialkylamino, $R_9R_{10}NCO$ (in which $R_9$ and $R_{10}$ are independently hydrogen or $C_{1-4}$alkyl, or $R_9R_{10}N$ together form a 4-, 5-, 6- or 7-membered azacyclic group optionally containing one additional O, N or S atom in the azacycle and having 3-8 carbon atoms (including the carbon atoms contained in any optional substituent(s) of the azacycle));
n is 0, 1 or 2;
$R_2$ is independently fluoro, chloro, bromo, $C_{1-2}$alkyl, $C_{1-2}$alkoxy, halo$C_{1-2}$alkyl, halo$C_{1-2}$alkoxy, hydroxy, cyano, nitro or a group $NR_{15}R_{16}$ (where $R_{15}$ and $R_{16}$ are independently hydrogen or $C_{1-4}$alkyl, or $R_{15}$ and $R_{16}$, together with the nitrogen atom to which they are attached, form a 4- to 8-membered ring);
$R_3$ and $R_4$ are independently hydrogen or methyl;
q is 2, 3 or 4;
$W_1$ and $W_2$ are independently N, CH or —C($C_{1-4}$alkyl)-;
$R_5$ is hydrogen or $C_{1-4}$alkyl;
$R_6$ is a group of the formula (a) or (b):

—Z (a)

—$(CR_{11}R_{12})_tZ$ (b)

wherein
Z is $C_{1-4}$alkyl, halo$C_{1-4}$alkyl, $C_{3-6}$cycloalkyl, phenyl, heterocyclyl, a 5- or 6-membered heteroaromatic group or a 8- to 11-membered bicyclic group, any of which is optionally substituted by 1, 2, 3 or 4 substituents selected from the group consisting of: halogen, hydroxy, oxo, cyano, nitro, $C_{1-4}$alkyl, $C_{1-4}$alkoxy, halo$C_{1-4}$alkyl, halo$C_{1-4}$alkoxy, $C_{1-4}$alkylenedioxy, $C_{1-4}$alkanoyl, $C_{1-4}$alkylsulfonyl, $C_{1-4}$alkylsulfonyloxy, halo$C_{1-4}$alkylsulfonyl, halo$C_{1-4}$alkylsulfonyloxy, $C_{1-4}$alkylsulfinyl, $C_{1-4}$alkylthio, $R_{13}SO_2NR_{14}$—, $R_{13}R_{14}NSO_2$—, $R_{13}R_{14}N$—, $R_{13}R_{14}NCO$—, $R_{13}CONR_{14}$— and a 5- or 6-membered heteroaromatic group which is optionally substituted by one or two groups selected from $C_{1-2}$alkyl, halo$C_{1-2}$alkyl and $R_{13}R_{14}N$—; and wherein substituents positioned ortho to one another may be linked to form a 5- or 6-membered ring;
$R_{11}$ and $R_{12}$ are independently hydrogen or $C_{1-4}$alkyl and t is 1, 2, 3 or 4, or —$(CR_{11}, R_{12})t$-forms a $C_{3-6}$cycloalkylene linker; and
$R_{13}$ and $R_{14}$ are independently hydrogen or $C_{1-4}$alkyl, or $R_{13}$ and $R_{14}$ together form $C_{3-6}$alkylene.

In formula (I), "—S—" means thio (sulfur).

The term "5- or 6-membered heteroaromatic ring" refers to a monocyclic 5- or 6-membered aromatic heterocyclic ring containing 1, 2, 3 or 4 heteroatoms, for example from 1 to 3 heteroatoms, selected from O, N and S. When the group contains 2-4 heteroatoms, one may be selected from O, N and S and the remaining heteroatoms may be N. Examples of 5 and 6-membered heteroaromatic groups include pyrrolyl, pyrrolinyl, pyrazolinyl, imidazolyl, pyrazolyl, oxazolyl, isoxazolyl, oxadiazolyl, isothiazolyl, thiazolyl, furyl, thienyl, thiadiazolyl, pyridyl, triazolyl, thiazinyl, triazinyl, pyridazinyl, pyrimidinyl and pyrazinyl.

The term "5- or 6-membered heterocyclic ring" refers to a 5 or 6-membered monocyclic ring which is partially or fully saturated, and wherein 1, 2, 3, 4 or 5 of the carbon atoms are replaced by a heteroatom independently selected from O, S and N. Examples of "heterocyclyl" which are fully saturated 5 or 6-membered monocyclic rings include pyrrolidinyl, imidazolidinyl, pyrazolidinyl, tetrahydrofuranyl, dioxolanyl, piperidinyl, piperazinyl, morpholinyl, thiomorpholinyl, tetrahydrothienyl, dioxanyl, tetrahydro-2H-pyranyl and dithianyl. Examples of "heterocyclyl" groups which are partially saturated 5 or 6-membered monocyclic rings include oxazolinyl, isoaxazolinyl, imidazolinyl, pyrazolinyl, 1,2,3,6-tetrahydropyridyl and 3,6-dihydro-2H-pyranyl.

The term "$C_{1-4}$alkyl" refers to an alkyl group having from one to four carbon atoms, in all isomeric forms, such as methyl, ethyl, propyl, isopropyl, butyl, isobutyl, sec-butyl and tert-butyl. "$C_{1-6}$alkyl" includes, in addition to the above, groups such as pentyl and hexyl.

The term "alkylene" refers to a straight or branched chain divalent hydrocarbon radical. Examples of $C_{1-4}$alkylene groups include methylene, ethylene and n-propylene. Examples of "$C_{1-4}$alkylene" include, in addition to the above, n-butylene.

The term "$C_{1-4}$alkoxy" refers to a straight chain or branched chain alkoxy (or "alkyloxy") group having from one to four carbon atoms, such as methoxy, ethoxy, propoxy, isopropoxy, butoxy, isobutoxy, sec-butoxy and tert-butoxy.

The term "halogen" and its abbreviation "halo" refer to fluorine (F), chlorine (Cl), bromine (Br) or iodine (I). Where the term "halo" is used before another group, it indicates that the group is substituted by one, two or three halogen atoms. For example, "halo$C_{1-4}$alkyl" refers to groups such as trifluoromethyl, bromoethyl, trifluoropropyl, and other groups derived from $C_{1-4}$alkyl groups as defined above; and the term "halo$C_{1-4}$alkoxy" refers to groups such as trifluoromethoxy, bromoethoxy, trifluoropropoxy, and other groups derived from $C_{1-4}$alkoxy groups as defined above.

The term "$C_{1-4}$alkoxy$C_{1-4}$alkyl" refers to a $C_{1-4}$alkoxy group attached through a $C_{1-4}$alkylene group, for example methoxymethyl, ethoxymethyl, propoxyethyl, isopropoxyethyl and others derived from the $C_{1-4}$alkoxy and $C_{1-4}$alkyl groups as defined above.

The term "$C_{1-4}$alkylthio" refers to a $C_{1-4}$alkyl group attached through a sulfur atom (—S—). Examples of $C_{1-4}$alkylthio include methylthio, ethylthio, propylthio and butylthio.

The term "$C_{3-6}$cycloalkyl" refers to a cycloalkyl group having from three to six carbon atoms, such as cyclopropyl, cyclobutyl, cyclopentyl and cyclohexyl. The term "$C_{3-6}$cycloalkylene" refers to a divalent cycloalkyl group, such as cyclopropylene, cyclobutylene, cyclopentylene and cyclohexylene.

The term "$C_{3-6}$cycloalkyl$C_{1-4}$alkyl" refers to a cycloalkyl group attached through a $C_{1-4}$alkylene group, such as cyclopropylmethyl, cyclobutylethyl, and others derived from $C_{3-6}$cycloalkyl groups and $C_{1-4}$alkyl groups as defined above.

The term "$C_{3-6}$cycloalkyl$C_{1-4}$alkoxy" refers to a cycloalkyl group attached through a $C_{1-4}$alkoxy group, such as cyclopropylmethyleneoxy, cyclobutylethyleneoxy, and others derived from $C_{1-6}$cycloalkyl groups and $C_{1-4}$alkoxy groups as defined above.

The term "aryl" refers to phenyl or a 5- or 6-membered heteroaromatic group. Examples of 5- or 6-membered heteroaromatic groups include furanyl, thienyl, pyrrolyl, oxazolyl, thiazolyl, imidazolyl, oxadiazolyl, thiadiazolyl, pyridinyl, triazolyl, triazinyl, pyridazyl, pyrimidinyl, isothiazolyl, isoxazolyl, pyrazinyl, pyrazolyl and pyrimidinyl The term "aryl$C_{1-4}$alkyl" refers to an aryl group attached through a $C_{1-4}$alkylene group. The $C_{1-6}$alkylene group may be in any suitable isomeric form. Examples of aryl$C_{1-4}$alkyl include benzyl, phenethyl (including phenyl-$CH_2CH_2$— and phenyl-$C(CH_3)$—) and others derived from the aryl groups and $C_{1-4}$alkyl groups as defined above.

The terms "aryl$C_{1-4}$alkoxy" refers to an aryl group attached through a $C_{1-4}$alkoxy group. Examples of aryl$C_{1-4}$alkoxy include benzyloxy (phenyl-$CH_2O$—) and phenylethoxy.

The term "sulfonyl" refers to the group —$SO_2$—. Thus, the term "$C_{1-4}$alkylsulfonyl" includes methylsulfonyl, ethylsulfonyl, and others derived from the $C_{1-4}$alkyl groups defined above. The term "halo$C_{1-4}$alkylsulfonyl" refers to groups such as trifluoromethanesulfonyl and pentafluoroethylsulfonyl. The term "arylsulfonyl" includes phenylsulfonyl, pyridinylsulfonyl, and others derived from aryls as defined above.

The term "arylcarboxamido" refers to groups such as phenylcarboxamido and pyridinylcarboxamido, and others derived from the aryl groups as defined above.

The term "$C_{1-4}$alkylenedioxy" refers to groups such as methylenedioxy, ethylenedioxy and others derived from $C_{1-4}$alkyl as defined above.

The term "8- to 11-membered bicyclic group" refers to a bicyclic ring system containing a total of 8, 9, 10 or 11 carbon atoms, wherein 1, 2, 3 or 4 or 5 of the carbon atoms are optionally replaced by a heteroatom independently selected from O, S and N. The term includes bicyclic systems wherein both rings are aromatic, as well as bicyclic ring systems wherein one of the rings is partially or fully saturated. Examples of 8- to 11-membered bicyclic groups wherein both rings are aromatic include indenyl, naphthyl and azulenyl. Examples of 8- to 11-membered bicyclic groups having 1, 2, 3, 4 or 5 heteroatoms, in which both rings are aromatic, include: 6H-thieno[2,3-b]pyrrolyl, imidazo[2,1-b][1,3]thiazolyl, imidazo[5,1-b][1,3]thiazolyl, [1,3]thiazolo[3,2-b][1,2,4]triazolyl, indolyl, isoindolyl, indazolyl, benzimidazolyl e.g. benzimidazol-2-yl, benzoxazolyl e.g. benzoxazol-2-yl, benzisoxazolyl, benzothiazolyl, benzisothiazolyl, benzothienyl, benzofuranyl, naphthridinyl, quinolyl, quinoxalinyl, quinazolinyl, cinnolinyl and isoquinolyl. Examples of 8- to 11-membered bicyclic groups having 1, 2, 3, 4 or 5 heteroatoms, in which one of the rings is partially or fully saturated includes dihydrobenzofuranyl, indanyl, tetrahydronaphthyl, indolinyl, isoindolinyl, tetrahydroisoquinolinyl, tetrahydroquinolyl, benzoxazinyl and benzoazepinyl.

The term "8- to 11-membered bicyclic heterocyclic group" refers to a bicyclic ring system containing a total of 8, 9, 10 or 11 carbon atoms, wherein 1, 2, 3, 4 or 5 of the carbon atoms are replaced by a heteroatom independently selected from O, S and N. Examples of 8- to 11-membered bicyclic heterocyclic groups in which both rings are aromatic include: 6H-thieno[2,3-b]pyrrolyl, imidazo[2,1-b][1,3]thiazolyl, imidazo[5,1-b][1,3]thiazolyl, [1,3]thiazolo[3,2-b][1,2,4]triazolyl, indolyl, isoindolyl, indazolyl, benzimidazolyl e.g. benzimidazol-2-yl, benzoxazolyl e.g. benzoxazol-2-yl, benzisoxazolyl, benzothiazolyl, benzisothiazolyl, benzothienyl, benzofuranyl, naphthridinyl, quinolyl, quinoxalinyl, quinazolinyl, cinnolinyl and isoquinolyl. Examples of 8- to 11-membered bicyclic heterocyclic groups, in which one of the rings is partially or fully saturated includes dihydrobenzofuranyl, indanyl, tetrahydronaphthyl, indolinyl, isoindolinyl, tetrahydroisoquinolinyl, tetrahydroquinolyl, benzoxazinyl and benzoazepinyl.

The term "heterocyclyl" refers to a 5 or 6-membered monocyclic or 8 to 11-membered bicyclic group which is partially or fully saturated, wherein 1, 2, 3, 4 or 5 of the carbon atoms are replaced by a heteroatom independently selected from O, S and N. Examples of "heterocyclyl" which are fully saturated 5 or 6-membered monocyclic rings include pyrrolidinyl, imidazolidinyl, pyrazolidinyl, tetrahydrofuranyl, dioxolanyl, piperidinyl, piperazinyl, morpholinyl, thiomorpholinyl, tetrahydrothienyl, dioxanyl, tetrahydro-2H-pyranyl and dithianyl. Examples of "heterocyclyl" groups which are partially saturated 5 or 6-membered monocyclic rings include oxazolinyl, isoaxazolinyl, imidazolinyl, pyrazolinyl, 1,2,3,6-tetrahydropyridyl and 3,6-dihydro-2H-pyranyl. Examples of "heterocyclyl" groups which are fully saturated 8 to 11-membered bicyclic rings include decahydroquinolinyl, octahydro-2H-1,4-benzoxazinyl and octahydro-1H-cyclopenta[b]pyridinyl. Examples of "heterocyclyl" groups which are partially saturated 8 to 11-membered bicyclic rings include 2,3-dihydro-1H-indolyl, 1,2,3,4-tetrahydroquinolinyl, 1,2,3,4-tetrahydroisoquinolinyl and 2,3,4,5-tetrahydro-1H-3-benzazepinyl.

Any of these groups may be attached to the rest of the molecule at any suitable position.

As used herein, the term "salt" refers to any salt of a compound according to the present invention prepared from an inorganic or organic acid or base, quaternary ammonium salts and internally formed salts. Physiologically acceptable salts are particularly suitable for medical applications because of their greater aqueous solubility relative to the parent compounds. Such salts must clearly have a physiologically acceptable anion or cation. Suitably physiologically acceptable salts of the compounds of the present invention include acid addition salts formed with inorganic acids such as hydrochloric, hydrobromic, hydroiodic, phosphoric, metaphosphoric, nitric and sulfuric acids, and with organic acids, such as tartaric, acetic, trifluoroacetic, citric, malic, lactic, fumaric, benzoic, formic, propionic, glycolic, gluconic, maleic, succinic, camphorsulfuric, isothionic, mucic, gentisic, isonicotinic, saccharic, glucuronic, furoic, glutamic, ascorbic, anthranilic, salicylic, phenylacetic, mandelic, embonic (pamoic), methanesulfonic, ethanesulfonic, pantothenic, stearic, sulfinilic, alginic, galacturonic and arylsulfonic, for example benzenesulfonic and p-toluenesulfonic, acids; base addition salts formed with alkali metals and alkaline earth metals and organic bases such as N,N-dibenzylethylenediamine, chloroprocaine, choline, diethanolamine, ethylenediamine, meglumaine (N-methylglucamine), lysine and procaine; and internally formed salts. Salts having a non-physiologically acceptable anion or cation are within the scope of the invention as useful intermediates for the preparation of physiologically acceptable salts and/or for use in non-therapeutic, for example, in vitro, situations.

In one embodiment, m is 0 or 1.

When $R_1$ contains an aryl moiety, ie $R_1$ is aryl, aryl$C_{1-4}$alkoxy, aryloxy, arylthio, arylmethyl, aroyl, aryloxymethyl, arylsulfonyl, aryl-NR'—, arylsulfonyloxy, arylsulfonyl$C_{1-4}$alkyl, arylsulfonamido, arylcarboxamido, arylsulfonamido$C_{1-4}$alkyl, arylcarboxamido$C_{1-4}$alkyl, aroyl$C_{1-4}$alkyl or aryl$C_{1-4}$alkanoyl, the aryl moiety is optionally substituted by one or two substituents selected from: halogen, cyano, $C_{1-2}$alkyl (e.g. methyl), fluoro$C_{1-2}$alkyl (eg trifluoromethyl), $C_{1-2}$alkoxy (e.g. methoxy), $C_{1-2}$alkylenedioxy (e.g. methylenedioxy), $C_{1-3}$alkanoyl (e.g. acetyl), $C_2$alkanoylamino (e.g. acetylamino), fluoro$C_1$alkylsulfonyl (e.g. trifluoromethylsulfonyl) and methylsulfonyl. For example, the aryl moiety is optionally substituted by methyl.

When $R_1$ is a group $NR_7R_8$, $R_7CON(R_8)(CH_2)_r$, $R_7R_8NCO(CH_2)_r$ or $R_7R_8NSO_2(CH_2)_r$ and $R_7CONR_8$ or $R_7R_8N$ together form a 4-, 5-, 6- or 7-membered azacyclic group, then this is characterised by: (i) containing one additional O, N or S atom in the azacycle, for example the azacyclic group being 1,4-morpholin-4-yl and/or (ii) having 1 or 2 optional $C_{1-2}$alkyl substituents whose carbon atoms are included in the azacyclic group's 3-8 carbon atoms. One, two or more F atoms can optionally be included as substituents of the carbon atoms of the heterocycle. The term "azacyclic group" should be interpreted to cover only stable azacycles such as 1,4-morpholine and piperazine and not for example 1,3-morpholine. Saturated azacycles, in particular piperidinyl, pyrrolidinyl, 1,4-morpholinyl, and including the corresponding α-oxo-azacycles $R_6CONR_7$, may be given as examples.

In one embodiment, $R_1$ is halogen, oxo, cyano, $C_{1-4}$alkyl (such as methyl, ethyl, propyl, isopropyl, butyl, tert-butyl), halo$C_{1-4}$alkyl (such as —$CF_3$, $CF_3CH_2$— or pentafluoroethyl), acetyl, trifluoromethoxy, $C_{3-6}$cycloalkyl$C_{1-4}$alkyl (such as cyclopropylmethyl), $C_{3-6}$cycloalkyl (such as cyclopropyl), $C_{1-4}$alkylsulfonyl, $C_{1-4}$alkylsulfonyloxy, $R_7RBNSO_2$ (where each of $R_7$ and $R_8$ is independently hydrogen or $C_{1-4}$alkyl or $R_7R_8N$ together form a 4-, 5-, 6- or 7-membered azacyclic group optionally containing one additional O, N or S atom in the azacycle and having 3-8 carbon atoms), a heterocyclyl, or a 5- or 6-membered heteroaromatic group which is optionally substituted by one or two substituents selected from: halogen, cyano, $C_{1-2}$alkyl (e.g. methyl), halo$C_{1-2}$alkyl (e.g. trifluoromethyl), $C_{1-2}$alkoxy (e.g. methoxy), $C_{1-2}$alkylenedioxy (e.g. methylenedioxy), $C_{1-3}$alkanoyl (e.g. acetyl), $C_2$alkanoylamino (e.g. acetylamino), halo$C_1$alkylsulfonyl (e.g. trifluoromethylsulfonyl) and methylsulfonyl.

For example, $R_1$ is selected from: halogen, $C_{1-4}$alkylsulfonyl (e.g. methylsulfonyl or ethylsulfonyl), halo$C_{1-4}$alkylsulfonyl (e.g. trifluoromethylsulfonyl), $C_{1-4}$alkylsulfonyloxy (e.g. methylsulfonyloxy), halo$C_{1-4}$alkylsulfonyloxy (e.g. trifluoromethylsulfonyloxy), $R_7R_8NSO_2$ (where each of $R_7$ and $R_8$ is independently hydrogen or $C_{1-4}$alkyl, e.g. N,N-dimethylaminosulfonyl, or where $R_7R_8N$ together form a 4-, 5-, 6- or 7-membered azacyclic group optionally containing one additional O, N or S atom in the azacycle and having 3-8 carbon atoms, e.g. a piperidin-1-ylsulfonyl, pyrrolidin-1-ylsulfonyl or 1,4-morpholin-4-ylsulfonyl), a 5- or 6-membered heteroaromatic or a heterocyclyl, each of which is optionally substituted by one or two substituents selected from: halogen, cyano, $C_{1-2}$alkyl (e.g. methyl or trifluoromethyl), $C_{1-2}$alkoxy (e.g. methoxy), $C_{1-2}$alkylenedioxy (e.g. methylenedioxy), $C_{1-3}$alkanoyl (e.g. acetyl), $C_2$alkanoylamino (e.g. acetylamino), halo$C_1$alkylsulfonyl (e.g. trifluoromethylsulfonyl) and methylsulfonyl.

Suitably, $R_1$ is bromo, cyano, hydroxy, chloro, methoxy, tert-butyl, methylsulfonyl, ethylsulfonyl, N,N-dimethylaminosulfonyl, pyrrolidin-1-ylsulfonyl, 1,4-morpholin-4-ylsulfonyl, 1-piperidinyl, methylsulfonyloxy, pyrazin-2-yl, 5-methyl-oxazol-2-yl or 5-methyl-isoxazol-3-yl.

In one embodiment, n is 0

In one embodiment, A is a 5- or 6-membered heteroaromatic ring, such for example oxazole, thiazole or indazole.

In another embodiment, A is a 5 to 6 membered heterocyclic ring such as for example morpholine or pyrrolidine.

In one embodiment, n is 1 and $R_2$ is fluoro or bromo.

In one embodiment, $R_3$ and $R_4$ are hydrogen at each occurrence.

In one embodiment, q is 2 or 3.

In one embodiment, $W_1$ and $W_2$ are both N.

In one embodiment, $R_5$ is hydrogen or methyl.

When $R_6$ is a group of formula (a), it may be for example optionally substituted phenyl, an optionally substituted bicyclic group such as quinolinyl (e.g. 2-, 3-, 4-, 5- or 6-quinolinyl), furyl (e.g. 2-furyl), thienyl (e.g. 2-thienyl), pyridyl (e.g. 4-pyridyl), indolyl, pyrazolopyrimidyl (e.g. pyrazolo[1,5-a]pyrimidyl), cinnolinyl, benzo[b]furanyl, thienopyridine or pyrrolopyridyl. In one embodiment, $R_5$ is optionally substituted phenyl, such as unsubstituted phenyl or fluorophenyl (e.g. 4-fluorophenyl), optionally substituted quinolinyl (e.g.

6-quinolinyl), furyl (e.g. 2-furyl), thienyl (e.g. 2-thienyl), pyridyl (e.g. 4-pyridyl), 2-methylquinolinyl or 4-methyl, 3-oxazol-5-yl.

When $R_6$ is a group of formula (b), examples include —$(CH_2)$—Z, —$(CHCH_3)$—Z and groups such as:

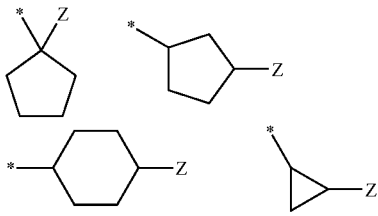

Examples of Z in formula (b) include those given for Z in formula (a).

Examples of the compounds of the present invention include:

2-methyl-7-(3-{[4-methyl-5-(2-methyl-5-quinolinyl)-4H-1, 2,4-triazol-3-yl]thio}propyl)-6,7,8,9-tetrahydro-5H-[1,3]oxazolo[4,5-h][3]benzazepine 7-(3-{[4-methyl-5-(2-methyl-5-quinolinyl)-4H-1,2,4-triazol-3-yl]thio}propyl)-6,7,8,9-tetrahydro-5H-[1,3]oxazolo[4,5-h][3]benzazepine 2-(1-methylethyl)-7-(3-{((4-methyl-5-(4-methyl-1,3-oxazol-5-yl)-4H-1,2,4-triazol-3-yl]thio}propyl)-6,7,8,9-tetrahydro-5H-[1,3]oxazolo[4,5-h][3]benzazepine 2-(1-methylethyl)-7-(3-{[4-methyl-5-(2-methyl-5-quinolinyl)-4H-1,2,4-triazol-3-yl]thio}propyl)-6,7,8,9-tetrahydro-5H-[1,3]oxazolo[4,5-h][3]benzazepine 2-(1,1'-dimethylethyl)-7-(3-{[4-methyl-5-(2-methyl-5-q uinolinyl)-4H-1,2,4-triazol-3-yl]thio}propyl)-6,7,8,9-tetrahydro-5H-[1,3]oxazolo[4,5-h][3]benzazepine 7-(3-{[4-methyl-5-(2-methyl-5-quinolinyl)-4H-1,2,4-triazol-3-yl]thio}propyl)-2-propyl-6,7,8,9-tetrahydro-5H-[1,3]oxazolo[4,5-h][3]benzazepine 7-(3-{[4-methyl-5-(2-methyl-5-quinolinyl)-4H-1,2,4-triazol-3-yl]thio}propyl)-2-(2,2,2-trifluoroethyl)-6,7,8,9-tetrahydro-5H-[1,3]oxazolo[4,5-h][3]benzazepine 7-(3-{[4-methyl-5-(2-methyl-5-quinolinyl)-4H-1,2,4-triazol-3-yl]thio}propyl)-2-(trifluoromethyl)-6,7,8,9-tetrahydro-5H-[1,3]oxazolo[4,5-h][3]benzazepine 8-(3-{[4-methyl-5-(2-methyl-5-q uinolinyl)-4H-1,2,4-triazol-3-yl]thio}propyl)-2,3,4,6,7,8,9,10-octahydro[1,4]oxazino[2,3-h][3]benzazepine 4-methyl-8-(3-{[4-methyl-5-(2-methyl-5-quinolinyl)-4H-1,2,4-triazol-3-yl]thio}propyl)-4,6,7,8,9,10-hexahydro[1,4]oxazino[2,3-h][3]benzazepin-3(2H)-one 4-methyl-8-(3-{[4-methyl-5-(4-methyl-1,3-oxazol-5-yl)-4H-1,2,4-triazol-3-yl]thio}propyl)-4,6,7,8,9,10-hexahydro[1,4]oxazino[2,3-h][3]benzazepin-3(2H)-one 2-(cyclopropylmethyl)-7-(3-{[4-methyl-5-(2-methyl-5-q uinolinyl)-4H-1,2,4-triazol-3-yl]thio}propyl)-6,7,8,9-tetrahydro-5H-[1,3]oxazolo[4,5-h][3]benzazepine 2-(cyclopropylmethyl)-7-(3-{[4-methyl-5-(4-methyl-1,3-oxazol-5-yl)-4H-1,2,4-triazol-3-yl]thio}propyl)-6,7,8,9-tetrahydro-5H-[1,3]oxazolo[4,5-h][3]benzazepine 2-ethyl-7-(3-[{4-methyl-5-(4-methyl-1,3-oxazol-5-yl)-4H-1,2,4-triazol-3-yl]thio}propyl)-6,7,8,9-tetrahydro-5H-[1, 3]oxazolo[(4,5-h][3]benzazepine 2-ethyl-7-(3-{[4-methyl-5-(2-methyl-5-quinolinyl)-4H-1,2, 4-triazol-3-yl]thio}propyl)-6,7,8,9-tetrahydro-5H-[1,3]oxazolo[4,5-h][3]benzazepine 3-methyl-7-(3-{[4-methyl-5-(2-methyl-5-quinolinyl)-4H-1, 2,4-triazol-3-yl]thio}propyl)-6,7,8,9-tetrahydro-5H-isoxazolo[4,5-h][3]benzazepine 3-methyl-7-[3-({4-methyl-5-[4-(trifluoromethyl)phenyl]-4H-1,2,4-triazol-3-yl}thio)propyl]-6,7,8,9-tetrahydro-5H-isoxazolo[4,5-h][3]benzazepine 2-cyclopropyl-7-(3-{[4-methyl-5-(2-methyl-5-q uinolinyl)-4H-1,2,4-triazol-3-yl]thio}propyl)-6,7,8,9-tetrahydro-5H-[1,3]oxazolo[4,5-h][3]benzazepine 2-methyl-7-(2-{[4-methyl-5-(2-methyl-5-quinolinyl)-4H-1, 2,4-triazol-3-yl]thio}ethyl)-6,7,8,9-tetrahydro-5H-[1,3]oxazolo[4,5-h][3]benzazepine 8-(3-{[4-methyl-5-(2-methyl-5-quinolinyl)-4H-1,2,4-triazol-3-yl]thio}propyl)-4-(methylsulfonyl)-2,3,4,6,7,8,9, 10-octahydro[1,4]oxazino[2,3-h][3]benzazepine 2-methyl-7-[3-({4-methyl-5-[4-(trifluoromethyl)phenyl]-4H-1,2,4-triazol-3-yl}thio)propyl]-6,7,8,9-tetrahydro-5H-[1,3]oxazolo[4,5-h][3]benzazepine 7-(3-{[5-(3,4-difluorophenyl)-4-methyl-4H-1,2,4-triazol-3-yl]thio}propyl)-2-methyl-6,7,8,9-tetrahydro-5H-[1,3]oxazolo[4,5-h][3]benzazepine 2-methyl-7-(3-{[4-methyl-5-(tetrahydro-2H-pyran-4-yl)-4H-1,2,4-triazol-3-yl]thio}propyl)-6,7,8,9-tetrahydro-5H-[1,3]oxazolo[4,5-h][3]benzazepine 2-ethyl-7-(3-[{4-methyl-5-(3-pyridinyl)-4H-1,2,4-triazol-3-yl]thio}propyl)-6,7,8,9-tetrahydro-5H-[1,3]oxazolo[4,5-h][3]benzazepine 2-ethyl-7-[3-({4-methyl-5-[4-(trifluoromethyl)phenyl]-4H-1,2,4-triazol-3-yl}thio)propyl]-6,7,8,9-tetrahydro-5H-[1, 3]oxazolo[4,5-h][3]benzazepine 7-(3-{[5-(3,4-difluorophenyl)-4-methyl-4H-1,2,4-triazol-3-yl]thio}propyl)-2-ethyl-6,7,8,9-tetrahydro-5H-[1,3]oxazolo[4,5-h][3]benzazepine 7-(3-{[4-methyl-5-(2-methyl-5-quinolinyl)-4H-1,2,4-triazol-3-yl]thio}propyl)-2-(1-piperidinyl)-6,7,8,9-tetrahydro-5H-[1,3]oxazolo[4,5-h][3]benzazepine N,N-dimethyl-7-(3-{[4-methyl-5-(2-methyl-5-quinolinyl)-4H-1,2,4-triazol-3-yl]thio}propyl)-6,7,8,9-tetrahydro-5H-[1,3]oxazolo[4,5-h][3]benzazepin-2-amine 3-ethyl-7-(3-{[4-methyl-5-(2-methyl-5-quinolinyl)-4H-1,2, 4-triazol-3-yl]thio}propyl)-6,7,8,9-tetrahydro-5H-isoxazolo[4,5-h][3]benzazepine 2-(1,3-dimethyl-1H-pyrazol-5-yl)-7-(3-{[4-methyl-5-(2-methyl-5-quinolinyl)-4H-1,2,4-triazol-3-yl]thio}propyl)-6,7,8,9-tetrahydro-5H-[1,3]oxazolo[4,5-h][3]benzazepine 2-(1,3-dimethyl-1H-pyrazol-5-yl)-7-(3-{[4-methyl-5-(4-methyl-1,3-oxazol-5-yl)-4H-1,2,4-triazol-3-yl]thio}propyl)-6,7,8,9-tetrahydro-5H-[1,3]oxazolo[4,5-h][3]benzazepine 7-(3-{[4-methyl-5-(2-methyl-5-q uinolinyl)-4H-1,2,4-triazol-3-yl]thio}propyl)-2-(pentafluoroethyl)-6,7,8,9-tetrahydro-5H-[1,3]oxazolo[4,5-h][3]benzazepine 7-(3-{[4-methyl-5-(4-methyl-1,3-oxazol-5-yl)-4H-1,2,4-triazol-3-yl]thio}propyl)-2-(pentafluoroethyl)-6,7,8,9-tetrahydro-5H-[1,3]oxazolo[4,5-h][3]benzazepine 3-ethyl-1-methyl-7-(3-{[4-methyl-5-(2-methyl-5-quinolinyl)-4H-1,2,4-triazol-3-yl]thio}propyl)-1,5,6,7,8,9-hexahydroazepino[4,5-f]indazole 2-(1,1-difluoroethyl)-7-(3-{[4-methyl-5-(2-methyl-5-quinolinyl)-4H-1,2,4-triazol-3-yl]thio}propyl)-6,7,8,9-tetrahydro-5H-[1,3]oxazolo[4,5-h][3]benzazepine 2-(1,1-difluoroethyl)-7-(3-{[4-methyl-5-(4-methyl-1,3-oxazol-5-yl)-4H-1,2,4-triazol-3-yl]thio}propyl)-6,7,8,9-tetrahydro-5H-[1,3]oxazolo[4,5-h][3]benzazepine 2-methyl-7-(3-{[4-methyl-5-(2-methyl-5-quinolinyl)-4H-1,2,4-triazol-3-yl]thio}propyl)-6,7,8,9-tetrahydro-5H-[1,3]thiazolo[4,5-h][3]benzazepine 2-methyl-7-(3-{[4-methyl-5-(4-methyl-1,3-oxazol-5-yl)-4H-1,2,4-triazol-3-yl]thio}propyl)-6,7,8,9-tetrahydro-5H-[1,3]thiazolo[4,5-h][3]benzazepine 2-ethyl-7-(3-{[4-methyl-5-(2-methyl-5-quinolinyl)-4H-1,2,4-triazol-3-yl]thio}propyl)-6,7,8,9-tetrahydro-5H-[1,3]thiazolo[4,5-h][3]benzazepine 2-ethyl-7-(3-{[4-methyl-5-(4-methyl-1,3-oxazol-5-yl)-4H-1,2,4-triazol-3-yl]thio}propyl)-6,7,8,9-tetrahydro-5H-[1,3]thiazolo[4,5-h][3]benzazepine 10-bromo-2-methyl-7-(3-{[4-methyl-5-(2-methyl-5-quinolinyl)-4H-1,2,4-triazol-3-yl]thio}propyl)-6,7,8,9-tetrahydro-5H-[1,3]oxazolo[4,5-h][3]benzazepine 10-bromo-7-(3-{[4-methyl-5-(2-methyl-5-quinolinyl)-4H-1,2,4-triazol-3-yl]thio}propyl)-2-(trifluoromethyl)-6,7,8,9-tetrahydro-5H-[1,3]oxazolo[4,5-h][3]benzazepine 10-bromo-2-methyl-7-(4-{[4-methyl-5-(2-methyl-5-quinolinyl)-4H-1,2,4-triazol-3-yl]thio}butyl)-6,7,8,9-tetrahydro-5H-[1,3]oxazolo[4,5-h][3]benzazepine 10-bromo-2-ethyl-7-(4-{[4-methyl-5-(2-methyl-5-quinolinyl)-4H-1,2,4-triazol-3-yl]thio}butyl)-6,7,8,9-tetrahydro-5H-[1,3]oxazolo[4,5-h][3]benzazepine 10-bromo-7-(4-{[4-methyl-5-(2-methyl-5-quinolinyl)-4H-1,2,4-triazol-3-yl]thio}butyl)-2-(trifluoromethyl)-6,7,8,9-tetrahydro-5H-[1,3]oxazolo[4,5-h][3]benzazepine 2,10-dimethyl-7-(4-{[4-methyl-5-(2-methyl-5-quinolinyl)-4H-1,2,4-triazol-3-yl]thio}butyl)-6,7,8,9-tetrahydro-5H-[1,3]oxazolo[4,5-h][3]benzazepine 2-ethyl-10-methyl-7-(4-{[4-methyl-5-(2-methyl-5-quinolinyl)-4H-1,2,4-triazol-3-yl]thio}butyl)-6,7,8,9-tetrahydro-5H-[1,3]oxazolo[4,5-h][3]benzazepine 10-methyl-7-(4-{[4-methyl-5-(2-methyl-5-quinolinyl)-4H-1,2,4-triazol-3-yl]thio}butyl)-2-(trifluoromethyl)-6,7,8,9-tetrahydro-5H-[1,3]oxazolo[4,5-h][3]benzazepine 2,10-dimethyl-7-(3-{[4-methyl-5-(2-methyl-5-quinolinyl)-4H-1,2,4-triazol-3-yl]thio}propyl)-6,7,8,9-tetrahydro-5H-[1,3]oxazolo[4,5-h][3]benzazepine 2-ethyl-10-methyl-7-(3-{[4-methyl-5-(2-methyl-5-quinolinyl)-4H-1,2,4-triazol-3-yl]thio}propyl)-6,7,8,9-tetrahydro-5H-[1,3]oxazolo[4,5-h][3]benzazepine 10-methyl-7-(3-{[4-methyl-5-(2-methyl-5-quinolinyl)-4H-1,2,4-triazol-3-yl]thio}propyl)-2-(trifluoromethyl)-6,7,8,9-tetrahydro-5H-[1,3]oxazolo[4,5-h][3]benzazepine 10-bromo-7-(1-methyl-3-{[4-methyl-5-(2-methyl-5-quinolinyl)-4H-1,2,4-triazol-3-yl]thio}propyl)-2-(trifluoromethyl)-6,7,8,9-tetrahydro-5H-[1,3]oxazolo[4,5-h][3]benzazepine 10-bromo-2-ethyl-7-(1-methyl-3-{[4-methyl-5-(2-methyl-5-quinolinyl)-4H-1,2,4-triazol-3-yl]thio}propyl)-6,7,8,9-tetrahydro-5H-[1,3]oxazolo[4,5-h][3]benzazepine 10-bromo-2-methyl-7-(1-methyl-3-{[4-methyl-5-(2-methyl-5-quinolinyl)-4H-1,2,4-triazol-3-yl]thio}propyl)-6,7,8,9-tetrahydro-5H-[1,3]oxazolo[4,5-h][3]benzazepine 10-methyl-7-(1-methyl-3-{[4-methyl-5-(2-methyl-5-quinolinyl)-4H-1,2,4-triazol-3-yl]thio}propyl)-2-(trifluoromethyl)-6,7,8,9-tetrahydro-5H-[1,3]oxazolo[4,5-h][3]benzazepine 2-(1-methylethyl)-7-(3-{[4-methyl-5-(2-methyl-5-quinolinyl)-4H-1,2,4-triazol-3-yl]thio}propyl)-3,5,6,7,8,9-hexahydroazepino[4,5-f]isoindol-1(2H)-one 2-(1-methylethyl)-7-(4-{[4-methyl-5-(2-methyl-5-quinolinyl)-4H-1,2,4-triazol-3-yl]thio}butyl)-3,5,6,7,8,9-hexahydroazepino[4,5-f]isoindol-1(2H)-one and salts thereof.

It will be appreciated that for use in medicine the salts of the compounds of the invention should be pharmaceutically (i.e physiologically) acceptable. Suitable pharmaceutically acceptable salts will be apparent to those skilled in the art and include for example acid addition salts formed with inorganic acids e.g. hydrochloric, hydrobromic, sulfuric, nitric or phosphoric acid; and organic acids e.g. succinic, maleic, acetic, fumaric, citric, tartaric, benzoic, p-toluenesulfonic, methanesulfonic or naphthalenesulfonic acid. Other non-pharmaceutically acceptable salts eg. oxalates, may be used, for example in the isolation of compounds of the invention and are included within the scope of this invention. Also included within the scope of the invention are solvates, hydrates, complexes and prodrugs of compounds of the invention.

Certain of the compounds of the invention may form acid addition salts with one or more equivalents of the acid. The present invention includes within its scope all possible stoichiometric and non-stoichiometric forms.

Certain groups/substituents included in the present invention may be present as isomers. The present invention includes within its scope all such isomers, including racemates, enantiomers, tautomers and mixtures thereof. Certain of the substituted heteroaromatic rings included in compounds of formula (I) may exist in one or more tautomeric forms. The present invention includes within its scope all such tautomeric forms, including mixtures.

Preferred compounds have a molecular weight of 800 or less. Still more preferred are compounds having a molecular weight of 600 or less. Generally, and without being limited thereto, such compounds may have higher oral bioavailability, and sometimes higher solubility and/or brain penetrancy. Molecular weight here refers to that of the unsolvated free base compound, excluding any molecular weight contributed by addition salts, solvent (e.g. water) molecules, prodrug molecular parts cleaved off in vivo, etc.

In general, the compounds or salts of the invention should be interpreted as excluding those compounds (if any) which are so chemically unstable, either per se or in water, that they are clearly unsuitable for pharmaceutical use through all administration routes, whether oral, parenteral or otherwise. Such compounds are known to the skilled chemist. Prodrugs or compounds which are stable ex vivo and which are convertable in the mammalian (e.g. human) body to the inventive compounds are however included.

The present invention also provides a process for preparing a compound of formula (I), which process comprises (a) reacting a compound of formula (II):

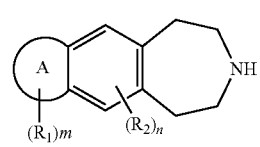

(II)

wherein $R_1$, m and A are as defined for formula (I), with a compound of formula (III):

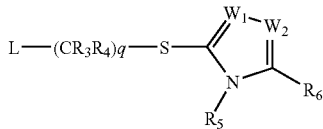

wherein $R_3$, $R_4$, q, $W_1$, $W_2$, $R_5$ and $R_6$ are as defined for formula (I), and L is a leaving group;
or
(b) reacting a compound of formula (IV):

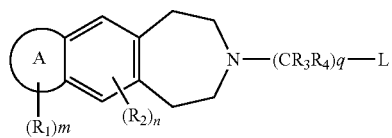

wherein A, $R_1$, $R_3$, $R_4$, m and q are as defined for formula (I) and L is a leaving group, with a compound of formula (V):

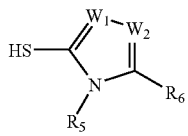

wherein $W_1$, $W_2$, $R_5$ and $R_6$ are as defined for formula (I); and optionally thereafter for step (a) or step (b):
  removing any protecting group(s); and/or
  forming a salt; and/or
  converting one compound of formula (I) to a different compound of formula (I).

In step (a), the leaving group, L, in compounds of formula (II) may be for example halogen, such as chlorine. The process of the present invention may be effected using conventional conditions for N-alkylation. For example, when L is a halogen such as chlorine, the reaction may be carried out in the presence of a source of iodide such as sodium iodide using a base such as potassium carbonate in a suitable solvent such as DMF at an appropriate temperature such as around 60° C. Alternatively L may be for example a sulfonyloxy group such as $C_{1-4}$alkylsulfonyloxy (e.g. methanesulfonyloxy or trifluoromethanesulfonyloxy); or arylsulfonyloxy wherein aryl is optionally substituted phenyl, e.g. para-toluenesulfonyloxy.

In step (b), the leaving group L may be as described for compounds of formula (II) above. It will be appreciated by those skilled in the art that the compound of formula (V) may be replaced by an eventual tautomeric form. For example, when L is a halogen such as chlorine, the reaction may be carried out in the presence of a source of iodide such as sodium iodide using a base such as diisopropylethylamine in a suitable solvent such as DMF at a suitable temperature, for example 80° C.

Compounds of formula (I) may be converted to another compound of formula (I) by suitable methods known to the skilled person, such as:

converting one form of A (e.g. a lactone) to a different form of A (e.g. an N-alkyl lactam); or
  replacing one $R_1$ (e.g. Cl) with a different $R_1$ (e.g. $NR_7R_8$).
  Compounds of formula (II), (III), (IV) and (V) may be prepared by methods disclosed herein, by methods known in the literature or are commercially available. For example, compounds of formula (VI):

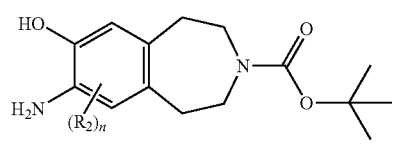

may be reacted with a carboxylic acid chloride derivative containing an appropriate $R_1$ group, followed by treatment with trifluoroacetic acid and heating, to form compounds of formula (II) wherein A is 2-substituted oxazole:

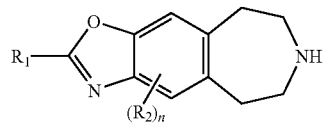

A compound of formula (III) may be prepared by reacting a compound of formula (V) as defined above with a compound of formula (VII):

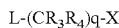

wherein $R_3$, $R_4$ and q are as defined for formula (I), and L and X are independently leaving groups. Appropriate leaving groups for L and X may be halogen such as Cl or Br, or a sulfonyloxy group such as $C_{1-4}$alkylsulfonyloxy (e.g. methanesulfonyloxy or trifluoromethanesulfonyloxy); or arylsulfonyloxy wherein aryl is optionally substituted phenyl, e.g. para-toluenesulfonyloxy.

Compounds of formula (IV) may be made for example by reacting a compound of formula (II) with a compound of formula (VIII).

Compounds of formula (I) have been found to exhibit affinity for dopamine receptors, in particular the $D_3$ receptor, and are expected to be useful in the treatment of disease states which require modulation of such receptors, such as psychotic conditions. Many of the compounds of formula (I) have also been found to have greater affinity for dopamine $D_3$ than for $D_2$ receptors.

The therapeutic effect of currently available antipsychotic agents (neuroleptics) is generally believed to be exerted via blockade of $D_2$ receptors; however this mechanism is also thought to be responsible for undesirable extrapyramidal side effects (eps) associated with many neuroleptic agents. Without wishing to be bound by theory, it has been suggested that blockade of the recently characterised dopamine $D_3$ receptor may give rise to beneficial antipsychotic activity without significant eps. (see for example Sokoloff et al, Nature, 1990; 347: 146-151; and Schwartz et al, Clinical Neuropharmacology, Vol 16, No. 4, 295-314, 1993). Preferred compounds of the present invention are therefore those which have higher (e.g. $\geq 10\times$ or $\geq 100\times$ higher) affinity for dopamine $D_3$ than dopamine $D_2$ receptors (such affinity can be measured using standard methodology for example using cloned dopamine receptors—see herein). Said compounds may advantageously be used as selective modulators of $D_3$ receptors.

Compounds of formula (I) will be used for treatment of all aspects of drug dependency including withdrawal symptoms from drugs of abuse such as alcohol, cocaine, opiates, nicotine, benzodiazepines and inhibition of tolerance induced by opioids. In addition, compounds of formula (I) and pharmaceutically acceptable salts and solvates thereof will be used to reduce craving and therefore will be useful in the treatment of drug craving. Drug craving can be defined as the incentive motivation to self-administer a psychoactive substance that was previously consumed. Three main factors are involved in the development and maintenance of drug craving: (1) Dysphoric states during drug withdrawal can function as a negative reinforcer leading to craving; (2) Environmental stimuli associated with drug effects can become progressively more powerful (sensitization) in controlling drug seeking or craving, and (3) A cognition (memory) of the ability of drugs to promote pleasurable effects and to alleviate a dysphoric state during withdrawal. Craving may account for the difficulty that individuals have in giving up drugs of abuse and therefore contributes significantly to the development and maintenance of drug dependence.

Within the context of the present invention, the terms describing the indications used herein are classified in the Diagnostic and Statistical Manual of Mental Disorders, 4th Edition, published by the American Psychiatric Association (DSM-IV) and/or the International Classification of Diseases, 10th Edition (ICD-10). The various subtypes of the disorders mentioned herein are contemplated as part of the present invention. Numbers in brackets after the listed diseases below refer to the classification code in DSM-IV.

Substance-related disorders including Substance Use Disorders such as Substance Dependence, Substance Craving and Substance Abuse; Substance-induced Disorders such as Substance Intoxication, Substance Withdrawal, Substance-induced Delirium, Substance-induced Persisting Dementia, Substance-Induced Persisting Amnestic Disorder, Substance-Induced Psychotic Disorder, Substance-induced Mood Disorder, Substance-induced Anxiety Disorder, Substance-induced Sexual Dysfunction, Substance-Induced Sleep Disorder and Hallucinogen Persisting Perception Disorder (Flashbacks); Alcohol-Related Disorders such as Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-Induced Persisting Dementia, Alcohol-Induced Persisting Amnestic Disorder, Alcohol-induced Psychotic Disorder, Alcohol-induced Mood Disorder, Alcohol-Induced Anxiety Disorder, Alcohol-Induced Sexual Dysfunction, Alcohol-Induced Sleep Disorder and Alcohol-Related Disorder Not Otherwise Specified (291.9); Amphetamine (or Amphetamine-Like)-Related Disorders such as Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-Induced Mood Disorder, Amphetamine-Induced Anxiety Disorder, Amphetamine-Induced Sexual Dysfunction, Amphetamine-Induced Sleep Disorder and Amphetamine-Related Disorder Not Otherwise Specified (292.9); Caffeine Related Disorders such as Caffeine Intoxication (305.90), Caffeine-Induced Anxiety Disorder, Caffeine-induced Sleep Disorder and Caffeine-Related Disorder Not Otherwise Specified (292.9); Cannabis-Related Disorders such as Cannabis Dependence (304.30), Cannabis Abuse (305.20), Cannabis Intoxication (292.89), Cannabis Intoxication Delirium, Cannabis-induced Psychotic Disorder, Cannabis-Induced Anxiety Disorder and Cannabis-Related Disorder Not Otherwise Specified (292.9); Cocaine-Related Disorders such as Cocaine Dependence (304.20), Cocaine Abuse (305.60), Cocaine Intoxication (292.89), Cocaine Withdrawal (292.0), Cocaine Intoxication Delirium, Cocaine-induced Psychotic Disorder, Cocaine-induced Mood Disorder, Cocaine-induced Anxiety Disorder, Cocaine-Induced Sexual Dysfunction, Cocaine-Induced Sleep Disorder and Cocaine-Related Disorder Not Otherwise Specified (292.9); Hallucinogen-Related Disorders such as Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-induced Psychotic Disorder, Hallucinogen-Induced Mood Disorder, Hallucinogen-Induced Anxiety Disorder and Hallucinogen-Related Disorder Not Otherwise Specified (292.9); Inhalant-Related Disorders such as Inhalant Dependence (304.60), Inhalant Abuse (305.90), Inhalant Intoxication (292.89), Inhalant Intoxication Delirium, Inhalant-induced Persisting Dementia, Inhalant-induced Psychotic Disorder, Inhalant-Induced Mood Disorder, Inhalant-Induced Anxiety Disorder and Inhalant-Related Disorder Not Otherwise Specified (292.9); Nicotine-Related Disorders such as Nicotine Dependence (305.1), Nicotine Withdrawal (292.0) and Nicotine-Related Disorder Not Otherwise Specified (292.9); Opioid-Related Disorders such as Opioid Dependence (304.00), Opioid Abuse (305.50), Opioid Intoxication (292.89), Opioid Withdrawal (292.0), Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9); Phencyclidine (or Phencyclidine-Like)-Related Disorders such as Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencyclidine-Induced Mood Disorder, Phencyclidine-Induced Anxiety Disorder and Phencyclidine-Related Disorder Not Otherwise Specified (292.9); Sedative-, Hypnotic-, or Anxiolytic-Related Disorders such as Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-Induced Psychotic Disorder, Sedative-, Hypnotic-, or Anxiolytic-Induced Mood Disorder, Sedative-, Hypnotic-, or Anxiolytic-Induced Anxiety Disorder Sedative-, Hypnotic-, or Anxiolytic-Induced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9); Polysubstance-Related Disorder such as Polysubstance Dependence (304.80); and Other (or Unknown) Substance-Related Disorders such as Anabolic Steroids, Nitrate Inhalants and Nitrous Oxide:

The compounds of formula (I) are of potential use in the treatment of psychotic disorders. Within the context of the present invention, the term "psychotic disorder" includes:
—Schizophrenia including the subtypes Paranoid Type (295.30), Disorganised Type (295.10), Catatonic Type (295.20), Undifferentiated Type (295.90) and Residual Type (295.60); Schizophreniform Disorder (295.40); Schizoaffective Disorder (295.70) including the subtypes Bipolar Type and Depressive Type; Delusional Disorder (297.1) including the subtypes Erotomanic Type, Grandiose Type, Jealous Type, Persecutory Type, Somatic Type, Mixed Type and Unspecified Type; Brief Psychotic Disorder (298.8); Shared Psychotic Disorder (297.3); Psychotic Disorder Due to a General Medical Condition including the subtypes With Delusions and With Hallucinations; Substance-Induced Psychotic Disorder including the subtypes With Delusions (293.81) and With Hallucinations (293.82); and Psychotic Disorder Not Otherwise Specified (298.9).

Furthermore, the compounds could have utility as adjunct therapy in Parkinsons Disease, particularly with compounds such as L-DOPA and possibly dopaminergic agonists, to reduce the side effects experienced with these treatments on long term use (e.g. see Schwartz et al., Brain Res. Reviews, 1998, 26, 236-242). From the localisation of $D_3$ receptors, it could also be envisaged that the compounds could also have utility for the treatment of substance abuse where it has been suggested that D3 receptors are involved (e.g. see Levant, 1997, Pharmacol. Rev., 49, 231-252). Examples of such substance abuse include alcohol, cocaine, heroin and nicotine abuse. Other conditions which may be treated by the compounds include dyskinetic disorders such as Parkinson's disease, neuroleptic-induced parkinsonism and tardive dyskinesias; depression; anxiety, cognitive impairment including memory disorders such as Alzheimers disease, eating disorders, sexual dysfunction, sleep disorders, emesis, movement disorders, obsessive-compulsive disorders, amnesia, aggression, autism, vertigo, dementia, circadian rhythm disorders and gastric motility disorders e.g. IBS.

In a further aspect therefore the present invention provides a method of treating a condition for which modulation (especially antagonism/inhibition) of dopamine receptors (especially dopamine $D_3$ receptors) is beneficial, which comprises administering to a mammal (e.g. human) in need thereof an effective amount of a compound of formula (I) or a pharmaceutically (i.e physiologically) acceptable salt thereof. Such conditions in particular include psychoses/psychotic conditions such as schizophrenia, and substance abuse and/or drug dependency.

The invention also provides the use of a compound of formula (I) or a pharmaceutically acceptable salt thereof in the manufacture of a medicament for the treatment of a condition in a mammal for which modulation (especially antagonism/inhibition) of dopamine receptors (especially dopamine $D_3$ receptors) is beneficial.

The invention also provides a compound of formula (I) or a pharmaceutically acceptable salt thereof for use in the treatment of a condition in a mammal for which modulation (especially antagonism/inhibition) of dopamine receptors (especially dopamine $D_3$ receptors) is beneficial.

In one embodiment, $D_3$ antagonists according to the present invention are used in the treatment of psychoses such as schizophrenia or in the treatment of substance abuse and/or drug dependency.

Thus, a still further aspect the invention provides a method of treating a psychotic condition (e.g. schizophrenia) or substance abuse and/or drug dependency which comprises administering to a mammal (e.g. human) in need thereof an effective amount of a compound of formula (I) as herein defined or a pharmaceutically acceptable salt thereof.

Also provided is the use of a compound of formula (I) or a pharmaceutically acceptable salt thereof in the manufacture of a medicament for the treatment of a psychotic condition (e.g. schizophrenia) or substance abuse and/or drug dependency in a mammal.

Also provided is a compound of formula (I) or a pharmaceutically acceptable salt thereof for use in the treatment of a psychotic condition (e.g. schizophrenia) or substance abuse and/or drug dependency in a mammal.

Also provided is a compound of formula (I) or a pharmaceutically acceptable salt thereof for use as an active therapeutic substance in a mammal, e.g. for use in the treatment of any of the conditions described herein.

"Treatment" includes prophylaxis, where this is appropriate for the relevant condition(s).

For use in medicine, the compounds of the present invention are usually administered as a standard pharmaceutical composition. The present invention therefore provides in a further aspect a pharmaceutical composition comprising a compound of formula (I) or a pharmaceutically (i.e physiologically) acceptable salt thereof and a pharmaceutically (i.e physiologically) acceptable carrier. The pharmaceutical composition can be for use in the treatment of any of the conditions described herein.

The compounds of formula (I) may be administered by any convenient method, for example by oral, parenteral (e.g. intravenous), buccal, sublingual, nasal, rectal or transdermal administration and the pharmaceutical compositions adapted accordingly.

The compounds of formula (I) and their pharmaceutically acceptable salts which are active when given orally can be formulated as liquids or solids, for example syrups, suspensions or emulsions, tablets, capsules and lozenges.

A liquid formulation will generally consist of a suspension or solution of the compound or pharmaceutically acceptable salt in a suitable liquid carrier(s) for example an aqueous solvent such as water, ethanol or glycerine, or a non-aqueous solvent, such as polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active substance in a pharmaceutically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas such as compressed air or an organic propellant such as a fluoro-chlorohydrocarbon. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

In one embodiment, the composition is in unit dose form such as a tablet, capsule or ampoule.

Each dosage unit for oral administration contains for example from 1 to 250 mg (and for parenteral administration contains for example from 0.1 to 25 mg) of a compound of the formula (I) or a pharmaceutically acceptable salt thereof calculated as the free base.

The pharmaceutically acceptable compounds of the invention will normally be administered in a daily dosage regimen (for an adult patient) of, for example, an oral dose of between 1 mg and 500 mg, for example between 10 mg and 400 mg, e.g. between 10 and 250 mg or an intravenous, subcutaneous, or intramuscular dose of between 0.1 mg and 100 mg, for example between 0.1 mg and 50 mg, e.g. between 1 and 25 mg of the compound of the formula (I) or a pharmaceutically acceptable salt thereof calculated as the free base, the compound being administered 1 to 4 times per day. Suitably the compounds will be administered for a period of continuous therapy, for example for a week or more.

Biological Test Methods

Binding Experiments on Cloned Dopamine (e.g. D2, D3 and D4) Receptors

The ability of the compounds to bind selectively to human D2/D3/D4 dopamine receptors can be demonstrated by measuring their binding to cloned receptors. The inhibition constants ($K_i$) of test compounds for displacement of [$^{125}$I]-Iodosulpride binding to human D2/D3 and [$^3$H]-YM-09151 to D4 dopamine receptors expressed in CHO cells were determined as follows. The cell lines were shown to be free from bacterial, fungal and mycoplasmal contaminants, and stocks of each were stored frozen in liquid nitrogen. Cultures were grown as monolayers or in suspension in standard cell culture media. Cells were recovered by scraping (from monolayers) or by centrifugation (from suspension cultures), and were washed two or three times by suspension in phosphate buffered saline followed by collection by centrifugation. Cell pellets were stored frozen at −80° C. Crude cell membranes were prepared by homogenisation followed by high-speed centrifugation, and characterisation of cloned receptors achieved by radioligand binding.

Preparation of Cho Cell Membranes: Cell Pellets were Gently Thawed at Room temperature, and resuspended in about 20 volumes of ice-cold Extraction buffer; 5 mM EDTA, 50 mM Trizma pre-set crystals (pH7.4@37° C.), 1 mM $MgCl_2$, 5 mM KCl and 120 mM NaCl. The suspension was homogenised using an Ultra-Turrax at full speed for 15 seconds. The homogenate was centrifuged at 18,000 r.p.m for 15 min at 4° C. in a Sorvall RC5C centrifuge. Supernatant was discarded, and homogenate re-suspended in extraction buffer then centrifugation was repeated. The final pellet was resuspended in 50 mM Trizma pre-set crystals (pH 7.4 @ 37° C.) and stored in 1 ml aliquot tubes at −80° C. (D2=3.0E+08 cells, D3=7.0E+07 cells and D4=1.0E+08 cells). The protein content was determined using a BCA protocol and bovine serum albumin as a standard (Smith, P. K., et al., Measurement of protein using bicinchoninic acid. Anal. Biochem. 150, 76-85 (1985)).

Binding experiments: Crude D2/D3 cell membranes were incubated with 0.03 nM [125I]-Iodosulpride (~2000 Ci/mmol; Amersham, U. K.) and D4 with 0.8 nM [$^3$H]-YM-09151 (~85 Ci/mmol; NEN, UK), and the test compound in a buffer containing 50 mM Trizma pre-set crystals (pH 7.4 @ 37° C.), 120 mM NaCl, 5 mM KCl, 2 mM $CaCl_2$, 1 mM $MgCl_2$, 0.3% (w/v) bovine serum albumin. The total volume is 0.2 ml and incubated in a water bath at 37° C. for 40 minutes. Following incubation, samples were filtered onto GF/B Unifilters using a Can berra Packard Filtermate, and washed four times with ice-cold 50 mM Trizma pre-set crystals (pH 7.4 @ 37° C.). The radioactivity on the filters was measured using a Can berra Packard Topcount Scintillation counter. Non-specific binding was defined with 10 μM SKF-102161 (YM-09151). For competition curves, 10 serial log concentrations of competing cold drug were used (Dilution range: 10 μM-10 pM). Competition curves were analysed using Inflexion, an iterative curve fitting programme in Excel. Results were expressed as pKi values where pKi=−log 10[Ki].

The exemplified compounds have pKi values within the range of 7.5-10.0 at the dopamine D3 receptor. pKi results are only estimated to be accurate to about ±0.3-0.5.

Functional Activity at Cloned Dopamine Receptors

The functional activity of compounds at human D2 and human D3 receptors (i.e. agonism or antagonism) may be determined using a Cytosensor Microphysiometer (McConnell H M et al Science 1992 257 1906-1912). In Microphysiometer experiments, cells (hD2_CHO or hD3_CHO) were seeded into 12 mm Transwell inserts (Costar) at 300000 cells/cup in foetal calf serum (FCS)-containing medium. The cells were incubated for 6 h at 37° C. in 5% $CO_2$, before changing to FCS-free medium. After a further 16-18 h, cups were loaded into the sensor chambers of the Cytosensor Microphysiometer (Molecular Devices) and the chambers perfused with running medium (bicarbonate-free Dulbecco's, modified Eagles medium containing 2 mM glutamine and 44 mM NaCl) at a flow rate of 100 ul/min. Each pump, cycle lasted 90 s. The pump was on for the first 60 s and the acidification rate determined between 68 and 88 s, using the Cytosoft programme. Test compounds were diluted in running medium. In experiments to determine agonist activity, cells were exposed (4.5 min for hD2, 7.5 min for hD3) to increasing concentrations of putative agonist at half hour intervals. Seven concentrations of the putative agonist were used. Peak acidification rate to each putative agonist concentration was determined and concentration-response curves fitted using Robofit [Tilford, N. S., Bowen, W. P. & Baxter, G. S. Br. J. Pharmacol. (1995), Vol. 115, 160P]. In experiments to determine antagonist potency, cells were treated at 30 min intervals with five pulses of a submaximal concentration of quinpirole (100 nM for hD2 cells, 30 nM for hD3 cells), before exposure to the lowest concentration of putative antagonist. At the end of the next 30 min interval, cells were pulsed again with quinpirole (in the continued presence of the antagonist) before exposure to the next highest antagonist concentration. In all, five concentrations of antagonist were used in each experiment. Peak acidification rate to each agonist concentration was determined and concentration-inhibition curves fitted using Robofit.

The present invention is illustrated using the following examples.

Preparation 1: 5-{5-[(3-Chloropropyl)thio]-4-methyl-4H-1,2,4-triazol-3-yl}-2-methylquinoline

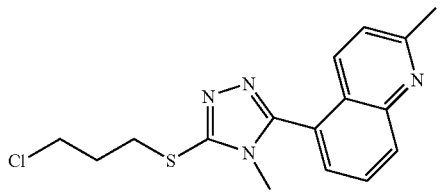

To 4-methyl-5-(2-methyl-5-quinolinyl)-2,4-dihydro-3H-1,2,4-triazole-3-thione (3.6 g, preparation reported in WO 02/40471) in ethanol (60 ml) containing 1-bromo-3-chloropropane (2.0 ml) was carefully added with stirring sodium hydride (0.60 g, 60% in mineral oil). The mixture was heated at reflux for 45 min. Volatiles were evaporated under reduced pressure and the residue submitted to column chromatography (EtOAc—acetone gradient). The material thus obtained was precipitated from hot EtOAc (20 ml) by adding petroleum ether (40-60, 50 ml), cooled and collected by filtration to provide the title compound as colourless crystals (2.1 g).

NMR ($^1$H, CDCl$_3$): δ 8.18 (d, 1H), 8.12 (d, 1H), 7.76 (t, 1H), 7.55 (d, 1H), 7.30 (d, 1H), 3.75 (t, 2H), 3.50 (t, 2H), 3.40 (s, 3H), 2.76 (s, 3H), 2.37 (m, 2H).

Preparation 2: 3-[(3-Chloropropyl)thio]-4-methyl-5-(4-methyl-1,3-oxazol-5-yl)-4H-1,2,4-triazole

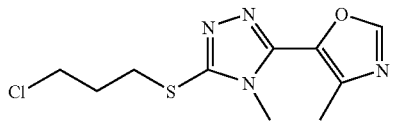

Ethyl 4-methyl-1,3-oxazole-5-carboxylate (7.0 g) was stirred at 25° C. with a solution of sodium hydroxide (8.0 g) in water (70 ml) for 2 h. The resulting solution was cooled in an ice bath and conc. aqueous HCl was slowly added with vigorous stirring until pH 2 had been reached. Filtration, washing with a small volume of cold water and drying resulted in an off-white solid (3.5 g).

This material (5.4 g) was allowed to react in DMF (60 ml) with 4-methyl-3-thiosemicarbazide (4.6 g), 1H-1,2,3-benzotriazol-1-ol (1.1 g), N-[2-(dimethylamino)ethyl]-N'-ethylcarbodiimide hydrochloride (8.6 g), and triethylamine (6.2 ml) for 14 h at 25° C. The solvent was evaporated under reduced pressure and the residue heated with NaOH (8.5 g) in water (150 ml) at 70° C. for 3.5 h. The resulting solution was cooled in an ice bath and conc. aqueous HCl (17.7 ml) was slowly added with vigorous stirring. Filtration, washing with a small volume of cold water and drying resulted in a yellow powder (5.3 g). To this material (4.8 g) in EtOH (60 ml) containing 1-bromo-3-chloropropane (3.7 ml) was carefully added with stirring sodium hydride (1.1 g, 60% in mineral oil). The mixture was heated at 60° C. for 1.5 h. Acetic acid (0.15 ml) was added, volatiles evaporated under reduced pressure and the residue submitted to column chromatography (EtOAc—acetone gradient). The material thus obtained was triturated with cyclohexane to provide the title compound as a faint yellow solid (6.1 g).

NMR ($^1$H, CDCl$_3$): δ 7.90 (s, 1H), 3.70 (s, 5H), 3.40 (t, 2H), 2.52 (s, 3H), 2.30 (m, 2H).

Preparation 3: 3-{5-[(3-Chloropropyl)thio]-4-methyl-4H-1,2,4-triazol-3-yl}pyridine

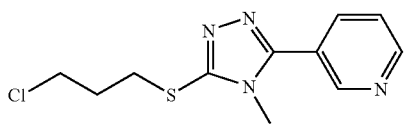

To 4-methyl-5-(3-pyridinyl)-2,4-dihydro-3H-1,2,4-triazole-3-thione (0.4 g, preparation reported in WO 02/40471) in ethanol (6 ml) sodium ethanolate (0.85 ml) was carefully added with stirring followed by 1-bromo-3-chloropropane (0.31 ml). The mixture was heated at 90° C. for 1 h. Acetic acid was added at room temperature until pH=4. After elimination of the solvent under reduced pressure the residue was partitioned between aqueous NaHCO$_3$ (saturated) and DCM. The organic layer was collected and the aqueous phase extracted twice with DCM. The combined DCM layers were concentrated and submitted to column chromatography (EtOAc—acetone gradient) to provide the title compound as white solid (0.360 g).

NMR ($^1$H, CDCl$_3$): δ 8.9 (bs, 1H), 8.8 (bs, 1H), 8.1 (d, 1H), 7.5 (m, 1H), 3.7 (t, 2H), 3.6 (s, 3H), 3.45 (t, 2H), 2.25 (m, 2H).

Preparation 4: 3-[(3-Chloropropyl)thio]-4-methyl-5-[4-(trifluoromethyl)phenyl]-4H-1,2,4-triazole

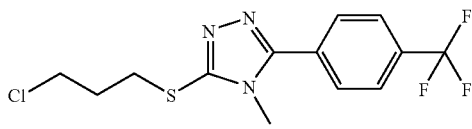

To 4-methyl-5-[4-(trifluoromethyl)phenyl]-2,4-dihydro-3H-1,2,4-triazole-3-thione (0.4 g, preparation reported in WO 02/40471) in ethanol (6 ml) sodium ethanolate (0.63 ml) was carefully added with stirring followed by 1-bromo-3-chloropropane (0.23 ml). The mixture was heated at 90° C. for 1 h. Acetic acid was added at room temperature until pH=4. After elimination of the solvent under reduced pressure the residue was partitioned between aqueous NaHCO$_3$ (saturated) and DCM. The organic layer was collected and the aqueous phase extracted twice with DCM. The combined DCM layers were concentrated and submitted to column chromatography (EtOAc—acetone gradient) to provide the title compound as white solid (0.394 g).

NMR (¹H, CDCl₃): δ 7.75 (s, 4H), 3.7 (t, 2H), 3.6 (s, 3H), 3.45 (t, 2H), 2.3 (m, 2H).

Preparation 5: 3-[(3-Chloropropyl)thio]-5-(3,4-difluorophenyl)-4-methyl-4H-1,2,4-triazole

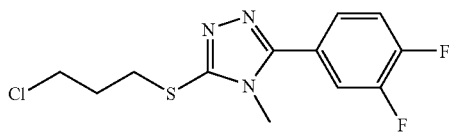

To 5-(3,4-difluorophenyl)-4-methyl-2,4-dihydro-3H-1,2,4-triazole-3-thione (0.4 g, preparation reported in WO 02/40471) in ethanol (6 ml) sodium ethanolate (0.72 ml) was carefully added with stirring followed by 1-bromo-3-chloropropane (0.26 ml). The mixture was heated at 90° C. for 1 h. Acetic acid was added at room temperature until pH=4. After elimination of the solvent under reduced pressure the residue was partitioned between aqueous NaHCO₃ (saturated) and DCM. The organic layer was collected and the aqueous phase extracted twice with DCM. The combined DCM layers were concentrated and submitted to column chromatography (EtOAc—acetone gradient) to provide the title compound as white solid (0.36 g).

NMR (¹H, CDCl₃): δ 7.45 (m, 1H), 7.35-7.2 (m, 2H), 3.7 (t, 2H), 3.6 (s, 3H), 3.4 (t, 2H), 2.3 (m, 2H).

Preparation 6: 3-[(3-Chloropropyl)thio]-4-methyl-5-(tetrahydro-2H-pyran-4-yl)-4H-1,2,4-triazole

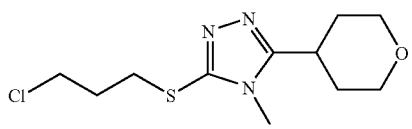

To 4-methyl-5-(tetrahydro-2H-pyran-4-yl)-2,4-dihydro-3H-1,2,4-triazole-3-thione (0.4 g, prepared in analogy to the method described in Preparation 2) in ethanol (6 ml) sodium ethanolate (0.83 ml) was carefully added with stirring followed by 1-bromo-3-chloropropane (0.30 ml). The mixture was heated at 90° C. for 1 h. Acetic acid was added at room temperature until pH=4. After elimination of the solvent under reduced pressure the residue was partitioned between aqueous NaHCO₃ (saturated) and DCM. The organic layer was collected and the aqueous phase extracted twice with DCM. The combined DCM layers were concentrated and submitted to column chromatography (EtOAc—acetone gradient) to give the title compound as white solid (0.173 g).

NMR (¹H, CDCl₃): δ 4.05 (d, 2H), 3.65 (t, 2H), 3.5 (t, 2H), 3.45 (s, 3H), 3.45 (t, 2H), 2.9 (m, 1H), 2.25 (m, 2H), 2.05 (m, 2H), 1.8 (d, 2H).

Preparation 7: 1,1-Dimethylethyl 7-hydroxy-1,2,4,5-tetrahydro-benzo[d]azepine-3-carboxylate

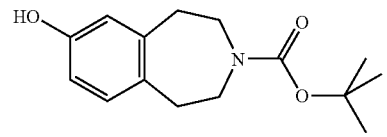

7-Methoxy-2,3,4,5-tetrahydro-1H-3-benzazepine (10 g, preparation reported in WO 02/40471) in 48% aqueous hydrobromic acid (350 ml) was allowed to stir at 10° C. for 4 h. The mixture was allowed to cool to 20° C. then evaporated to dryness, giving the crude hydroxy compound as a brown solid (14.5 g). This solid was dissolved in tetrahydrofuran (100 ml) and water (70 ml) and triethylamine (8 g) was added dropwise, followed by a solution of di-tert-butyl dicarbonate (14 g) in tetrahydrofuran (20 ml). The resulting mixture was allowed to stir at 20° C. for 16 h then partitioned between ethyl acetate (200 ml) and water (200 ml). The aqueous layer was extracted with ethyl acetate (100 ml). The combined organic extracts were Washed with saturated aqueous sodium bicarbonate (100 ml), dried over anhydrous sodium sulfate and evaporated to dryness. The resulting oil was purified by chromatography over silica gel, eluting with 10-30% ethyl acetate in hexane, affording the title compound as a white solid (8 g).

NMR (1H, CD₃OD): δ 6.96 (1H, d), 6.50-6.62 (2H, m), 4.95 (1H, s), 3.40-3.60 (4H, m), 2.75-2.87 (4H, m), 1.48 (9H, s). MS (m/z): 164 [MH-Boc]⁺.

Preparation 8: 1,1-Dimethylethyl 7-hydroxy-8-nitro-1,2,4,5-tetrahydro-3H-3-benzazepine-3-carboxylate

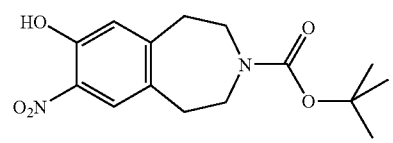

Nitric acid (70%, 3.44 ml) was added dropwise over 40 min with vigorous stirring to 1,1-dimethylethyl 7-hydroxy-1,2,4,5-tetrahydro-benzo[d]azepine-3-carboxylate (14.2 g) in DCM with cooling in an ice bath. After additional 5 min silica gel (15 g) and sodium bicarbonate powder (5 g) were added and stirring was continued for 1.5 h. The mixture was filtered through a layer (1 cm) of silica gel and the solids washed with EtOAc. The resulting solution was concentrated and submitted to column chromatography to provide the title compound as a yellow solid (8.54 g).

NMR (¹H, CDCl₃): δ 10.48 (s, 1H), 7.80 (s, 1H), 6.90 (s, 1H), 3.53 (m, 4H), 2.86 (m, 4H), 1.45 (s, 9H).

Preparation 9: 1,1-Dimethylethyl 7-amino-8-hydroxy-1,2,4,5-tetrahydro-3H-3-benzazepine-3-carboxylate

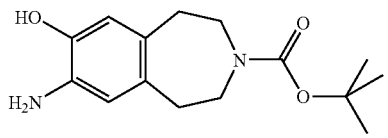

1,1-Dimethylethyl 7-hydroxy-8-nitro-1,2,4,5-tetrahydro-3H-3-benzazepine-3-carboxylate (8.2 g) was hydrogenated for 4 h under atmospheric pressure and 25° C. in the presence of 10% Pd/C (1.4 g) in EtOH (200 ml). The catalyst was removed by filtration and volatiles evaporated to provide the title compound as a grey solid (7.4 g).

NMR (¹H, CDCl₃): δ 6.5 (m, 2H), 2.6-3.6 (br m, 11H), 1.45 (s, 9H).

Preparation 10: 1,1-Dimethylethyl 2-methyl-5,6,8,9-tetrahydro-7H-[1,3]oxazolo[4,5-h][3]benzazepine-7-carboxylate

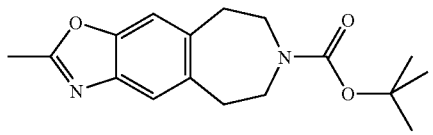

1,1-Dimethylethyl 7-amino-8-hydroxy-1,2,4,5-tetrahydro-3H-3-benzazepine-3-carboxylate (1.7 g) and trimethyl orthoacetate (1.2 ml) in the presence of pyridinium para-toluenesulfonate (0.16 g) were heated in dry DMF (20 ml) for 90 min at 70° C. followed by 2 h at 105° C. Volatiles were evaporated under reduced pressure to give the title compound which was used without further purification.

MS (m/z): 303 [MH]⁺.

Preparation 11: 2-Methyl-6,7,8,9-tetrahydro-5H-[1,3]oxazolo[4,5-h][3]benzazepine

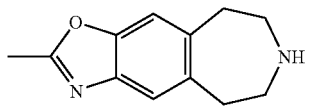

1,1-Dimethylethyl 2-methyl-5,6,8,9-tetrahydro-7H-[1,3]oxazolo[4,5-h][3]benzazepine-7-carboxylate (1.1 g) was exposed to trifluoroacetic acid (5 ml) in DCM (5 ml) for 90 min at 25° C. After elimination of volatiles under reduced pressure the residue was partitioned between aqueous Na₂CO₃ (2M) and DCM. The organic layer was collected and the aqueous phase extracted twice with DCM. The combined DCM layers were concentrated to give the title compound (0.84 g) as an off-white solid.

NMR (¹H, CDCl₃): δ 7.38 (s, 1H), 7.24 (s, 1H), 3.05 (m, 8H), 2.65 (s, 3H), NH not observed.

Preparation 12: 6,7,8,9-Tetrahydro-5H-[1,3]oxazolo[4,5-h][3]benzazepine

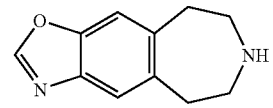

1,1-Dimethylethyl 7-amino-8-hydroxy-1,2,4,5-tetrahydro-3H-3-benzazepine-3-carboxylate was treated in analogy to Preparation 10 but using trimethyl orthoformiate. The product was treated in analogy to Preparation 11 to give the title compound as a faint yellow solid (used without further characterisation).

Preparation 13: 2-(1-Methylethyl)-6,7,8,9-tetrahydro-5H-[1,3]oxazolo[4,5-h][3]benzazepine

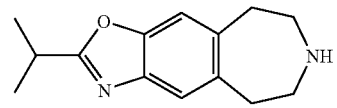

The title compound was prepared as described in General Procedure 2 from 1,1-dimethylethyl 7-amino-8-hydroxy-1,2,4,5-tetrahydro-3H-3-benzazepine-3-carboxylate and isobutyryl chloride.

Preparation 14: 2-(1,1-Dimethylethyl)-6,7,8,9-tetrahydro-5H-[1,3]oxazolo[4,5-h][3]benzazepine

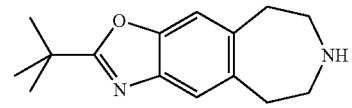

The title compound was prepared as described in General Procedure 2 from 1,1-dimethylethyl 7-amino-8-hydroxy-1,2,4,5-tetrahydro-3H-3-benzazepine-3-carboxylate and pivaloyl chloride.

MS (m/z): 245 [MH]⁺.

Preparation 15: 2-Propyl-6,7,8,9-tetrahydro-5H-[1,3]oxazolo[4,5-h][3]benzazepine

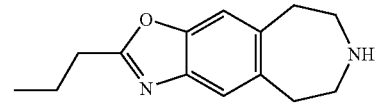

The title compound was prepared as described in General Procedure 2 from 1,1-dimethylethyl 7-amino-8-hydroxy-1,2,4,5-tetrahydro-3H-3-benzazepine-3-carboxylate and butyryl chloride.

Preparation 16: 2-(2,2,2-Trifluoroethyl)-6,7,8,9-tetrahydro-5H-[1,3]oxazolo[4,5-h][3]benzazepine

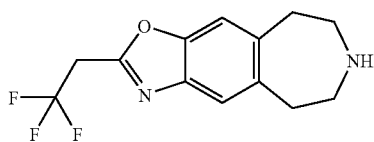

The title compound was prepared as described in General Procedure 2 from 1,1-dimethylethyl 7-amino-8-hydroxy-1,2,4,5-tetrahydro-3H-3-benzazepine-3-carboxylate and 3,3,3-trifluoropropanoyl chloride. The latter reactant had been obtained in chlorobenzene solution from the reaction of 3,3,3-trifluoropropanoic acid with oxalyl chloride (1 eq.) in the presence of a catalytic quantity of DMF.

Preparation 17: 2-(Trifluoromethyl)-6,7,8,9-tetrahydro-5H-[1,3]oxazolo[4,5-h][3]benzazepine

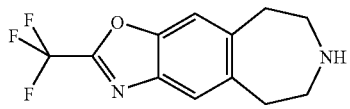

1,1-Dimethylethyl 7-amino-8-hydroxy-1,2,4,5-tetrahydro-3H-3-benzazepine-3-carboxylate (1.1 g) was treated with trifluoroacetic acid (2 ml) in DCM (2 ml). After 1 h volatiles were evaporated to give a faint purple solid (1.5 g). This material (0.36 g) was allowed to react with trifluoroacetic anhydride (0.31 ml) in trifluoroacetic acid (1.5 ml) for 90 min at 80° C. Volatiles were evaporated under reduced pressure. Chlorobenzene (2 ml) was added and the mixture heated at reflux for 6 h. The title compound (73 mg) was obtained following evaporation of the volatiles and column chromatography.
NMR ($^1$H, CDCl$_3$): δ 7.55 (s, 1H), 7.37 (s, 1H), 2.95-3.10 (m, 8H), NH not observed. MS (m/z): 257 [MH]$^+$.

Preparation 18: 1,1-Dimethylethyl 4-methyl-3-oxo-3,4,6,7,9,10-hexahydro[1,4]oxazino[2,3-h][3]benzazepine-8(2H)-carboxylate

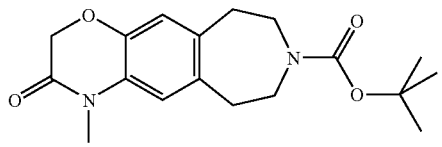

1,1-Dimethylethyl 7-amino-8-hydroxy-1,2,4,5-tetrahydro-3H-3-benzazepine-3-carboxylate (0.50 g) was allowed to react with chloroacetyl chloride (0.16 ml) in DCM (10 ml) in the presence of NaHCO$_3$ (0.27 g) and benzyltriethylammonium chloride (87 mg) for 90 min at 0° C. followed by reflux for 2 h (cf. Synthesis 1984, 851). Volatiles were evaporated, MeOH (5 ml) and aqueous NaOH (1 M, 5 ml) were added and the resulting mixture was stirred for 18 h. Aqueous NaHCO$_3$ was added, the resulting mixture concentrated to half volume under reduced pressure and extracted with ethyl acetate:DCM 3:1. The organic layer was dried (MgSO$_4$) and filtered. Volatiles were evaporated and the residue triturated with ethyl acetate:petroleum ether (40-60) 1:9 to provide a colourless solid (0.47 g). To this material (0.16 g) in DMF (2 ml) at 0° C. was added methyl iodide (0.036 ml) and NaH (60% in mineral oil, 29 mg). The mixture was vigorously stirred at 25° C. for 4 h. Water was added (10 ml), and the cooled mixture filtered, washed with water and the residue dried to give the title compound as a brown powder (0.16 g).
NMR ($^1$H, CDCl$_3$): δ 6.73 (s) and 6.70 (s, 2H), 4.55 (s, 2H), 3.50 (bs, 4H), 3.30 (s, 3H), 2-75-2.90 (m, 4H), 1.45 (s, 9H). MS (m/z): 277 [MH-C$_4$H$_8$]$^+$.

Preparation 19: 4-Methyl-4,6,7,8,9,10-hexahydro[1,4]oxazino[2,3-h][3]benzazepin-3(2H)-one

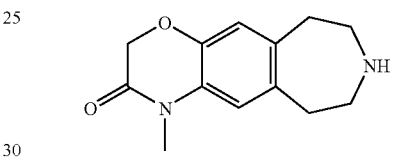

1,1-Dimethylethyl 4-methyl-3-oxo-3,4,6,7,9,10-hexahydro[1,4]oxazino[2,3-h][3]benzazepine-8(2H)-carboxylate (0.16 g) was treated with TFA (2 ml) in DCM (4 ml) for 3 h at 25° C. After elimination of volatiles under reduced pressure the residue was partitioned between aqueous NaHCO$_3$ and DCM. The organic layer was collected and the aqueous phase extracted twice with DCM. The combined DCM layers were dried (Na$_2$CO$_3$), filtered and concentrated to give the title compound as a colourless solid which was used without further analysis (0.11 g).

Preparation 20: 2-(Cyclopropylmethyl)-6,7,8,9-tetrahydro-5H-[1,3]oxazolo[4,5-h][3]benzazepine

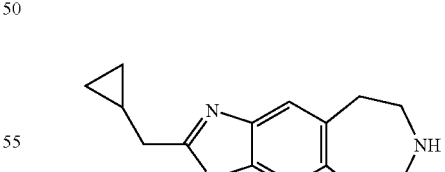

The title compound was prepared in analogy to General Procedure 2 using cyclopropyl acetyl chloride (obtained in situ from cyclopropyl acetic acid, oxalyl chloride (1.8 mmol, 1 eq) and cat. DMF in chlorobenzene at room temperature for 1 h) as a yellow liquid (0.66 mmol).

NMR ($^1$H, CD$_3$OD): δ 7.4 (m, 2H), 3.3-3.1 (m, 8H), 2.75 (d, 2H), 1.20-1.05 (m, 1H), 0.5 (m, 2H), 0.25 (m, 2H). MS (m/z): 243 [MH]$^+$.

Preparation 21: 2-Ethyl-6,7,8,9-tetrahydro-5H-[1,3]oxazolo[4,5-h][3]benzazepine

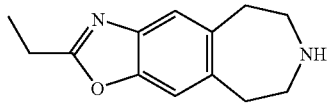

The title compound was prepared in analogy to General Procedure 2 from propionyl chloride (7.9 mmol) and was obtained as a yellow liquid (4.9 mmol).

NMR ($^1$H, CDCl$_3$): δ 7.40 (s, 1H), 7.25 (s, 1H), 3.1 (m, 8H), 3.95 (q, 2H), 2.35 (s, 1H), 1.45 (t, 3H). MS (m/z): 217 [MH]$^+$.

Preparation 22: 1-[8-Hydroxy-3-(trifluoroacetyl)-2,3,4,5-tetrahydro-1H-3-benzazepin-7-yl]ethanone

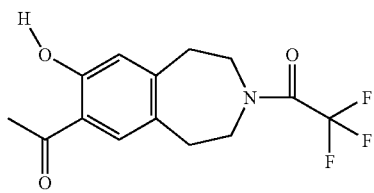

To a solution of 1,1-dimethylethyl 7-(methyloxy)-1,2,4,5-tetrahydro-3H-3-benzazepine-3-carboxylate (15 mmol, preparation reported in WO 02/40471) in DCM (30 ml) TFA (10 eq) was added at room temperature, the reaction mixture was stirred for 4 h. Solvent was removed under vacuum, residue was dissolved in DCM (30 ml) and Et$_3$N (2 eq) and trifluoroacetic anhydride (1.3 eq) was added at 0° C. The reaction mixture was stirred at room temperature for 3 h. Aqueous saturated NaHCO$_3$ was added and the mixture was extracted with DCM (3×30 ml). The combined organic layers were concentrated and residue dissolved in dichloroethane (10 ml) was added at 0° C. to a previously prepared suspension of AlCl$_3$ (2 eq) and acetyl chloride (1.04 eq) in dichloroethane (20 ml). The reaction mixture was stirred at room temperature for 16 h, quenched with HCl (1 M) and extracted with DCM (3×30 ml) The combined organic layers were concentrated and the residue was dissolved in DCM (30 ml) and BCl$_3$ (22.5 mmol, 1 M in DCM) was added at −78° C. The reaction mixture was stirred at −78° C. for 30 min then at room temperature for 1 h. Aqueous HCl (1 M, 20 ml) was added and the mixture was extracted twice with DCM. The combined organic layers were concentrated and submitted to column chromatography to provide the title compound (9.7 mmol) as a yellow oil.

NMR ($^1$H, CDCl$_3$): δ 12.2 (s, 1H), 7.45 (d, 1H), 6.8 (d, 1H), 3.65-3.80 (m, 4H), 2.95 (m, 4H), 2.65 (s, 3H). MS (m/z): 302 [MH]$^+$.

Preparation 23: 3-Methyl-6,7,8,9-tetrahydro-5H-isoxazolo[4,5-h][3]benzazepine

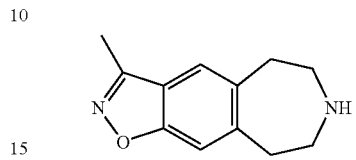

To a solution of 1-[8-hydroxy-3-(trifluoroacetyl)-2,3,4,5-tetrahydro-1H-3-benzazepin-7-yl]ethanone (7.4 mmol) in pyridine (15 ml) hydroxylamine hydrochloride (8.9 mmol) was added at room temperature and the reaction mixture was stirred for 4 h. Solvent was removed under reduced pressure, the residue was partitioned between 10% aqueous Na$_2$CO$_3$ and EtOAc. The organic layer was collected and the aqueous phase extracted twice with EtOAc. The combined organic layers were concentrated and the resulting material was dissolved in THF (5 ml) and Ph$_3$P (15 mmol) was added. The reaction mixture was stirred at 50° C. for 10 min while DEAD (15 mmol, 40% in toluene) was slowly added. The reaction mixture was stirred at 50° C. for 15 min then cooled to room temperature and water (0.4 ml) was added. Solvent was removed under reduced pressure and the residue was submitted to column chromatography to provide 3-methyl-7-(trifluoroacetyl)-6,7,8,9-tetrahydro-5H-isoxazolo[4,5-h][3]benzazepine (NMR $^1$H, CDCl$_3$): δ 7.4-7.3 (m, 2H), 3.85-3.65 (m, 4H), 3.15-3.05 (m, 4H), 2.55 (s, 3H). MS (m/z): 299 [MH]$^+$). Treatment with K$_2$CO$_3$ (4 eq) in MeOH:H$_2$O (1:1) gave the title compound (1.3 mmol) as pale yellow oil, which was used without further characterisation.

Preparation 24: 2-Cyclopropyl-6,7,8,9-tetrahydro-5H-[1,3]oxazolo[4,5-h][3]benzazepine hydrochloride

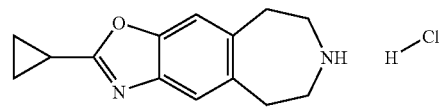

The title compound was prepared in analogy to General Procedure 2 from 1,1-dimethylethyl 7-amino-8-hydroxy-1,2,4,5-tetrahydro-3H-3-benzazepine-3-carboxylate (Preparation 9, 2.16 mmol) and cyclopropanecarbonyl chloride (2.4 mmol) to give the title compound (1.75 mmol) as a white solid.

NMR (¹H, DMSO-D6): δ 9.09 (bs, 2H), 7.50 (s, 1H), 7.47 (s, 1H), 3.78 (bs, 8H), 2.28 (m, 1H), 1.18 (m, 2H), 1.11 (m, 2H). MS (m/z): 229 [MH]⁺.

Preparation 25: 7-(2-Chloroethyl)-2-methyl-6,7,8,9-tetrahydro-5H-[1,3]oxazolo[4,5-h][3]benzazepine

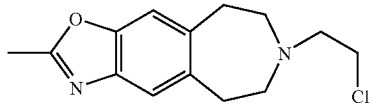

A mixture 2-methyl-6,7,8,9-tetrahydro-5H-[1,3]oxazolo[4,5-h][3]benzazepine (1 mmol), chloroacetaldehyde (2 mmol), NaBH(OAc)₃ (2 mmol) in dry DME (10 ml) was stirred at room temperature for 3 h. The mixture was partitioned between aqueous Na₂CO₃ (0.5 M) and DCM. The organic layer was collected and the aqueous phase extracted twice with DCM. The combined DCM layers were concentrated and submitted to column chromatography (EtOAc—acetone gradient) to provide the title compound (36% yield).

NMR (¹H, CDCl₃): δ 7.40 (s, 1H), 7.18 (s, 1H), 3.75 (t, 2H), 3.10 (m, 4H), 2.94 (t, 2H), 2.76 (m, 4H), 2.65 (s, 3H). MS (m/z): 265 [MH]⁺.

Preparation 26: 1,1-dimethylethyl 7-hydroxy-8-[(methylsulfonyl)amino]-1,2,4,5-tetrahydro-3H-3-benzazepine-3-carboxylate

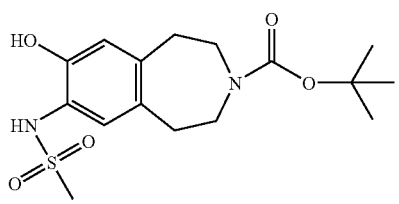

Pyridine (0.17 ml), methanesulfonyl chloride (0.16 ml) and dimethylaminopyridine (catalytic quantity) were added at 0° C. to a solution in DCM (10 ml) of 1,1-dimethylethyl 7-amino-8-hydroxy-1,2,4,5-tetrahydro-3H-3-benzazepine-3-carboxylate (0.5 g). The solution was stirred at room temperature overnight. Volatiles were evaporated under reduced pressure and the residue was partitioned between aqueous NaHCO₃ and DCM. The organic layer was concentrated and submitted to column chromatography to provide the title compound (0.53 g) as a yellow oil. MS (m/z): 357 [MH]⁺.

Preparation 27: 1,1-dimethylethyl 4-(methylsulfonyl)-3,4,6,7,9,10-hexahydro[1,4]oxazino[2,3-h][3]benzazepine-8(2H)-carboxylate

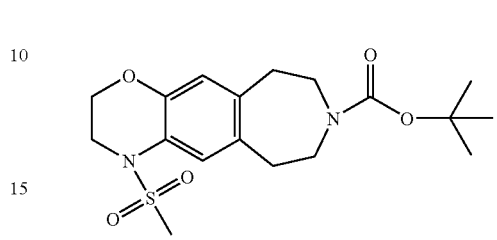

1,1-dimethylethyl 7-hydroxy-8-[(methylsulfonyl)amino]-1,2,4,5-tetrahydro-3H-3-benzazepine-3-carboxylate (0.55 g) and 1,2-dibromoethane (0.23 ml) in the presence of potassium carbonate (0.4 g) were heated in acetone/water (1/1, 8 ml) for 6 h at reflux. Volatiles were evaporated under reduced pressure, the residue was partitioned between aqueous NaHCO₃ and DCM. The organic layer was collected and the aqueous phase extracted twice with DCM. The combined organic layers were concentrated and submitted to column chromatography to provide the title compound (0.75 mmol) as a white slightly hygroscopic solid. MS (m/z): 383 [MH]⁺.

Preparation 28: 4-(methylsulfonyl)-2,3,4,6,7,8,9,10-octahydro[1,4]oxazino[2,3-h][3]benzazepine

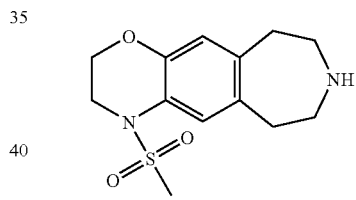

The title compound (30 mg) was prepared in analogy to Preparation 11 from 1,1-dimethylethyl 4-(methylsulfonyl)-3,4,6,7,9,10-hexahydro[1,4]oxazino[2,3-h][3]benzazepine-8(2H)-carboxylate (55 mg). MS (m/z): 283 [MH]⁺.

Preparation 29: 1,1-dimethylethyl 2-thioxo-2,3,5,6,8,9-hexahydro-7H-[1,3]oxazolo[4,5-h][3]benzazepine-7-carboxylate

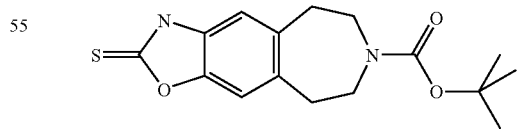

1,1-Dimethylethyl 7-amino-8-hydroxy-1,2,4,5-tetrahydro-3H-3-benzazepine-3-carboxylate (3.6 mmol) and potassium [(ethyloxy)carbonothioyl]sulfide (3.96 mmol) were suspended in pyridine (6 ml) and the reaction mixture was heated at 70° C. for 3 h. The solvent was removed under reduced pressure providing a crude product that after dissolution in ethyl acetate, washing with water and evaporation of the organic phase under reduced pressure gave the title compound as a yellow solid (2.5 mmol, 69% yield).

NMR (¹H, DMSO-D6): δ 7.05 (s, 1H), 6.9 (s, 1H), 3.4 (bs, 4H), 2.8 (bs, 4H), 1.35 (s, 9H).

Preparation 30: 2-(1-piperidinyl)-6,7,8,9-tetrahydro-5H-[1,3]oxazolo[4,5-h][3]benzazepine bis(trifluoroacetate)

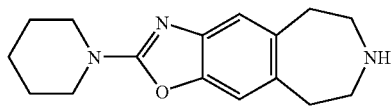

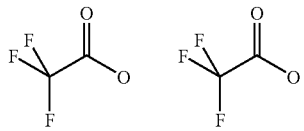

1,1-dimethylethyl 2-thioxo-2,3,5,6,8,9-hexahydro-7H-[1,3]oxazolo[4,5-h][3]benzazepine-7-carboxylate (0.134 mmol) and piperidine (0.27 mmol) were dissolved in toluene (1 ml). The reaction mixture was heated at 100° C. for 2 h. the solvent was removed under reduced pressure, then toluene (1 ml) and piperidine (0.27 mmol) were further added and the reaction was heated at 100° C. for 3 h. The solvent was removed under reduced pressure. The crude product was dissolved in DCM (2 ml), trifluoroacetic acid (1 ml) was added and the reaction was stirred for 2 h. Volatiles were removed under reduced pressure to give the title compound that was used without further purification.

MS (m/z): 271 [MH]⁺.

Preparation 31: N,N-dimethyl-6,7,8,9-tetrahydro-5H-[1,3]oxazolo[4,5-h][3]benzazepin-2-amine

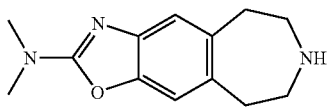

The title compound was prepared as described in Preparation 30 starting from 1,1-dimethylethyl 2-thioxo-2,3,5,6,8,9-hexahydro-7H-[1,3]oxazolo[4,5-h][3]benzazepine-7-carboxylate (1.7 mmol) and dimethyl amine (2M/THF, 13.7 mmol) in a sealed vial heating at 70° C. for 4 h. The title compound was obtained as a free base after DCM/NaHCO₃ work-up (0.2 mmol) and used without further purification.

MS (m/z): 232 [MH]⁺.

Preparation 32: 3-ethyl-7-(trifluoroacetyl)-6,7,8,9-tetrahydro-5H-isoxazolo[4,5-h][3]benzazepine

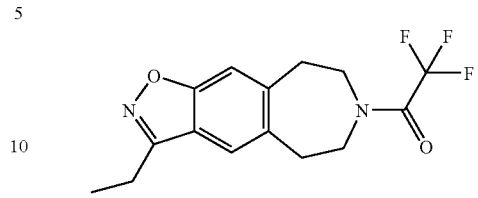

1,1-Dimethylethyl 7-(methyloxy)-1,2,4,5-tetrahydro-3H-3-benzazepine-3-carboxylate (15 mmol) was converted to 7-(methyloxy)-3-(trifluoroacetyl)-2,3,4,5-tetrahydro-1H-3-benzazepine as described in the initial steps of Preparation 23. This material (14 mmol) dissolved in dichloroethane (10 mL) was added at 0° C. to a previously prepared suspension of AlCl₃ (4 eq) and propionyl chloride (1.3 eq) in dichloroethane (20 mL). The reaction mixture was stirred in a defrosting ice bath. After 4 h it had reached 12° C. when aqueous HCl (2 M, 40 mL) was carefully added over 20 min. Diethyl ether was added, layers separated and the organic layer washed with water and brine and dried over MgSO₄. Volatiles were evaporated and the residue triturated with diethyl ether: cyclohexane 1:1 and then with diethyl ether to give a colourless powder (1-[8-hydroxy-3-(trifluoroacetyl)-2,3,4,5-tetrahydro-1H-3-benzazepin-7-yl]-1-propanone, 1.2 g). To a solution of this material (0.43 g) in pyridine (2 mL) hydroxylamine hydrochloride (0.10 g) was added at room temperature and the reaction mixture was kept for 16 h. Additional hydroxylamine hydrochloride (0.03 g) was added. After 5 h the solvent was removed under vacuum, the residue treated with water (2 mL) and methanol (4 mL) with stirring until a solid started to form. Additional water (6 mL) was added. The resulting solid was collected by filtration, washed (water) and dried to give a white powder (0.39 g). This material (0.10 g) was dissolved in THF (1 ml) and Ph₃P (0.13 g) was added. The reaction mixture was stirred at 50° C. while diisopropyl azodicarboxylate (94 μL) was added over 1 min, resulting in an orange solution. The reaction mixture was stirred at 50° C. for 15 min, then cooled to room temperature, and water (4 μL) was added. Solvent was removed under vacuum and the residue was submitted to column chromatography to provide the title compound (21 mg, colourless solid/film) of acceptable purity for further conversion.

NMR (1H, CDCl₃): δ 7.4-7.3 (m, 2H), 3.85-3.65 (m, 4H), 3.1 (bs, 4H), 2.9-3.05 (m, 2H), 1.4-1.5 (m, 3H).

Preparation 32: 3-Ethyl-6,7,8,9-tetrahydro-5H-isoxazolo[4,5-h][3]benzazepine

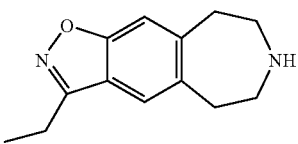

Treatment of 3-ethyl-7-(trifluoroacetyl)-6,7,8,9-tetrahydro-5H-isoxazolo[4,5-h][3]benzazepine (21 mg) with Na₂CO₃ (1 mL, 1 M in water) in MeOH (2 mL) at reflux for 3 h followed by partitioning between water and dichloromethane and evaporation of the volatiles from the organic phase gave the title compound as a solidifying yellow oil in quantitative yield. The material was used as such without further characterisation.

Preparation 34: 2-(1,3-Dimethyl-1H-pyrazol-5-yl)-6,7,8,9-tetrahydro-5H-[1,3]oxazolo[4,5-h][3]benzazepine

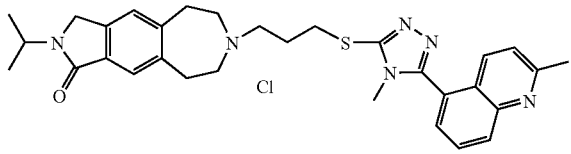

The title compound was prepared as described in General Procedure 2 from 1,1-dimethylethyl 7-amino-8-hydroxy-1,2,4,5-tetrahydro-3H-3-benzazepine-3-carboxylate and 1,3-dimethyl-1H-pyrazole-5-carbonyl chloride. The latter reactant had been obtained in dichloromethane solution from the reaction of 1,3-dimethyl-1H-pyrazole-5-carboxylic acid (1.3 eq.) in the presence of a catalytic quantity of dimethylformamide, followed by evaporation of the volatiles after 1.5 h at 25° C.

MS (m/z): 283 [MH]+.

Preparation 35: 2-(Pentafluoroethyl)-6,7,8,9-tetrahydro-5H-[1,3]oxazolo[4,5-h][3]benzazepine

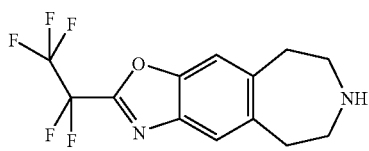

1,1-Dimethylethyl 7-amino-8-hydroxy-1,2,4,5-tetrahydro-3H-3-benzazepine-3-carboxylate (0.48 g) was treated with pentafluoropropionyl anhydride (1.2 eq.) and pyridine (1.2 eq.) in chlorobenzene at reflux for 5 h. After this time conc. H$_2$SO$_4$ (1 drop) was added and heating continued. After 1 h polyphosphoric acid was added (ca. 0.5 g) and heating continued for 30 min when mass spectrocopy analysis indicated complete cyclocondensation. Volatiles were evaporated, aqueous Na$_2$CO$_3$ carefully added and the mixture extracted with dichloromethane. The title compound (0.34 g) was obtained as a colourless solid following evaporation of the volatiles and column chromatography.

Preparation 36: 1,1-Dimethylethyl 7-hydroxy-8-propanoyl-1,2,4,5-tetrahydro-3H-3-benzazepine-3-carboxylate

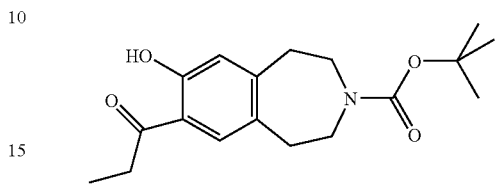

1-[8-Hydroxy-3-(trifluoroacetyl)-2,3,4,5-tetrahydro-1H-3-benzazepin-7-yl]-1-propanone (17 mmol, see initial step in Preparation 32) was briefly heated with Na$_2$CO$_3$ (20 mmol) in water (20 mL) and methanol (20 mL) to 70° C. and then kept with stirring in the slowly cooling oil bath for 16 h. Volatiles were evaporated and to the remainder was added water (10 mL), tetrahydrofuran (30 mL) and di-tert-butyl dicarbonate (2.3 g). The mixture was stirred for 24 h, filtered and the solids washed with EtOAc. The resulting solutions were partitioned between water and additional EtOAc, the organic layer washed (brine), volatiles evaporated under reduced pressure and the residue triturated with cyclohexane (15 mL) to give the title compound as a yellow solid (2.4 g).

NMR ($^1$H, CDCl$_3$): δ 12.22 (s, 1H), 7.45 (s, 1H), 6.72 (s, 1H), 3.45-3.6 (m, 4H), 2.97 (q, 2H), 2.8-2.9 (m, 4H), 1.47 (s, 9H), 1.21 (t, 3H).

Preparation 37: 1,1-Dimethylethyl 7-{[(nonafluorobutyl)sulfonyl]oxy}-8-propanoyl-1,2,4,5-tetrahydro-3H-3-benzazepine-3-carboxylate

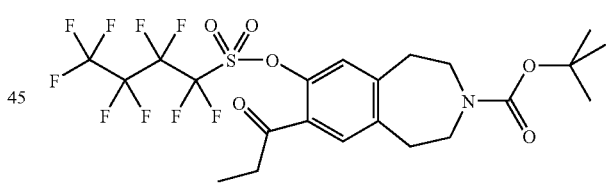

To 1,1-dimethylethyl 7-hydroxy-8-propanoyl-1,2,4,5-tetrahydro-3H-3-benzazepine-3-carboxylate (6.9 mmol) and nonaflyl fluoride (1.9 mL) in dimethylformamide (15 mL) and toluene (5 mL) was added NaH (1.5 eq.) with vigorous stirring and cooling in an ice bath. After 10 min the mixture was allowed to warm to 25° C. The following steps were sequentially taken in order to achieve complete consumption of the starting material: Addition of N,N-dimethyl-4-pyridinamine (0.04 g), heating to 100° C., addition of nonaflyl fluoride (1.9 mL) and ethyl[bis(1-methylethyl)]amine (3.6 mL) with heating at 70° C. for 4 h followed by 3 d at 25° C. The resulting mixture was partitioned between aqueous NaHCO$_3$ and dichloromethane, the aqueous layer extracted with EtOAc, volatiles from the combined organic layers evaporated and the residue purified by column chromatography to give 1.5 g of a yellow viscous oil.

MS (m/z): 546 [M-C$_4$H$_8$+H]+, 624 [MNa]+.

Preparation 38: 3-Ethyl-1-methyl-1,5,6,7,8,9-hexahydroazepino[4,5-f]indazole

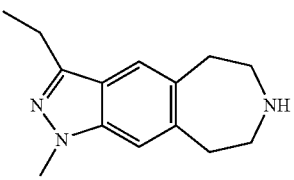

1,1-Dimethylethyl 7-{[(nonafluorobutyl)sulfonyl]oxy}-8-propanoyl-1,2,4,5-tetrahydro-3H-3-benzazepine-3-carboxylate (0.30 g) was allowed to react with methyl hydrazine (85 µL) in pyridine (1 mL) in the presence of pyridinium para-toluenesulfonate (0.2 eq.) for 4 d. The mixture was partitioned between aqueous $Na_2CO_3$ (0.5 M) and dichloromethane. This mixture was applied to an Isolute HM-N cartridge, eluting with dichloromethane. Volatiles were evaporated and the residue in dioxane (2 mL) added to a pre-formed, by sonication at 40° C. for 40 min, mixture of palladium acetate (13 mg), 2,2'-bis(diphenylphosphino)-1,1'-binaphthyl (53 mg) and $Cs_2CO_3$ (0.26 g) in dioxane (3 mL). The resulting black mixture was heated at 100° C. for 5 h, partitioned between water and EtOAc, the organic layer washed (brine), volatiles evaporated and the residue submitted to column chromatography to give 48 mg of a yellow oil enriched in the desired material according to MS. This material was dissolved in dichloromethane (3 mL) and trifluoroacetic acid (1 mL). After 16 h the solvent was removed under vacuum and the residue submitted to column chromatography to give the title compound (10 mg) as a faint yellow film.

MS (m/z): 230 $[MH]^+$.

Preparation 39: 2-(1,1-Difluoroethyl)-6,7,8,9-tetrahydro-5H-[1,3]oxazolo[4,5-h][3]benzazepine

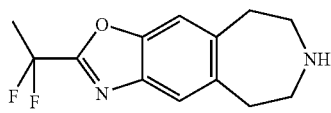

2,2-Difluoropropionic acid (0.28 g) was allowed to react in chlorobenzene (4.7 mL) containing 3 drops dimethylformamide with oxalyl chloride (0.22 g) for 1.5 h at 25° C., resulting in a ca. 0.5 M solution. 1.6 mL of this solution was added to 1,1-dimethylethyl 7-amino-8-hydroxy-1,2,4,5-tetrahydro-3H-3-benzazepine-3-carboxylate (0.17 g) containing pyridine (0.13 mL) and heated at reflux for 5 h. Polyphosphoric acid (ca. 0.4 g) was added and heating continued at 110° C. for 40 min. Volatiles were evaporated, to the residue with cooling in an ice bath carefully added water and $Na_2CO_3$ (until pH 8-9) and the mixture extracted 3 times with dichloromethane. The title compound (0.080 g) was obtained as a colourless solid following evaporation of the volatiles from the combined organic extracts and used in the next step without further purification.

Preparation 40: 3-acetyl-7-nitro-2,3,4,5-tetrahydro-1H-3-benzazepine

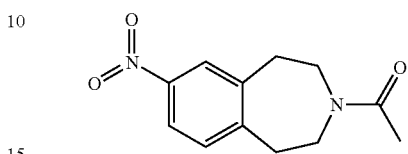

To a cooled solution of $HNO_3$ (70%) at 10° C., 3-acetyl-2,3,4,5-tetrahydro-1H-3-benzazepine (6.8 g, preparation reported in WO 02/40471) was added portionwise over 20 min. After addition mixture was allowed to warm at rt. and stirred for further 4 h. Mixture was poured into ice and pH adjusted to 11 using NaOH (conc) then was extracted with DCM. The organic layer was collected and the aqueous phase extracted twice with DCM. The combined DCM layers were concentrated to provide the target compound (7.74 g), which was used in further conversions without any purification.

NMR ($^1H$, $CDCl_3$): δ 8.00 (s, 1H), 7.25 (dd, 2H), 3.75 (m, 2H), 3.60 (m, 2H), 3.05 (2t, 4H), 2.15 (s, 3H). MS (m/z): 235 $[MH]^+$.

Preparation 41: 7-nitro-2,3,4,5-tetrahydro-1H-3-benzazepine

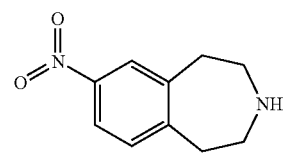

A solution of 3-acetyl-7-nitro-2,3,4,5-tetrahydro-1H-3-benzazepine (2.9 g) in HCl (conc) (200 ml) as refluxed for 48 h. Mixture was cooled at 0° C. and neutralised with NaOH (conc.) then was extracted with DCM. The organic layer was collected and the aqueous phase extracted twice with DCM. The combined DCM layers were concentrated to provide the target compound (2.33 g).

MS (m/z): 193 $[MH]^+$.

Preparation 42: 1,1-dimethylethyl 7-nitro-1,2,4,5-tetrahydro-3H-3-benzazepine-3-carboxylate

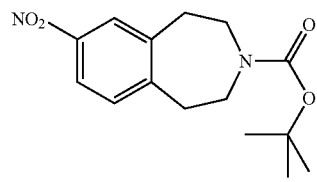

To a solution of 7-nitro-2,3,4,5-tetrahydro-1H-3-benzazepine (2.33 g) in dry DCM (120 ml, TEA (4.2 ml 2.5 eq), $BOC_2O$ (6.1 g, 2.3 eq.), DMAP (296 mg, 0.2 eq.) were added.

The mixture was stirred at rt. for 1 h then the solvent was evaporated in vacuo. The material thus obtained was purified by flash chromatography over silica gel (eluting with 20% ethyl acetate in hexane) to give the title compound (3.25 g).

MS (m/z):237 [M-56]+.

Preparation 43: 1,1-dimethylethyl 7-amino-1,2,4,5-tetrahydro-3H-3-benzazepine-3-carboxylate

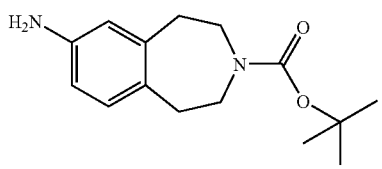

1,1-dimethylethyl 7-nitro-1,2,4,5-tetrahydro-3H-3-benzazepine-3-carboxylate (3.25 g) was hydrogenated for 3 h under atmospheric pressure at 25° C. in the presence of 10% Pd/C (0.32 g) in MeOH (130 ml). The catalyst was removed by filtration, the solvent evaporated under reduced pressure and the resulting residue was purified by flash chromatography over silica gel (eluting with 40% ethyl acetate in hexane) to give the title compound (2.55 g).

MS (m/z): 207 [M-56]+.

Preparation 44: 1,1-dimethylethyl 7-(acetylamino)-1,2,4,5-tetrahydro-3H-3-benzazepine-3-carboxylate

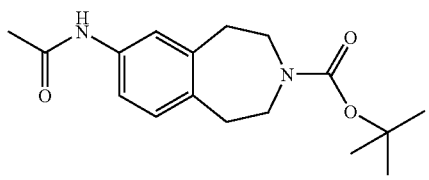

1,1-dimethylethyl 7-amino-1,2,4,5-tetrahydro-3H-3-benzazepine-3-carboxylate (995 mg) was stirred in dry DCM (10 ml) and treated with TEA (0.634 ml) and acethyl chloride (0.275 ml) and stirred at rt. for 3 h. Mixture was then partitioned between aqueous saturated NaHCO₃ and DCM. The organic layer was collected and the aqueous phase extracted twice with DCM. The combined DCM layers were concentrated and the residue was purified by flash chromatography over silica gel, eluting with 50% ethyl acetate in hexane, affording the title compound (818 mg).

MS (m/z): 305 [MH]+, 327 [M+Na]+.

Preparation 45: 1,1-dimethylethyl 7-(ethanethioylamino)-1,2,4,5-tetrahydro-3H-3-benzazepine-3-carboxylate

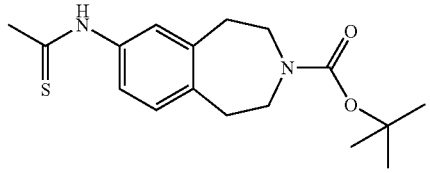

1,1-dimethylethyl-7-(acetylamino)-1,2,4,5-tetrahydro-3H-3-benzazepine-3-carboxylate (818 mg) and Lawesson's reagent (1.1 g) were combined in toluene (10 ml) and refluxed for 1.5 h. After cooling the reaction was worked up with ethyl acetate/NaHCO₃ (sat. sol.). The combined organic layers were concentrated and the residue was purified by flash chromatography over silica gel, eluting with 40% ethyl acetate in hexane, affording the title compound (411 mg).

MS (m/z): 321 [MH]+, 265 [M-56]+.

Preparation 46: 1,1-dimethylethyl 2-methyl-5,6,8,9-tetrahydro-7H-[1,3]thiazolo[4,5-h][3]benzazepine-7-carboxylate

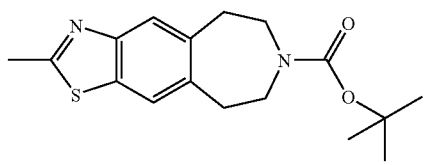

1,1-dimethylethyl 7-(ethanethioylamino)-1,2,4,5-tetrahydro-3H-3-benzazepine-3-carboxylate (411 mg), was dissolved in MeOH (12 ml), and 1N NaOH (6.1 ml) and added to potassium ferricyanide [K₃Fe(CN)₆] (2.1 g), in H₂O (12 ml). This mixture was warmed up to 60° C. for 1.5 h, cooled at rt. concentrated and the material thus obtained was purified by flash chromatography over silica gel, eluting with 20% ethyl acetate in hexane, affording a 2:1 mixture of title compound and its regioisomer (167 mg) that was further used as such.

MS (m/z): 321 [MH]+, 265 [M-56]+.

Preparation 47: 2-methyl-6,7,8,9-tetrahydro-5H-[1,3]thiazolo[4,5-h][3]benzazepine

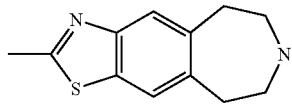

1,1-dimethylethyl-2-methyl-6,7,9,10-tetrahydro-8H-[1,3]thiazolo[5,4-g][3]benzazepine-8-carboxylate (167 mg), was dissolved in DCM (5 ml) and added to TFA (2 ml). The mixture was stirred at rt. for 1 h and then concentrated affording a 2:1 mixture of title compound and its regioisomer (139 mg) that was further used as such.

MS (m/z): 219 [MH]+

Preparation 48: 1,1-dimethylethyl 7-(propanoy-lamino)-1,2,4,5-tetrahydro-3H-3-benzazepine-3-carboxylate

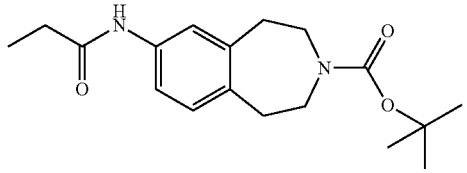

The title compound was prepared in analogy to Procedure 44 from 1,1-dimethylethyl 7-amino-1,2,4,5-tetrahydro-3H-3-benzazepine-3-carboxylate (1.5 g) in 1.26 g yield.

MS (m/z): 318 [MH]$^+$, 341 [M+Na]$^+$.

Preparation 49: 1,1-dimethylethyl 7-(propanethioy-lamino)-1,2,4,5-tetrahydro-3H-3-benzazepine-3-carboxylate

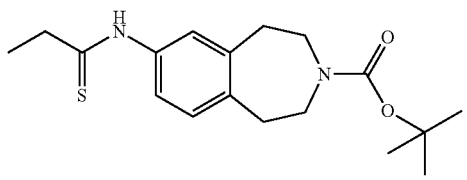

The title compound was prepared in analogy to Procedure 45 from 1,1-dimethylethyl 7-(propanoylamino)-1,2,4,5-tetrahydro-3H-3-benzazepine-3-carboxylate (1.26 mg) in 750 mg yield.

MS (m/z): 334 [MH]$^+$, 278 [M-56]$^+$.

Preparation 50: 1,1-dimethylethyl 2-ethyl-5,6,8,9-tetrahydro-7H-[1,3]thiazolo[4,5-h][3]benzazepine-7-carboxylate

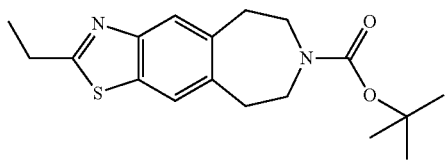

The title compound was prepared in analogy to Procedure 46 from 1,1-dimethylethyl 7-(propanethioylamino)-1,2,4,5-tetrahydro-3H-3-benzazepine-3-carboxylate (750 mg) and was obtained as a 2:1 mixture with its regioisomer in 653 mg yield that was further used as such.

MS (m/z): 332 [MH], 276 [M-56]$^+$.

Preparation 51: 2-ethyl-6,7,8,9-tetrahydro-5H-[1,3]thiazolo[4,5-h][3]benzazepine

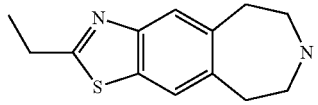

The title compound was prepared in analogy to Procedure 47 from 1,1-dimethylethyl 2-ethyl-5,6,8,9-tetrahydro-7H-[1,3]thiazolo[4,5-h][3]benzazepine-7-carboxylate (653 mg) and was obtained as a 2:1 mixture with its reigioisomer in 422 mg yield that was further used as such.

MS (m/z): 232 [MH]$^+$

Preparation 52: 1,1-dimethylethyl 6-bromo-7-hydroxy-8-nitro-1,2,4,5-tetrahydro-3H-3-benzazepine-3-carboxylate

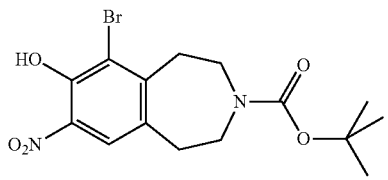

Bromination of 1,1-dimethylethyl 7-hydroxy-8-nitro-1,2,4,5-tetrahydro-3H-3-benzazepine-3-carboxylate (71 mg) was performed with NBS (41 mg) in DCM (2.2 ml) and SiO$_2$ (426 mg) at −15° C. under nitrogen. After 15 minutes SiO$_2$ was filtered off and the solvent was evaporated under reduced pressure. The crude was purified on silica gel (ethyl acetate/petroleum ether, 1/9) obtaining the title compound as a yellow solid (72 mg).

($^1$H-NMR, CDCl$_3$): 11.27 (s, 1H); 7.87 (s, 1H); 3.59 (m, 4H); 3.31 (m, 2H); 2.97 (m, 2H); 1.45 (s, 9H). MS (m/z): 388 [MH]$^+$.

Preparation 53: 1,1-dimethylethyl 8-amino-6-bromo-7-hydroxy-1,2,4,5-tetrahydro-3H-3-benzazepine-3-carboxylate

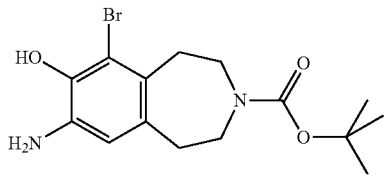

1,1-Dimethylethyl 6-bromo-7-hydroxy-8-nitro-1,2,4,5-tetrahydro-3H-3-benzazepine-3-carboxylate (200 mg) was reduced to 1,1-dimethylethyl 8-amino-6-bromo-7-hydroxy-1,2,4,5-tetrahydro-3H-3-benzazepine-3-carboxylate by hydrogenation (20 psi), in MeOH (5 ml) at room temperature for 45 min, using Ni/Raney as catalyst. The catalyst was filtered off and the solvent was evaporated under reduced pressure. The crude was purified on silica gel (ethyl acetate/petroleum ether, 1/1) obtaining the title compound (160 mg).

(¹H-NMR, CDCl₃): 6.48 (s, 1H); 3.52 (m, 4H); 3.04 (m, 2H); 2.79 (m, 2H); 1.93 (s br, 3H); 1.45 (s, 9H). MS (m/z): 358 [MH]⁺.

Preparation 54: 1,1-dimethylethyl 10-bromo-2-methyl-6,7,8,9-tetrahydro-5H-[1,3]oxazolo[4,5-h][3]-benzazepine-7-carboxylate

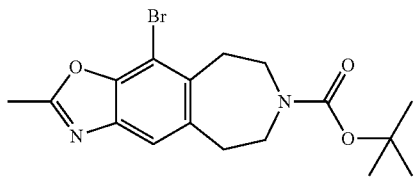

1,1-Dimethylethyl 8-amino-6-bromo-7-hydroxy-1,2,4,5-tetrahydro-3H-3-benzazepine-3-carboxylate (1.604 g) was treated with trimethyl orthoacetate (0.856 ml) and pyridinium p-toluenesulfonate (112 mg) in dry DMF (23 ml) at 60° C. for 1.5 hours. Volatiles were evaporated under reduced pressure and the residue was purified on silica gel (ethyl acetate/petroleum ether: 1/6) providing the title compound as white solid (1.553 g, 90% yield).

(¹H-NMR, MeOD): 7.36 (s, 1H); 3.58 (dd, 4H); 3.25 (dd, 2H); 3.07 (dd, 2H); 2.62 (s, 3H); 1.32 (s br, 9H). MS (m/z): 382 [MH]⁺.

Preparation 55: 10-bromo-2-methyl-6,7,8,9-tetrahydro-5H-[1,3]oxazolo[4,5-h][3]benzazepine

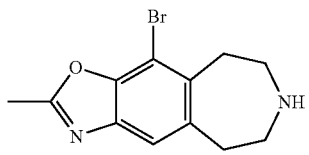

To a stirred solution of 1,1-dimethylethyl 10-bromo-2-methyl-6,7,8,9-tetrahydro-5H-[1,3]oxazolo[4,5-h][3]benzazepine-7-carboxylate (71 mg) in DCM (2.1 ml) TFA (0.9 ml) was added dropwise. After 30 min. the mixture was diluted with DCM and washed with 5% K₂CO₃. The organic phase was dried (Na₂SO₄) and concentrated to afford the title compound (52 mg).

MS (m/z): 282 [MH]⁺.

Preparation 56: 1,1-dimethylethyl 10-bromo-2-ethyl-6,7,8,9-tetrahydro-5H-[1,3]oxazolo[4,5-h][3]benzazepine-7-carboxylate

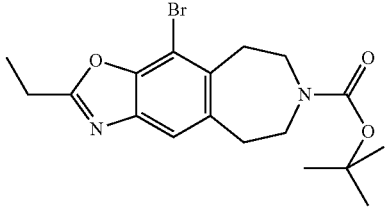

The title compound was prepared in analogy to Procedure 54 from 1,1-dimethylethyl 8-amino-6-bromo-7-hydroxy-1,2,4,5-tetrahydro-3H-3-benzazepine-3-carboxylate (1.4 g) and was obtained as a colourless oil (1.532 mg, 98% yield).

(¹H-NMR, MeOD): 7.38 (s, 1H); 3.58 (dd, 4H); 3.26 (dd, 2H); 3.08 (dd, 2H); 2.97 (q, 2H); 1.41 (t, 3H); 1.32 (s br, 9H). MS (m/z): 396 [MH]⁺.

Preparation 57: 10-bromo-2-ethyl-6,7,8,9-tetrahydro-5H-[1,3]oxazolo[4,5-h][3]benzazepine

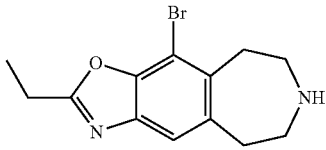

The title compound was prepared in analogy to Procedure 55 from 1,1-dimethylethyl 10-bromo-2-ethyl-6,7,8,9-tetrahydro-5H-[1,3]oxazolo[4,5-h][3]benzazepine-7-carboxylate (600 mg) in 447 mg yield.

MS (m/z): 296 [MH]⁺.

Preparation 58: 10-bromo-2-(trifluoromethyl)-6,7,8,9-tetrahydro-5H-[1,3]oxazolo[4,5-h][3]benzazepine

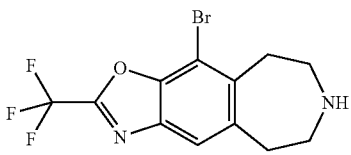

1,1-Dimethylethyl 8-amino-6-bromo-7-hydroxy-1,2,4,5-tetrahydro-3H-3-benzazepine-3-carboxylate (1.6 g) was reacted with trifluoroacetic anhydride (0.775 ml) and pyridine (0.542 ml) in DCM (32 ml) at 0° C. for 20 minutes. The solvent was evaporated, the residue was dissolved in Et₂O and washed with water and brine. The organic phase was dried (Na₂SO₄) and concentrated to give the corresponding trifluoroacetamide (2.005 g). This intermediate was treated without any purification with PPA (6 g) at 120° C. for 30 min, the mixture was basified with 5% NaHCO₃ and extracted with DCM. The organic phase was dried (Na₂SO₄) and concentrated. The residue was purified on silica gel (DCM/MeOH/ conc.NH₄OH, 100/4/0.4) affording the title compound as a grey solid (1.093 g, 72% yield).

(¹H-NMR, MeOD): 7.61 (s, 1H); 3.37 (m, 2H); 3.16 (m, 2H); 2.98-2.88 (m, 4H). MS (m/z): 336 [MH]⁺.

Preparation 59: 5-{5-[(4-chlorobutyl)thio]-4-methyl-4H-1,2,4-triazol-3-yl}-2-methylquinoline

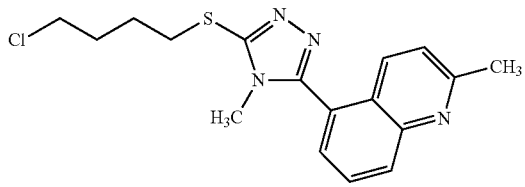

4-Methyl-5-(2-methyl-5-quinolinyl)-2,4-dihydro-3H-1,2,4-triazole-3-thione (400 mg) was reacted with 1-bromo-4-chloro-butane (0.233 ml) and NaH (60%, 69 mg) in absolute EtOH (6.5 ml) at reflux for 45 min. Ethyl acetate was added, the insoluble salts were filtered off and the solvent was evaporated under reduced pressure. The crude was purified on silica gel (eluent: ethyl acetate to ethyl acetate/acetone, 1/1) affording the desired compound as pale yellow solid (430 mg, 79% yield).

(¹H-NMR, CDCl₃): 8.32-8.16 (m, 2H); 7.81 (dd, 1H); 7.58 (dd, 1H); 7.35 (d, 1H); 3.62 (t, 2H); 3.42 (s, 3H); 3.41 (t, 2H); 2.81 (s, 3H); 2.12-1.94 (m, 4H). MS (m/z): 347 [MH]⁺.

Preparation 60: N-(2,2-Dimethoxy-ethyl)-2-(3-methoxy-2-methyl-phenyl)-acetamide

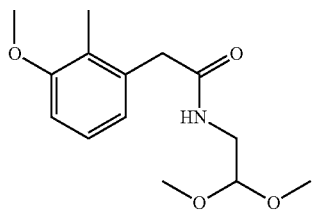

To a stirred solution of (3-methoxy-2-methyl-phenyl)-acetic acid (18.2 g, Tetrahedron Letters, 1980, Vol. 21, 3309-3312) in DCM (500 ml) and DMF (5 ml) at room temperature, oxalyl dichloride (19.7 ml) was added dropwise.

After 3 hours volatiles were evaporated under reduced pressure, the residue was dissolved in DCM (100 ml) and added dropwise to a stirred solution of 2,2-dimethoxy-ethylamine (10.67 g, 1 eq) and triethylamine (16 ml, 1.1 eq) in DCM (400 ml) at room temperature. After 24 hours the mixture was washed with water, 10% acetic acid, sat. NaHCO₃ and brine. The organic phase was dried (Na₂SO₄) and concentrated to afford 25 g of desired product (92% yield).

MS (m/z): 268 [MH]⁺.

Preparation 61: 8-methoxy-9-methyl-1,3-dihydro-benzo[d]azepin-2-one

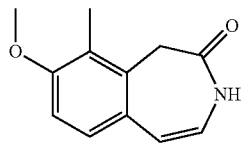

A solution of N-(2,2-dimethoxy-ethyl)-2-(3-methoxy-2-methyl-phenyl)-acetamide (23 g) in a mixture of acetic acid (40 ml) and conc. HCl (40 ml) was stirred at room temperature for 24 hours. Ice was added with vigorous stirring and the obtained precipitated was filtered (10.9 g, 62% yield).

MS (m/z): 204 [MH]⁺.

Preparation 62: 8-methoxy-9-methyl-1,3,4,5-tetrahydro-benzo[d]azepin-2-one

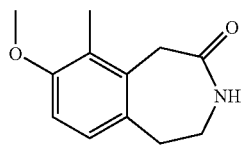

8-Methoxy-9-methyl-1,3-dihydro-benzo[d]azepin-2-one (10.9 g) was reduced to 8-methoxy-9-methyl-1,3,4,5-tetrahydro-benzo[d]azepin-2-one by hydrogenation in AcOH (at room temperature, 40 psi), using 10% Pd/c (1.3 g) as catalyst. The catalyst was filtered off and the solvent was evaporated under reduced pressure affording the desired product (11 g, quantitative yield).

MS (m/z): 206 [MH]⁺.

Preparation 63: 7-methoxy-6-methyl-2,3,4,5-tetrahydro-1H-benzo[d]azepine

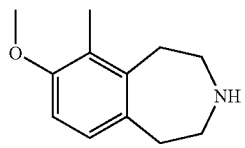

To a stirred mixture of 8-methoxy-9-methyl-1,3,4,5-tetrahydro-benzo[d]azepin-2-one (4 g) in toluene at 5° C., under nitrogen atmosphere, borane dimethylsulfide (3 ml) was added dropwise. The mixture was refluxed for 3 hours. After cooling to room temperature 40 ml of 10% HCl (40 ml) were added and the mixture was refluxed for 3 hours.

After cooling to room temperature the mixture was diluted with water and washed with ethyl ether. The aqueous phase was basified with 10% NaOH and extracted with DCM. The organic phase was dried (Na₂SO₄) and concentrated to afford the desired compound (1.3 g, 32% yield).

MS (m/z): 192 [MH]⁺.

Preparation 64: 1,1-dimethylethyl 7-hydroxy-6-methyl-1,2,4,5-tetrahydro-3H-3-benzazepine-3-carboxylate

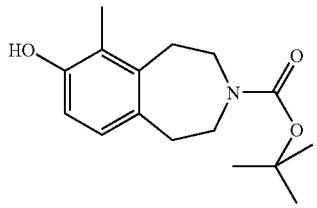

7-Methoxy-6-methyl-2,3,4,5-tetrahydro-1H-benzo[d]azepine hydrochloride (8.6 g) was treated with 48% HBr (100 ml) at 110° C. for 4 hours; volatiles were evaporated under reduced pressure obtaining crude 7-hydroxy-6-methyl-1,2,4,5-tetrahydro-3H-3-benzazepine hydrobromide (10.2 g).

Di-tert-butyl dicarbonate (11.2 g, 1.35 eq) was added to a stirred solution of the crude 7-hydroxy-6-methyl-1,2,4,5-tetrahydro-3H-3-benzazepine hydrobromide and triethylamine (12.7 ml, 2.4 eq) in THF (200 ml) at room temperature. After 3 hours the solvent was evaporated and the residue was dissolved in ethyl ether and 5% citric acid; the organic phase was separated, washed with sat. NaCl, dried (Na$_2$SO$_4$) and concentrated. The residue was purified on silica gel (ethyl acetate/petroleum ether: 2/8) obtaining the desired product (9.0 g, 86% yield).

($^1$H-NMR, CDCl$_3$): 6.82 (d, 1H); 6.55 (d, 1H); 4.75 (s br, 1H); 3.54 (m, 4H); 2.92 (m, 2H); 2.83 (m, 2H); 2.21 (s, 3H); 1.45 (s, 9H). MS (m/z): 278 [MH]$^+$.

Preparation 65: 1,1-dimethylethyl 7-hydroxy-6-methyl-8-nitro-1,2,4,5-tetrahydro-3H-3-benzazepine-3-carboxylate

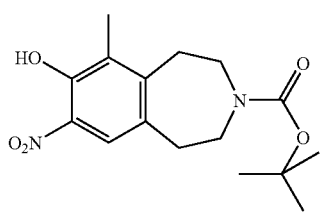

Nitric acid (65%, 0.370 ml) was added dropwise with vigorous stirring to 1,1-dimethylethyl 7-hydroxy-6-methyl-1,2,4,5-tetrahydro-3H-3-benzazepine-3-carboxylate (600 mg) and silica gel (1.67 g) in DCM (5.7 ml) at −15° C. After 30 min a mixture of DCM/MeOH/conc.NH$_4$OH: 10/3/1.5 was added and silica gel was filtered off. The solvent was evaporated under reduced pressure and the residue was purified on silica gel (ethyl acetate/petroleum ether: 15/85) obtaining the desired compound (470 mg, 67% yield).

($^1$H-NMR, CDCl$_3$): 11.06 (s, 1H); 7.74 (s, 1H); 3.56 (m, 4H); 2.99 (m, 2H); 2.90 (m, 2H); 2.29 (s, 3H); 1.44 (s, 9H). MS (m/z): 323 [MH]$^+$.

Preparation 66: 1,1-dimethylethyl 8-amino-7-hydroxy-6-methyl-1,2,4,5-tetrahydro-3H-3-benzazepine-3-carboxylate

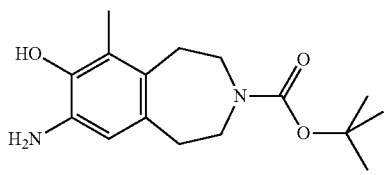

The title compound was prepared in analogy to the Preparation 53 from 1,1-dimethylethyl 7-hydroxy-6-methyl-8-nitro-1,2,4,5-tetrahydro-3H-3-benzazepine-3-carboxylate (4.59 g) in 3.99 g yield.

($^1$H-NMR, CDCl$_3$): 6.50 (s, 1H); 3.50 (m, 4H); 3.23 (s br, 3H); 2.89-2.69 (m, 4H); 2.19 (s, 3H); 1.45 (s, 9H). MS (m/z): 293 [MH]$^+$.

Preparation 67: 1,1-dimethylethyl 2,10-dimethyl-5,6,8,9-tetrahydro-7H-[1,3]oxazolo[4,5-h][3]benzazepine-7-carboxylate

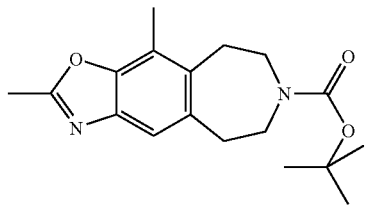

1,1-Dimethylethyl 8-amino-7-hydroxy-6-methyl-1,2,4,5-tetrahydro-3H-3-benzazepine-3-carboxylate (1.1 g) was treated with trimethyl orthoacetate (0.718 ml) and pyridinium p-toluenesulfonate (94 mg) in dry DMF (19 ml) at 60° C. for 1.5 hours. Volatiles were evaporated under reduced pressure and the residue was purified on silica gel (ethyl acetate/petroleum ether: 1/4) providing the title compound as white solid (1.127 g, 94% yield).

($^1$H-NMR, MeOD): 7.21 (s, 1H); 3.56 (dd, 4H); 3.01 (m, 4H); 2.59 (s, 3H); 2.46 (s, 3H); 1.32 (s, 9H). MS (m/z): 317 [MH]$^+$.

Preparation 68: 2,10-dimethyl-5,6,8,9-tetrahydro-7H-[1,3]oxazolo[4,5-h][3]benzazepine-7

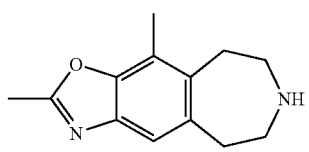

The title compound was prepared in analogy to Preparation 55 from 1,1-dimethylethyl 2,10-dimethyl-5,6,8,9-tetrahydro-7H-[1,3]oxazolo[4,5-h][3]benzazepine-7-carboxylate (500 mg) in 340 mg yield.

MS (m/z): 217 [MH]$^+$.

Preparation 69: 1,1-dimethylethyl 2-ethyl-10-methyl-5,6,8,9-tetrahydro-7H-[1,3]oxazolo[4,5-h][3]benzazepine-7-carboxylate

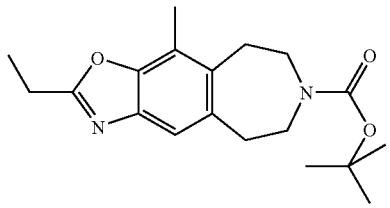

1,1-Dimethylethyl 8-amino-7-hydroxy-6-methyl-1,2,4,5-tetrahydro-3H-3-benzazepine-3-carboxylate (1.1 g) was treated with trimethyl orthopropionate (0.802 ml) and pyridinium p-toluenesulfonate (0.1 eq) in dry DMF (19 ml) at 60° C. for 1.5 hours. Volatiles were evaporated under reduced pressure and the residue was purified on silica gel (ethyl acetate/petroleum ether: 1/4) providing the title compound as white solid (1.18 g, 95% yield).
(¹H-NMR, MeOD): 7.23 (s, 1H); 3.55 (dd, 4H); 3.01 (m, 4H); 2.94 (q, 2H); 2.46 (s, 3H); 1.40 (t, 3H); 1.32 (s, 9H). MS (m/z): 331 [MH]⁺.

Preparation 70: 2-ethyl-10-methyl-5,6,8,9-tetrahydro-7H-[1,3]oxazolo[4,5-h][3]benzazepine

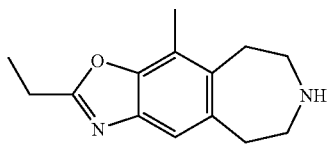

The title compound was prepared in analogy to Preparation 55 from 1,1-dimethylethyl 2-ethyl-10-methyl-5,6,8,9-tetrahydro-7H-[1,3]oxazolo[4,5-h][3]benzazepine-7-carboxylate (500 mg) in 345 mg yield.
MS (m/z): 231 [MH]⁺.

Preparation 71: 10-methyl-2-(trifluoromethyl)-6,7,8,9-tetrahydro-5H-[1,3]oxazolo[4,5-h][3]benzazepine

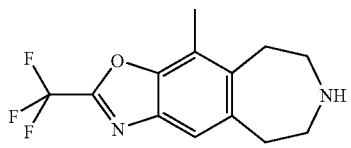

1,1-Dimethylethyl 8-amino-7-hydroxy-6-methyl-1,2,4,5-tetrahydro-3H-3-benzazepine-3-carboxylate (1.766 g) was reacted with trifluoroacetic anhydride (1.046 ml) and pyridine (0.731 ml) in dry DCM (43 ml) at 0° C. for 20 minutes. The solvent was evaporated, the residue was dissolved in Et₂O and washed with water and brine. The organic phase was dried (Na₂SO₄) and concentrated to give the corresponding trifluoroacetamide (2.350 g, quantitative yield). This intermediate was treated without any purification with PPA (8 g) at 120° C. for 30 min, the mixture was basified with 5% NaHCO₃ and extracted with DCM. The organic phase was dried (Na₂SO₄) and concentrated. The residue was purified on silica gel (DCM/MeOH/conc.NH₄OH: 100/6/0.6) affording the title compound as grey solid (963 mg, 59% yield).
(¹H-NMR, MeOD): 7.46 (s, 1H); 3.12 (m, 4H); 2.94 (m, 4H); 2.51 (s, 3H). MS (m/z): 271 [MH]⁻.

Preparation 72: 3-[10-bromo-2-(trifluoromethyl)-5,6,8,9-tetrahydro-7H-[1,3]oxazolo[4,5-h][3]benzazepin-7-yl]-1-butanol

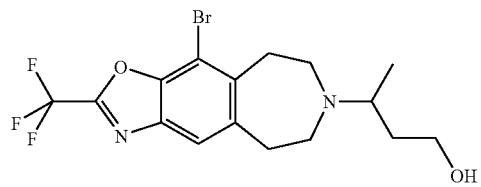

A mixture of 10-bromo-2-(trifluoromethyl)-6,7,8,9-tetrahydro-5H-[1,3]oxazolo[4,5-h][3]benzazepine (250 mg, 1 eq), 4-hydroxy-butan-2-one (0.077 ml, 1.2 eq), acetic acid (0.042 ml, 1 eq) and sodium triacetoxyborohydride (314 mg, 2 eq) in THF (2.5 ml) was stirred at room temperature for 20 hours. Additional 4-hydroxy-butan-2-one (0.24 eq) and sodium triacetoxyborohydride (0.4 eq) were added and the mixture was stirred for 5 hours. Then, the mixture was diluted with DCM and washed with 5% NaHCO₃ and brine. The organic phase was dried (Na₂SO₄) and concentrated. The crude was purified on silica gel (DCM/MeOH/conc.NH₄OH, 100/2.5/0.25) providing the title compound (218 mg, 72% yield).
MS (m/z): 408 [MH]⁺.

Preparation 73: 3-{10-bromo-2-methyl-6,7,8,9-tetrahydro-5H-[1,3]oxazolo[4,5-h][3]benzazepine}-butan-1-ol

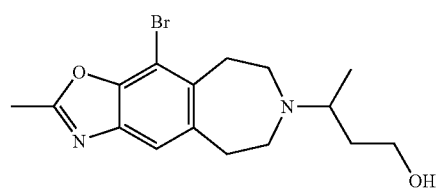

10-Bromo-2-methyl-6,7,8,9-tetrahydro-5H-[1,3]oxazolo[4,5-h][3]benzazepine (200 mg) was reacted with 4-hydroxy-butan-2-one in according to Preparation 72 to give the title compound (167 mg, 66% yield; purification on silica gel, eluent: DCM/MeOH/conc.NH₄OH, 100/3/0.3)
MS (m/z): 354 [MH]⁺..

Preparation 74: 3-{10-bromo-2-ethyl-6,7,8,9-tetrahydro-5H-[1,3]oxazolo[4,5-h][3]benzazepine}-butan-1-ol

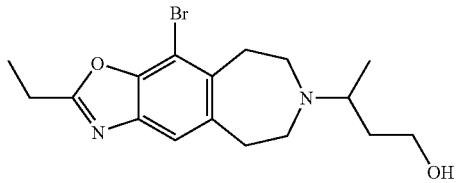

10-Bromo-2-ethyl-6,7,8,9-tetrahydro-5H-[1,3]oxazolo[4,5-h][3]benzazepine (257 mg) was reacted with 4-hydroxy-butan-2-one according to Preparation 72 to give the title compound (211 mg, 65% yield; purification on silica gel, eluent: DCM/MeOH/NH$_4$OH, 100/3/0.3).

MS (m/z): 368 [MH]$^+$.

Preparation 75: 3-{10-methyl-2-(trifluoromethyl)-6,7,8,9-tetrahydro-5H-[1,3]oxazolo[4,5-h][3]benzazepine}-butan-1-ol

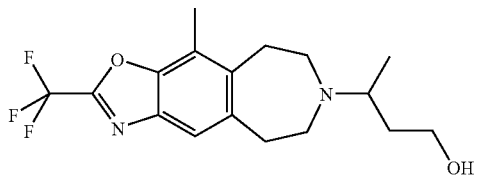

10-Methyl-2-(trifluoromethyl)-6,7,8,9-tetrahydro-5H-[1,3]oxazolo[4,5-h][3]benzazepine (250 mg) was reacted with 4-hydroxy-butan-2-one according to Preparation 72 to give the title compound (253 mg, 80% yield; purification on silica gel, eluent: DCM/MeOH/NH$_4$OH, 100/2.5/0.25).

MS (m/z): 343 [MH]$^+$.

Preparation 76: 1,5-dihydro-benzo[d]azepine-2,4-dione

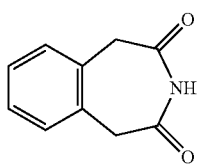

4-Bromo-1H-benzo[d]azepin-2-ylamine hydrobromide (41.2 g) was dissolved in 600 ml of H$_2$O that was previously heated to 85° C. Sodium acetate trihydrate (18.5 g) was added portion wise and the solution was heated to 90° C. for 3 h. Cooling to room temperature caused the precipitation of a white solid that was filtered-off, washed with water and desiccated under reduced pressure to afford the title compound (20.4 g, 90% yield)

MS (m/z): 176 [MH]$^+$..

Preparation 77: 2,3,4,5-tetrahydro-1H-benzo[d]azepine hydrochloride

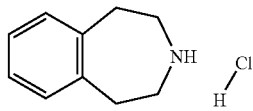

To a suspension of 1,5-dihydro-benzo[d]azepine-2,4-dione (9.3 g) in toluene (250 ml) borane-methylsulfide complex (20 ml) was added dropwise under nitrogen atmosphere, then the mixture was heated at reflux for 4 h. MeOH (20 ml) was added dropwise and the mixture refluxed for additional 1 h, then cooled to room temperature. A 10% solution of anidrous HCl in ethyl ether (50 ml) was added and the solid precipitate was filtered off, washed with ethyl ether and desiccated under reduced pressure to afford the title compound as a white solid (7.6 g, 78% yield).

MS (m/z): 148 [MH]$^+$.

Preparation 78: 1-(1,2,4,5-tetrahydrobenzo[d]azepin-3-yl)ethanone

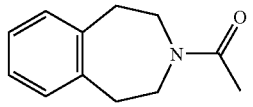

To a solution of 2,3,4,5-Tetrahydro-1H-benzo[d]azepine hydrochloride (7.0 g) in DCM (200 ml) Et$_3$N (12.1 ml, 2.5 eq) was added followed by a dropwise addition of acetic anhydride (4 ml). After 2 h the mixture was washed in sequence with 1N HCl, 5% aqueous NaHCO$_3$ and brine, then dried over Na$_2$SO$_4$ and concentrated to afford a white solid (6.9 g, 95% yield).

MS (m/z): 190 [MH]$^+$.

Preparation 79: 1-(7-nitro-1,2,4,5-tetrahydrobenzo[d]azepin-3-yl)ethanone

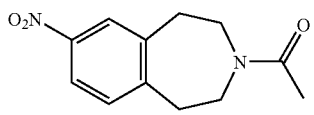

1-(1,2,4,5-Tetrahydrobenzo[d]azepin-3-yl)ethanone (3.8 g) was dissolved in a 2:1 mixture of acetic acid and 96% sulphuric acid (15 ml), then the mixture was cooled to 0° C. and a 3:2 mixture of 65% nitric acid and 96% sulphuric acid (2.5 ml) was added dropwise, while the temperature was maintained below 5° C. The mixture was stirred for additional 30 min, then poured into crushed ice (300 g) and extracted with ethyl acetate. The organic phase was washed with 5% aqueous NaHCO$_3$, dried over Na$_2$SO$_4$ and concentrated to afford a crude material (4.3 g). Filtration through a silica gel pad (DCM/MeOH, 98/2) yielded the title compound as a yellow solid (4.0 g, 85% yield)

MS (m/z): 235 [MH]$^+$..

Preparation 80:1-(7-amino-1,2,4,5-tetrahydrobenzo[d]azepin-3-yl)ethanone

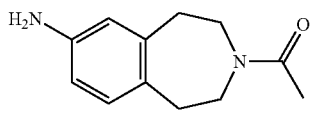

To a solution of 1-(7-nitro-1,2,4,5-tetrahydrobenzo[d]azepin-3-yl)ethanone (4.0 g) in ethanol (120 ml) 10% Pd/C was added (150 mg) and the mixture hydrogenated for 1 h under a pressure of 30 psi of $H_2$. The mixture was filtered through a celite pad and concentrated to afford a white solid (3.15 g, 90% yield).

MS (m/z): 205 [MH].

Preparation 81: 1-(7-cyano-1,2,4,5-tetrahydrobenzo[d]azepin-3-yl)ethanone

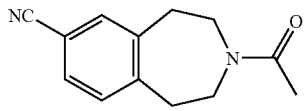

$NaNO_2$ (0.53 g, 1.05 eq) was added portion wise to a solution of 1-(7-amino-1,2,4,5-tetrahydrobenzo[d]azepin-3-yl)ethanone (1.5 g, 1 eq) in 1.5 M $H_2SO_4$ (10 mL) maintained to 0° C. The obtained solution was added drop wise to a solution of CuCN (0.8 g, 1.23 eq) and NaCN (1.25 g, 3.42 eq) in $H_2O$ (5 ml), then the reaction mixture was allowed to warm to room temperature and extracted with ethyl acetate. The organic solution was washed with 5% aqueous $NaHCO_3$ and brine, then dried over $Na_2SO_4$ and concentrated to afford a crude material (1.5 g). Chromatography over silica gel (ethyl acetate/MeOH: 9/1) yielded the title compound as a pale orange solid (1.0 g, 63% yield).

MS (m/z): 215 [MH]$^+$.

Preparation 82: 3-{[(1,1-dimethylethyl)oxy]carbonyl}-2,3,4,5-tetrahydro-1H-3-benzazepine-7-carboxylic acid

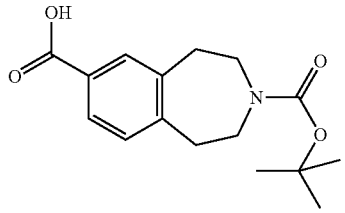

1-(7-Cyano-1,2,4,5-tetrahydrobenzo[d]azepin-3-yl)ethanone (0.9 g, 1 eq) was suspended in 10 ml of a 1:1 mixture of 30% aqueous NaOH and ethanol. The mixture was heated at reflux for 18 h, then cooled, neutralized with 6 N HCl and concentrated to afford a solid residue. The solid was treated with MeOH and insoluble materials were filtered off. The solution was concentrated to yield a solid residue that was dissolved in aqueous 1% NaOH (20 ml, 1.2 eq), then a solution of diterbutyl dicarbonate (1 g, 1.07 eq) in 1,4-dioxane was added drop wise and the mixture stirred for 12 h. The mixture was made acidic (pH 2) with 2 N HCl, and extracted with ethyl acetate. The organic layer was washed with 5% aqueous $NaHCO_3$ and brine, then dried over $Na_2SO_4$ and concentrated to afford a crude material (0.9 g). Chromatography over silica gel (ethyl acetate/hexane/MeOH: 48/48/4) yielded the title compound as a white solid (0.8 g, 65% yield).

MS (m/z): 292 [MH]$^+$.

Preparation 83: 1,1-dimethylethyl 7-{[[(1-methylethyl)amino]carbonyl}-1,2,4,5-tetrahydro-3H-3-benzazepine-3-carboxylate

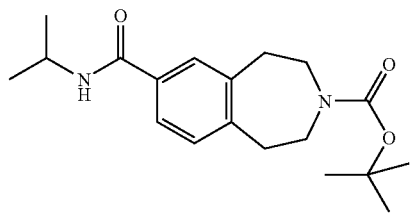

A solution of 3-{[(1,1-dimethylethyl)oxy]carbonyl}-2,3,4,5-tetrahydro-1H-3-benzazepine-7-carboxylic acid (0.4 g) and CDI (0.23 g) in THF (5 ml) was stirred for 1 h under nitrogen atmosphere, then isopropylamine (0.3 ml) was added and the mixture stirred overnight. After removal of THF, the residue was dissolved in ethyl acetate and the solution washed with 1 N HCl, 5% aqueous $NaHCO_3$ and brine, then dried over $Na_2SO_4$ and concentrated to afford a white solid (0.4 g, 89% yield).

MS (m/z): 333 [MH]$^+$.

Preparation 84: 1,1-dimethylethyl 1-hydroxy-2-(1-methylethyl)-3-oxo-2,3,5,6,8,9-hexahydroazepino[4,5-f]isoindole-7(1-H)-carboxylate

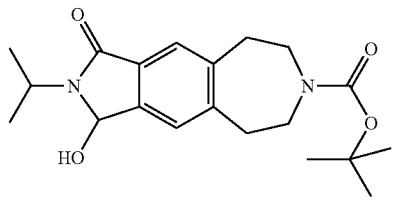

To a solution of 1,1-dimethylethyl 7-{[(1-methylethyl)amino]carbonyl}-1,2,4,5-tetrahydro-3H-3-benzazepine-3-carboxylate (0.95 g, 1 eq) in THF (50 ml), cooled to −78° C. under nitrogen atmosphere, t-BuLi (1.7 M pentane solution, 3.7 ml) was added over a 20 min period, then the mixture was allowed to warm to −40° C. and stirred for 1 h at that temperature. Anhydrous DMF (0.27 ml) was added dropwise, then the mixture was allowed to warm to room temperature and quenched with a saturated aqueous solution of $NH_4Cl$ (5 ml). After removal of THF, the residue was dissolved in ethyl acetate and the solution washed with 1 N HCl, 5% aqueous $NaHCO_3$ and brine, then dried over $Na_2SO_4$ and concentrated to afford a white solid (1.0 g, 97% yield).

MS (m/z): 361 [MH]$^+$.

Preparation 85: 2-(1-methylethyl)-3,5,6,7,8,9-hexahydroazepino[4,5-f]isoindol-1(2H-one

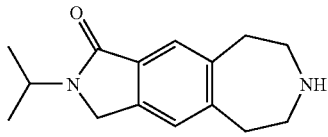

To a solution of 1,1-dimethylethyl 1-hydroxy-2-(1-methylethyl)-3-oxo-2,3,5,6,8,9-hexahydroazepino[4,5-f]isoindole-7(1H)-carboxylate (1.0 g) and triethylsilane (0.95 ml) in DCM (20 ml), at 0° C., TFA (10 ml) was added dropwise and the mixture stirred for 1 h. the mixture was neutralized with 2M aqueous $Na_2CO_3$ and washed with ether discarding the organic layer. Then the aqueous layer was made basic with NaOH and extracted with DCM. The organic solution was washed with brine, dried over $Na_2SO_4$ and concentrated to afford a pale yellow solid (0.6 g, 88% yield).

MS (m/z): 245 [MH]$^+$.

General Procedure 1: N-alkylation and Salt Formation

A mixture of the secondary amine (1 eq.), the primary chloroalkyl derivative (1.2 eq.), sodium iodide (1 eq.), potassium carbonate (1.2 eq.) in dry DMF (2 ml per mmol secondary amine) was stirred under vacuum to remove traces of humidity and undesired solvent residues, then purged with dry nitrogen. The mixture was stirred at 60° C. for 24 h. After elimination of the solvent under reduced pressure the residue was partitioned between aqueous $Na_2CO_3$ (0.5 M) and DCM. The organic layer was collected and the aqueous phase extracted twice with DCM. The combined DCM layers were concentrated and submitted to column chromatography to provide the free base of the target compounds. To a solution of this material in DCM (ca. 20 ml per mmol) was added HCl in $Et_2O$ (1.0 eq. with respect to free base), the solvent evaporated under reduced pressure and the material thus obtained was triturated with 1:1 $Et_2O$:EtOAc (ca. 10 ml per mmol) to give the target compounds as hydrochloride salts.

General Procedure 2: Synthesis of 2-substituted 6,7,8,9-tetrahydro-5H-[1,3]oxazolo[4,5-h][3]benzazepines A mixture of 1,1-dimethylethyl 7-amino-8-hydroxy-1,2,4,5-tetrahydro-3H-3-benzazepine-3-carboxylate (1 eq.), a carboxylic acid chloride derivative (1.1 eq.), and pyridine (1.1 eq.), in chlorobenzene (2 ml per mmol of benzazepine derivative) was stirred at 90° C. for 4 h. Solvent was removed under vacuum, the residue dissolved in DCM (2 ml per mmol of benzazepine derivative) and trifluoroacetic acid (10 eq.) was added at room temperature. The reaction mixture was stirred until complete deprotection (4-16 h). Solvent was removed under reduced pressure, the residue was dissolved in chlorobenzene (4 ml per mmol of benzazepine derivative) and stirred at 120° C. for 8 h. The reaction mixture was cooled to room temperature, solvent was removed under vacuum, the residue was partitioned between aqueous saturated $NaHCO_3$ and DCM. The organic layer was collected and the aqueous phase extracted twice with DCM. The combined DCM layers were concentrated and submitted to column chromatography to provide the free base of the target compounds which were used in further conversions.

EXAMPLE 1

2-Methyl-7-(3-{[4-methyl-5-(2-methyl-5-quinolinyl)-4H-1,2,4-triazol-3-yl]thio}propyl)-6,7,8,9-tetrahydro-5H-[1,3]oxazolo[4,5-h][3]benzazepine hydrochloride

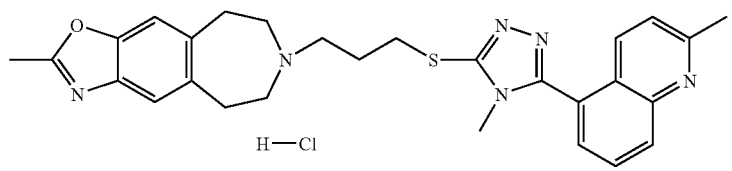

The title compound was prepared in analogy to General Procedure 1 from 2-methyl-6,7,8,9-tetrahydro-5H-[1,3]oxazolo[4,5-h][3]benzazepine (0.82 mmol) and 5-{5-[(3-chloropropyl)thio]-4-methyl-4H-1,2,4-triazol-3-yl}-2-methylquinoline and was obtained as a faint yellow slightly hygroscopic solid (0.46 mmol).

NMR ($^1$H, $CD_3OD$): δ 8.24 (d, 2H), 7.99 (t, 1H), 7.82 (d, 1H), 7.59 (d, 1H), 7.54 (s, 1H), 7.52 (s, 1H), 3.91 (m, 2H), 3.55 (s, 3H), 3.35 (m, 6H), 3.3 (m, 2H), 3.17 (m, 2H), 2.82 (s, 3H), 2.65 (s, 3H), 2.42 (m, 2H), acidic proton not observed. MS (m/z): 499 [MH]$^+$.

EXAMPLE 2

7-(3-{[4-Methyl-5-(2-methyl-5-quinolinyl)-4H-1,2,4-triazol-3-yl]thio}propyl)-6,7,8,9-tetrahydro-5H-[1,3]oxazolo[4,5-h][3]benzazepine hydrochloride

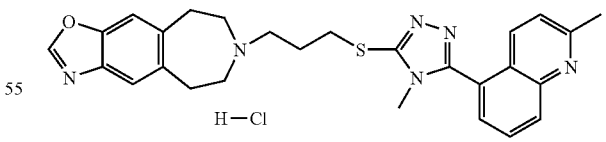

The title compound was prepared in analogy to General Procedure 1 from 6,7,8,9-tetrahydro-5H-[1,3]oxazolo[4,5-h][3]benzazepine (0.10 mmol) and 5-{5-[(3-chloropropyl)thio]-4-methyl-4H-1,2,4-triazol-3-yl}-2-methylquinoline and was obtained as a colourless slightly hygroscopic solid (15 μmol)

NMR ($^1$H, $CD_3OD$): δ 8.48 (s, 1H), 8.23 (d, 1H), 8.17 (d, 1H), 7.95 (dd, 1H), 7.79 (dd, 1H), 7.66 (s, 1H), 7.62 (s, 1H), 7.54 (d, 1H), 3.54 (s, 3H), 3.2-3.4 (m, 12H), 2.79 (s, 3H), 2.38 (m, 2H), acidic proton not observed. MS (m/z): 485 [MH]+.

EXAMPLE 3

2-(1-Methylethyl)-7-(3-{[4-methyl-5-(4-methyl-1,3-oxazol-5-yl)-4H-1,2,4-triazol-3-yl]thio}propyl)-6,7,8,9-tetrahydro-5H-[1,3]oxazolo[4,5-h][3]benzazepine hydrochloride

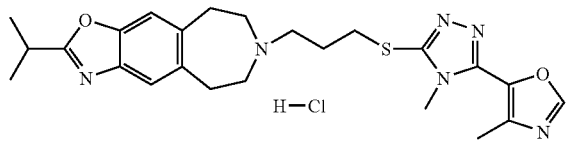

The title compound was prepared in analogy to General Procedure 1 from 2-(1-methylethyl)-6,7,8,9-tetrahydro-5H-[1,3]oxazolo[4,5-h][3]benzazepine (0.21 mmol) and 3-[(3-chloropropyl)thio]-4-methyl-5-(4-methyl-1,3-oxazol-5-yl)-4H-1,2,4-triazole and was obtained as a colourless slightly hygroscopic solid (78 μmol).

NMR (1H, CD3OD): δ 8.41 (d, 1H), 7.55 (2s, 2H), 3.85-3.90 (m, 2H), 3.83 (s, 3H), 3.2-3.4 (m, 11H), 2.47 (s, 3H), 2.3 (m, 2H), 1.47 (d, 6H), acidic proton not observed. MS (m/z): 467 [MH]+.

EXAMPLE 4

2-(1-Methylethyl)-7-(3-{[4-methyl-5-(2-methyl-5-quinolinyl)-4H-1,2,4-triazol-3-yl]thio}propyl)-6,7,8,9-tetrahydro-5H-[1,3]oxazolo[4,5-h][3]benzazepine hydrochloride

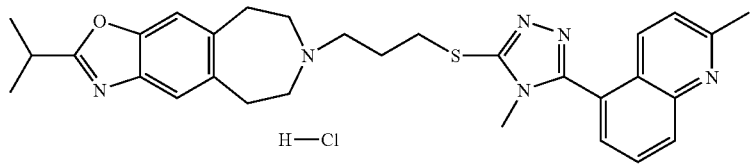

The title compound was prepared in analogy to General Procedure 1 from 2-(1-methylethyl)-6,7,8,9-tetrahydro-5H-[1,3]oxazolo[4,5-h][3]benzazepine (0.21 mmol) and 5 {5-[(3-chloropropyl)thio]-4-methyl-4H-1,2,4-triazol-3-yl}-2-methylquinoline and was obtained as a white slightly hygroscopic solid (73 μmol).

NMR (1H, CD3OD): δ 8.24 (d, 1H), 8.17 (d, 1H), 7.95 (t, 1H), 7.8 (d, 1H), 7.53-7.57 (m, 3H), 3.54 (s, 3H), 3.2-3.4 (m, 13H), 2.79 (s, 3H), 2.41 (m, 2H), 1.47 (d, 6H), acidic proton not observed. MS (m/z): 527 [MH]+.

EXAMPLE 5

2-(1,1-Dimethylethyl)-7-(3-{[4-methyl-5-(2-methyl-5-quinolinyl)-4H-1,2,4-triazol-3-yl]thio}propyl)-6,7,8,9-tetrahydro-5H-[1,3]oxazolo[4,5-h][3]benzazepine hydrochloride

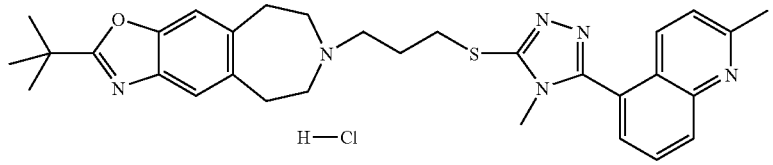

The title compound was prepared in analogy to General Procedure 1 from 2-(1,1-dimethylethyl)-6,7,8,9-tetrahydro-5H-[1,3]oxazolo[4,5-h][3]benzazepine (0.20 mmol) and 5-{5-[(3-chloropropyl)thio]-4-methyl-4H-1,2,4-triazol-3-yl}-2-methylquinoline and was obtained as a yellow slightly hygroscopic solid (59 μmmol).

NMR (1H, CD3OD): δ 8.24 (d, 1H), 8.17 (d, 1H), 7.95 (t, 1H), 7.8 (d, 1H), 7.53-7.57 (m, 3H), 3.54 (s, 3H), 3.2-3.4 (m, 12H), 2.79 (s, 3H), 2.41 (m, 2H), 1.5 (s, 9H), acidic proton not observed. MS (m/z): 541 [MH]+.

EXAMPLE 6

7-(3-{[4-Methyl-5-(2-methyl-5-quinolinyl)-4H-1,2,4-triazol-3-yl]thio}propyl)-2-propyl-6,7,8,9-tetrahydro-5H-[1,3]oxazolo[4,5-h][3]benzazepine hydrochloride

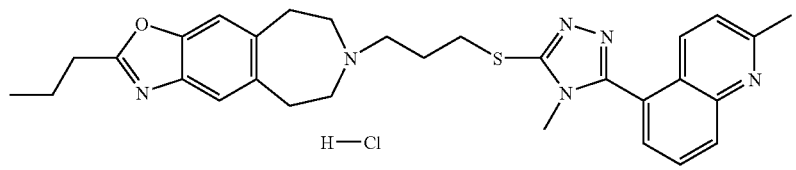

The title compound was prepared in analogy to General Procedure 1 from 2-propyl-6,7,8,9-tetrahydro-5H-[1,3]oxazolo[4,5-h][3]benzazepine (87 μmol) and 5-{5-[(3-chloropropyl)thio]-4-methyl-4H-1,2,4-triazol-3-yl}-2-methylquinoline and was obtained as a colourless solid (55 μmol).

NMR ($^1$H, CD$_3$OD): δ 8.23 (d, 1H), 8.18 (d, 1H), 7.95 (dd, 1H), 7.70 (dd, 1H), 7.54 (m, 3H), 3-4 (vbm, 8H), 3.54 (s, 3H), 3.47 (m, 4H), 2.95 (t, 2H), 2.79 (s, 3H), 2.41 (quint., 2H), 1.92 (sest., 2H), 1.06 (t, 3H), acidic proton not observed. MS (m/z): 527 [MH]$^+$.

EXAMPLE 7

7-(3-{[4-Methyl-5-(2-methyl-5-quinolinyl)-4H-1,2,4-triazol-3-yl]thio}propyl)-2-(2,2,2-trifluoroethyl)-6,7,8,9-tetrahydro-5H-[1,3]oxazolo[4,5-h][3]benzazepine hydrochloride

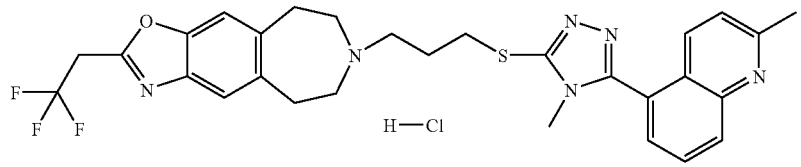

The title compound was prepared in analogy to General Procedure 1—but substituting the potassium carbonate with potassium bicarbonate. (2 eq.)—from 2-(2,2,2-trifluoroethyl)-6,7,8,9-tetrahydro-5H-[1,3]oxazolo[4,5-h][3]benzazepine (0.20 mmol) and 5-{5-[(3 chloropropyl)thio]-4-methyl-4H-1,2,4-triazol-3-yl}-2-methylquinoline and was obtained as a yellowish powder (33 μmol).

NMR ($^1$H, CD$_3$OD): δ 8.23 (d, 1H), 8.17 (d, 1H), 7.95 (dd, 1H), 7.79 (dd, 1H), 7.66 (s, 1H), 7.61 (s, 1H), 7.55 (d, 1H), 4.1

(m, 2H), 3-4 (vbm, 8H), 3.54 (s, 3H), 3.47 (m, 4H), 2.79 (s, 3H), 2.41 (quint., 2H), acidic proton not observed. MS (m/z): 567 [MH]+.

EXAMPLE 8

7-(3-{[4-Methyl-5-(2-methyl-5-quinolinyl)-4H-1,2,4-triazol-3-yl]thio}propyl)-2-(trifluoromethyl)-6,7,8,9-tetrahydro-5H-[1,3]oxazolo[4,5-h][3]benzazepine hydrochloride

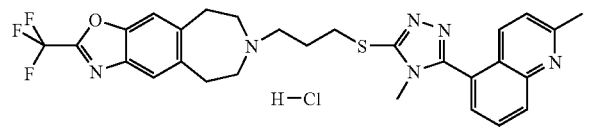

The title compound was prepared in analogy to General Procedure 1 from 2-(trifluoromethyl)-6,7,8,9-tetrahydro-5H-[1,3]oxazolo[4,5-h][3]benzazepine (0.14 μmol) and 5-{5-[(3-chloropropyl)thio]-4-methyl-4H-1,2,4-triazol-3-yl}-2-methylquinoline and was obtained as a colourless solid (97 μmol).

NMR (¹H, CD₃OD): δ 8.10 (d, 1H), 8.05 (d, 1H), 7.82 (dd, 1H), 7.71 (s, 1H), 7.67 (dd, 1H), 7.64 (s, 1H), 7.43 (d, 1H), 3.81 (bs, 2H), 3.5 (vbm, 6H), 3.41 (s, 3H), 3.36 (m, 4H), 2.67 (s, 3H), 2.31 (quint., 2H), acidic proton not observed. MS (m/z): 553 [MH]+.

EXAMPLE 9

8-(3-{[4-Methyl-5-(2-methyl-5-quinolinyl)-4H-1,2,4-triazol-3-yl]thio}propyl)-2,3,4,6,7,8,9,10-octahydro[1,4]oxazino[2,3-h][3]benzazepine hydrochloride

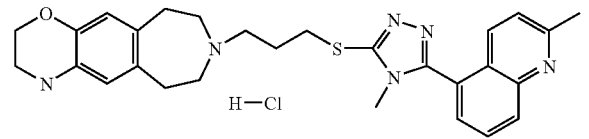

To 1,1-dimethylethyl 7-amino-8-hydroxy-1,2,4,5-tetrahydro-3H-3-benzazepine-3-carboxylate (0.28 g) in DMF (4 ml) was added acetic anhydride (1.05 eq.) at 0° C. and the mixture was allowed to warm to 25° C. After 3 h it was concentrated to half volume under reduced pressure and DMF (2 ml) was added, followed by addition at 0° C. of 1,2-dibromoethane (0.10 ml) and NaH (60% in mineral oil, 0.10 g). After 1 h at 25° C. aqueous NaOH (1 M, 2 ml) was added and the mixture was stirred for 16 h. Aqueous NaHCO₃ was added, the organic phase evaporated and the residue partitioned between ethyl acetate and water. The organic layer was concentrated, submitted to column chromatography to give a brown oil (0.25 g) of MS (m/z): 321. This material was dissolved in DMF (3 ml) and 1,2-dibromoethane (0.074 ml) and NaH (60% in mineral oil, 0.078 g) were added. After 6 days at 25° C. aqueous NaHCO₃ was added, the organic phase evaporated and the residue extracted with 1:1 DCM:ethyl acetate. The organic layer was concentrated, submitted to column chromatography to give a brown oil (0.051 g) which was treated with TFA (1 ml) in DCM (2 ml) for 3 h at 25° C. After elimination of the organic phase under reduced pressure the residue was partitioned between aqueous NaHCO₃ and DCM. The organic layer was collected and the aqueous phase extracted twice with DCM. The combined DCM layers were dried (Na₂SO₄), filtered and concentrated to give a brown film (0.031 g). From this material was obtained as a minor product in analogy to General Procedure 1 using 5-{5-[(3-chloropropyl)thio]-4-methyl-4H-1,2,4-triazol-3-yl}-2-methylquinoline the title compound as a yellow film (4 mg).

NMR (¹H, CD₃OD): δ 8.23 (d, 1H), 8.15 (d, 1H), 7.94 (t, 1H), 7.78 (dd, 1H), 7.54 (d, 1H), 6.55 (s, 1H), 6.48 (s, 1H), 4.17 (dd, 2H), 3.53 (s, 3H), 3.0-3.5 (vm, 12H), 3.4(t, 2H), 2.97 (bs, 3H), 2.27 (quint., 2H), 2 acidic protons not observed. MS (m/z): 501 [MH]+.

EXAMPLE 10

4-Methyl-8-(3-{[4-methyl-5-(2-methyl-5-quinolinyl)-4H-1,2,4-triazol-3-yl]thio}propyl)-4,6,7,8,9,10-hexahydro[1,4]oxazino[2,3-h][3]benzazepin-3(2H)-one hydrochloride

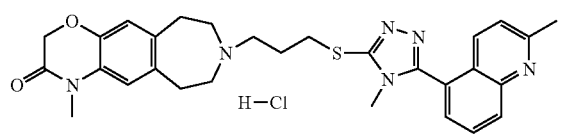

The title compound was prepared in analogy to General Procedure 1 from 4-methyl-4,6,7,8,9,10-hexahydro[1,4]oxazino[2,3-h][3]benzazepin-3(2H)-one (37 mg) and 5-{5-[(3-chloropropyl)thio]-4-methyl-4H-1,2,4-triazol-3-yl}-2-methylquinoline and was obtained as a colourless sticky solid (41 mg).

NMR (¹H, CD₃OD): δ 8.23 (d, 1H), 8.17 (d, 1H), 7.95 (t, 1H), 7.79 (dd, 1H), 7.55 (d, 1H), 7.08 (s, 1H), 6.92 (s, 1H), 4.61 (s, 2H), 3.0-4.0 (vbm, 10H), 3.54 (s, 3H), 3.47 (t, 2H), 3.37 (s, 3H), 2.79 (s, 3H), 2.4 (quint., 2H), acidic proton not observed. MS (m/z): 529 [MH]+.

EXAMPLE 11

4-Methyl-8-(3-{[4-methyl-5-(4-methyl-1,3-oxazol-5-yl)-4H-1,2,4-triazol-3-yl]thio}propyl)-4,6,7,8,9,10-hexahydro[1,4]oxazino[2,3-h][3]benzazepin-3(2H)-one hydrochloride

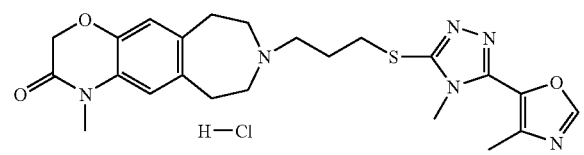

The title compound was prepared in analogy to General Procedure 1 from 4-methyl-4,6,7,8,9,10-hexahydro[1,4]oxazino[2,3-h][3]benzazepin-3(2H)-one (37 mg) and 3-[(3-chloropropyl)thio]-4-methyl-5-(4-methyl-1,3-oxazol-5-yl)-4H-1,2,4-triazole and was obtained as a faint yellow slightly sticky solid (45 mg).

NMR (1H, CD₃OD): δ 8.4 (s, 1H), 7.08 (s, 1H), 6.92 (s, 1H), 4.61 (s, 2H), 3.81 (s, 3H), 3.8 (m, 2H), 3.0-3.5 (vm, 8H), 3.44 (t, 2H), 3.38 (s, 3H), 2.47 (s, 3H), 2.33 (quint., 2H), acidic proton not observed. MS (m/z): 469 [MH]+.

EXAMPLE 12

2-(Cyclopropylmethyl)-7-(3-{[4-methyl-5-(2-methyl-5-quinolinyl)-4H-1,2,4-triazol-3-yl]thio}propyl)-6,7,8,9-tetrahydro-5H-[1,3]oxazolo[4,5-h][3]benzazepine hydrochloride

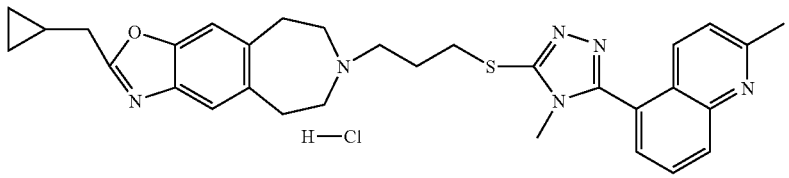

The title compound was prepared in analogy to General Procedure 1 from 2-(cyclopropylmethyl)-6,7,8,9-tetrahydro-5H-[1,3]oxazolo[4,5-h][3]benzazepine (0.19 mmol) and 5-{5-[(3-chloropropyl)thio]-4-methyl-4H-1,2,4-triazol-3-yl}-2-methylquinoline and was obtained as a faint yellow slightly hygroscopic solid (0.07 mmol).

NMR ($^1$H, CD$_3$OD): δ 8.6 (d, 1H), 8.03 (d, 1H), 7.92 (t, 1H), 7.78 (d, 1H), 7.62 (d, 1H), 7.21 (s, 1H), 7.19 (s, 1H), 3.57 (dd, 2H), 3.29 (s, 3H), 3.2 (m, 6H), 3.0 (m, 2H), 2.8 (t, 2H), 2.68 (s, 3H), 2.53 (d, 2H), 2.08 (m, 2H), 0.87 (m, 1H), 0.3 (m, 2H), 0.01 (m, 2H), acidic proton not observed. MS (m/z): 539 [MH]$^+$.

EXAMPLE 13

2-(Cyclopropylmethyl)-7-(3-[{4-methyl-5-(4-methyl-1,3-oxazol-5-yl)-4H-1,2,4-triazol-3-yl]thio}propyl)-6,7,8,9-tetrahydro-5H-[1,3]oxazolo[4,5-h][3]benzazepine hydrochloride

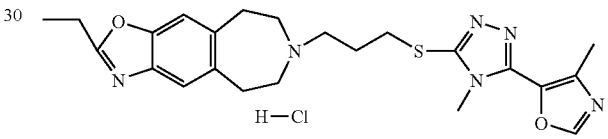

The title compound was prepared in analogy to General Procedure 1 from 2-cyclopropylmethyl)-6,7,8,9-tetrahydro-5H-[1,3]oxazolo[4,5-h][3]benzazepine (0.16 mmol) and 3-[(3-chloropropyl)thio]-4-methyl-5-(4-methyl-1,3-oxazol-5-yl)-4H-1,2,4-triazole and was obtained as a faint yellow slightly hygroscopic solid (0.06 mmol).

NMR ($^1$H, CD$_3$OD): δ 8.4 (s, 1H), 7.55 (2s, 2H), 3.87 (dd, 2H), 3.81 (s, 3H), 3.6-3.0 (m, 8H), 3.1 (m, 2H), 2.88 (dd, 2H), 2.47 (s, 3H), 2.34 (m, 2H), 1.24 (m, 1H), 0.65 (m, 2H), 0.36 (q, 2H), acidic proton not observed. MS (m/z): 480 [MH]$^+$.

EXAMPLE 14

2-Ethyl-7-(3-{[4-methyl-5-(4-methyl-1,3-oxazol-5-yl)-4H-1,2,4-triazol-3-yl]thio}propyl)-6,7,8,9-tetrahydro-5H-[1,3]oxazolo[4,5-h][3]benzazepine hydrochloride

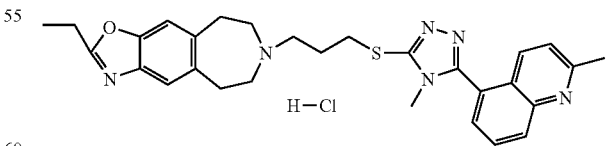

The title compound was prepared in analogy to General Procedure 1 rom 2-ethyl-6,7,8,9-tetrahydro-5H-[1,3]oxazolo[4,5-h][3]benzazepine (0.28 mmol) and 3-[(3-chloropropyl)thio]-4-methyl-5-(4-methyl-1,3-oxazol-5-yl)-4H-1,2,4-triazole and was obtained as a faint yellow slightly hygroscopic solid (0.07 mmol).

NMR ($^1$H, DMSO-D6): δ 10.28 (bs, 1H), 8.58 (s, 1H), 7.57 (t, 1H), 7.56 (s, 1H), 3.7 (m, 5H), 3.38 (m, 2H), 3.29 (m, 4H), 3.13 (m, 2H), 3.02 (m, 2H), 2.94 (q, 2H), 2.39 (s, 3H), 2.2 (m, 2H), 1.33 (t, 3H). MS (m/z): 453 [MH]$^+$.

EXAMPLE 15

2-Ethyl-7-(3-{[4-methyl-5-(2-methyl-5-quinolinyl)-4H-1,2,4-triazol-3-yl]thio}propyl)-6,7,8,9-tetrahydro-5H-[1,3]oxazolo[4,5-h][3]benzazepine The title compound was prepared in analogy to General Procedure 1 from 2-ethyl-6,7,8,9-tetrahydro-5H-[1,3]oxazolo[4,5-h][3]benzazepine (1.5 mmol) and 5-{5-[(3 chloropropyl)thio]-4-methyl-4H-1,2,4-triazol-3-yl}-2-methylquinoline and was obtained as a faint yellow slightly hygroscopic solid (0.75 mmol).

NMR (¹H, CD₃OD): δ 8.24 (d, 1H), 8.17 (d, 1H), 7.95 (t, 1H), 7.8 (d, 1H), 7.57-7.53 (m, 3H), 3.54 (s, 3H), 3.4-3.2 (m, 12H), 3.01 (q, 2H), 2.79 (s, 3H), 2.41 (m, 2H), 1.44 (t, 3H) acidic proton not observed. MS (m/z): 513 [MH]⁺.

EXAMPLE 16

3-Methyl-7-(3-{[4-methyl-5-(2-methyl-5-quinolinyl)-4H-1,2,4-triazol-3-yl]thio}propyl)-6,7,8,9-tetrahydro-5H-isoxazolo[4,5-h][3]benzazepine hydrochloride

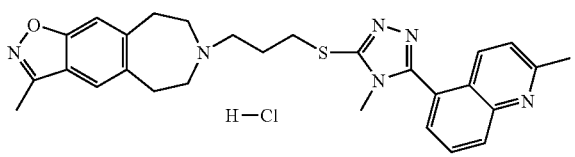

The title compound was prepared in analogy to General Procedure 1 from 3-methyl-6,7,8,9-tetrahydro-5H-isoxazolo[4,5-h][3]benzazepine (0.63 mmol) and 5-{5-[(3-chloropropyl)thio]-4-methyl-4H-1,2,4-triazol-3-yl}-2-methylquinoline and was obtained as a faint yellow slightly hygroscopic solid (0.11 mmol).

NMR (1H, DMSO-D6): δ 10.18 (bs, 1H), 8.5 (bs, 1H), 8.32 (d, 1H), 8.04 (t, 1H), 7.94 (d, 1H), 7.73 (s, 1H), 7.69 (bd, 1H), 7.62 (s, 1H), 3.49 (s, 3H), 3.7-3.3 (m, 8H), 3.08 (m, 4H), 2.84 (bs, 3H), 2.5 (s, 3H), 2.29 (m, 2H). MS (m/z): 499 [MH]⁺.

EXAMPLE 17

3-methyl-7-[3-({4-methyl-5-[4-(trifluoromethyl)phenyl]-4H-1,2,4-triazol-3-yl}thio)propyl]-6,7,8,9-tetrahydro-5H-isoxazolo[4,5-h][3]benzazepine hydrochloride

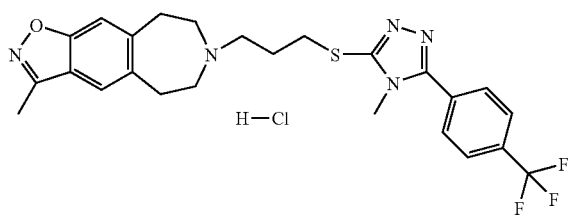

The title compound was prepared in analogy to General Procedure 1 from 3-methyl-6,7,8,9-tetrahydro-5H-isoxazolo[4,5-h][3]benzazepine (0.12 mmol) and 3-[(3-chloropropyl)thio]-4-methyl-5-[4-(trifluoromethyl)phenyl]-4H-1,2,4-triazole (0.14 mmol) and was obtained as a faint yellow slightly hygroscopic solid (0.01 mmol).

NMR (1H, DMSO-D6): 10.58 (bs, 1H), 7:97 (m, 4H), 7.73 (s, 1H), 7.62 (s, 1H), 3.68 (s, 3H), 3.8-3.0 (several m, 12H), 2.54 (s, 3H), 2.24 (m, 2H). MS (m/z): 502 [MH]

EXAMPLE 18

2-Cyclopropyl-7-(3-{[4-methyl-5-(2-methyl-5-quinolinyl)-4H-1,2,4-triazol-3-yl]thio}propyl)-6,7,8,9-tetrahydro-5H-[1,3]oxazolo[4,5-h][3]benzazepine hydrochloride

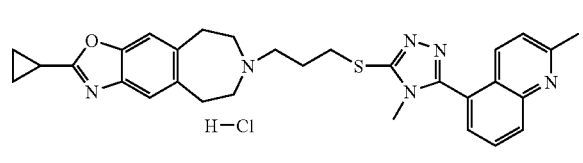

The title compound was prepared in analogy to General Procedure 1 from 2-cyclopropyl-6,7,8,9-tetrahydro-5H-[1,3]oxazolo[4,5-h][3]benzazepine (0.46 mmol) and 5-{5-[(3-chloropropyl)thio]-4-methyl-4H-1,2,4-triazol-3-yl}-2-methylquinoline (0.544 mmol) and was obtained as a yellow solid (0.19 mmol).

NMR (¹H, CD₃OD): δ 9.13 (d, 1H), 8.43 (dd, 1H), 8.35 (t, 1H), 8.23 (dd, 1H), 8.06 (d, 1H), 7.48 (s, 2H), 3.91 and 3.6-3.0 (various m, 12H), 3.69 (s, 3H), 3.09 (s, 3H), 2.44 (m, 2H), 2.27 (m, 1H), 1.27 (m, 4H), acidic proton not observed. MS (m/z): 526 [MH]⁺.

EXAMPLE 19

2-Methyl-7-(2-{[4-methyl-5-(2-methylquinolin-5-yl)-4H-1,2,4-triazol-3-yl]thio}ethyl)-6,7,8,9-tetrahydro-5H-[1,3]oxazolo[4,5-h][3]benzazepine hydrochloride

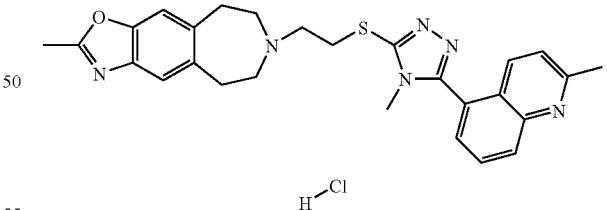

The title compound was prepared in analogy to General Procedure 1 from 7-(2-chloroethyl)-2-methyl-6,7,8,9-tetrahydro-5H-[1,3]oxazolo[4,5-h][3]benzazepine (0.11 mmol) and 4-methyl-5-(2-methyl-5-quinolinyl)-2,4-dihydro-3H-1,2,4-triazole-3-thione (0.11 mmol) and was obtained in 40 mg yield.

NMR (¹H, CD₃OD): δ 8.42 (d, 1H), 8.18 (d, 1H), 7.98 (t, 1H), 7.82 (d, 1H), 7.62 (d, 1H), 7.43 (s, 1H), 7.42 (s, 1H), 3.88

(m, 2H), 3.67 (s, 3H), 3.5-3.1 (bm, 10H), 2.78 (s, 3H), 2.53 (s, 3H), acidic proton not observed. MS (m/z): 485 [MH]$^+$.

EXAMPLE 20

8-(3-{[4-methyl-5-(2-methyl-5-quinolinyl)-4H-1,2,4-triazol-3-yl]thio}propyl)-4-(methylsulfonyl)-2,3,4,6,7,8,9,10-octahydro[1,4]oxazino[2,3-h][3]benzazepine hydrochloride

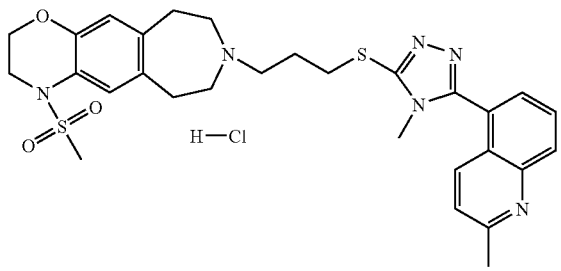

The title compound was prepared in analogy to General Procedure 1 from 4-(methylsulfonyl)-2,3,4,6,7,8,9,10-octahydro[1,4]oxazino[2,3-h][3]benzazepine (30 mg) and 5-{5-[(3-chloropropyl)thio]-4-methyl-4H-1,2,4-triazol-3-yl}-2-methylquinoline and was obtained as a yellow slightly hygroscopic solid (20 mg).

NMR ($^1$H, DMSO): δ 10 (bs, 1H), 8.21 (bd, 1H), 8.16 (d, 1H), 7.92 (t, 1H), 7.77 (d, 1H), 7.53 (d, 1H), 7.42 (s, 1H), 6.83 (s, 1H), 4.23 (t, 2H), 3.8-2.9 (bm, 12H), 3.42 (s, 3H), 3.32 (t, 2H), 3.1 (s, 3H), 2.7 (s, 3H), 2.23 (q, 2H), acidic proton not observed. MS (m/z): 579 [MH]$^-$.

EXAMPLE 21

2-Methyl-7-[3-({4-methyl-5-[4-(trifluoromethyl)phenyl]-4H-1,2,4-triazol-3-yl}thio)propyl]-6,7,8,9-tetrahydro-5H-[1,3]oxazolo[4,5-h][3]benzazepine hydrochloride

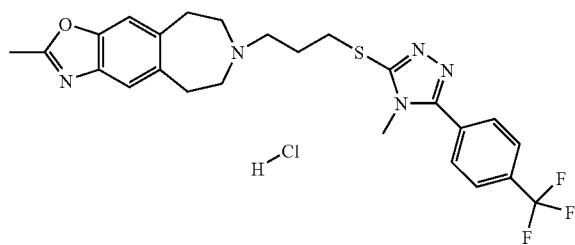

The title compound was prepared in analogy to General Procedure 1 from 2-methyl-6,7,8,9-tetrahydro-5H-[1,3]oxazolo[4,5-h][3]benzazepine (0.25 mmol) and 3-[(3-chloropropyl)thio]-4-methyl-5-[4-(trifluoromethyl)phenyl]-4H-1,2,4-triazole and was obtained as a faint yellow slightly hygroscopic solid (0.074 mmol).

NMR ($^1$H, CD$_3$OD): δ 8.0 (m, 4H), 7.53 (s, 1H), 7.52 (s, 1H), 3.87 (m, 2H), 3.79 (s, 3H), 3.5-3.3 (m, 8H), 3.15 (m, 2H), 2.65 (s, 3H), 2.39 (m, 2H), acidic proton not observed. MS (m/z): 502 [MH]$^+$.

EXAMPLE 22

7-(3-{[5-(3,4-Difluorophenyl)-4-methyl-4H-1,2,4-triazol-3-yl]thio}propyl)-2-methyl-6,7,8,9-tetrahydro-5H-[1,3]oxazolo[4,5-h][3]benzazepine hydrochloride

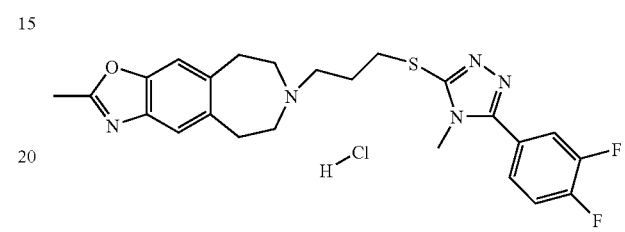

The title compound was prepared in analogy to General Procedure 1 from 2-methyl-6,7,8,9-tetrahydro-5H-[1,3]oxazolo[4,5-h][3]benzazepine (0.25 mmol) and 3-[(3-chloropropyl)thio]-5-(3,4-difluorophenyl)-4-methyl-4H-1,2,4-triazole and was obtained as a faint yellow slightly hygroscopic solid (0.11 mmol).

NMR ($^1$H, CD$_3$OD): δ 7.79 (m, 1H), 7.63 (m, 2H), 7.53 (s, 1H), 7.52 (s, 1H), 3.87 (m, 2H), 3.77 (s, 3H), 3.44 (m, 4H), 3.5-3.3 (m, 2H), 3.29 (m, 2H), 3.15 (m, 2H), 2.65 (s, 3H), 2.38 (m, 2H), acidic proton not observed. MS (m/z): 470 [MH]$^+$.

EXAMPLE 23

2-Methyl-7-(3-{[4-methyl-5-(tetrahydro-2H-pyran-4-yl)-4H-1,2,4-triazol-3-yl]thio}propyl)-6,7,8,9-tetrahydro-5H-[1,3]oxazolo[4,5-h][3]benzazepine hydrochloride

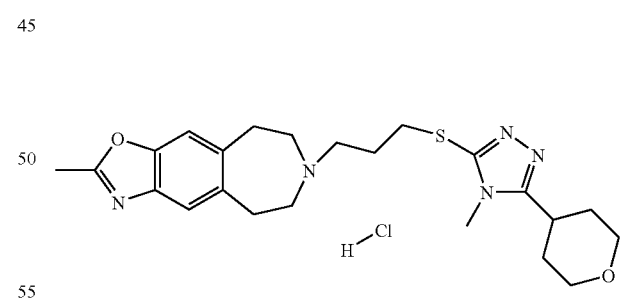

The title compound was prepared in analogy to General Procedure 1 from 2-methyl-6,7,8,9-tetrahydro-5H-[1,3]oxazolo[4,5-h][3]benzazepine (0.25 mmol) and 3-[(3-chloropropyl)thio]-4-methyl-5-(tetrahydro-2H-pyran-4-yl)-4H-1,2,4-triazole and was obtained as a faint yellow slightly hygroscopic solid (0.025 mmol).

NMR (1H, CD$_3$OD): δ 7.52 (m, 2H), 4.07 (m, 2H), 3.9-3.8 (s, 3H), 3.5-3.3 (bm, 2H), 3.77 (s, 3H), 3.63 (dt, 2H), 3.5-3.1

(bm, 7H), 3.42 (m, 4H), 2.65 (s, 3H), 2.35 (m, 2H), 2.00 (m, 2H), 1.93 (dt, 2H), acidic proton not observed. MS (m/z): 442 [MH]+.

EXAMPLE 24

2-Ethyl-7-(3-{[4-methyl-5-(3-pyridinyl)-4H-1,2,4-triazol-3-yl]thio}propyl)-6,7,8,9-tetrahydro-5H-[1,3]oxazolo[4,5-h][3]benzazepine hydrochloride

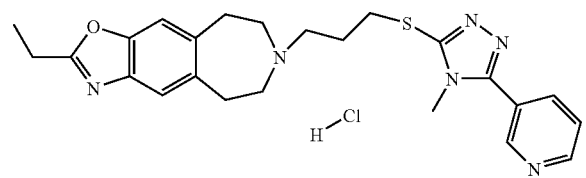

The title compound was prepared in analogy to General Procedure 1 from 2-ethyl-6,7,8,9-tetrahydro-5H-[1,3]oxazolo[4,5-h][3]benzazepine (0.25 mmol) and 3-{5-[(3-chloropropyl)thio]-4-methyl-4H-1,2,4-triazol-3-yl}pyridine and was obtained as a faint yellow slightly hygroscopic solid (0.12 mmol).

NMR (1H, CD3OD): δ 9.29 (d, 1H), 9.04 (d, 1H), 8.91 (m, 1H), 8.22 (dd, 1H), 7.54 (s, 1H), 7.52 (s, 1H), 3.86 (m, 2H), 3.85 (s, 3H), 3.45 (m, 6H), 3.30 (m, 2H), 3.15 (bm, 2H), 3.00 (q, 2H), 2.38 (m, 2H), 1.44 (t, 3H), acidic proton not observed. MS (m/z): 449 [MH]+.

EXAMPLE 25

2-Ethyl-7-[3-({4-methyl-5-[4-(trifluoromethyl)phenyl]-4H-1,2,4-triazol-3-yl}thio)propyl]-6,7,8,9-tetrahydro-5H-[1,3]oxazolo[4,5-h][3]benzazepine hydrochloride

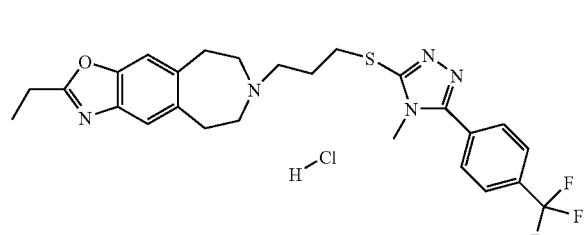

The title compound was prepared in analogy to General Procedure 1 from 2-ethyl-6,7,8,9-tetrahydro-5H-[1,3]oxazolo[4,5-h][3]benzazepine (0.25 mmol) and 3-[(3-chloropropyl)thio]-4-methyl-5-[4-(trifluoromethyl)phenyl]-4H-1,2,4-triazole and was obtained as a faint yellow slightly hygroscopic solid (0.074 mmol).

NMR (1H, CD3OD): δ 7.99 (m, 4H), 7.55 (s, 1H), 7.53 (s, 1H), 3.88 (m, 2H), 3.79 (s, 3H), 3.45 (m, 6H), 3.27 (bm, 2H), 3.14 (bm, 2H), 3.00 (q, 2H), 2.38 (m, 2H), 1.45 (t, 3H), acidic proton not observed. MS (m/z): 516 [MH]+.

EXAMPLE 26

7-(3-{[5-(3,4-Difluorophenyl)-4-methyl-4H-1,2,4-triazol-3-yl]thio}propyl)-2-ethyl-6,7,8,9-tetrahydro-5H-[1,3]oxazolo[4,5-h][3]benzazepine hydrochloride

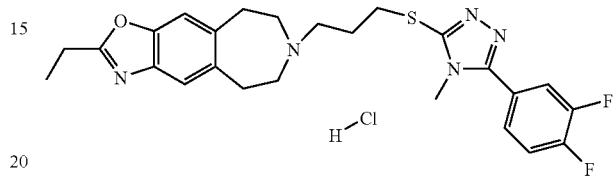

The title compound was prepared in analogy to General Procedure 1 from 2-ethyl-6,7,8,9-tetrahydro-5H-[1,3]oxazolo[4,5-h][3]benzazepine (0.25 mmol) and 3-[(3-chloropropyl)thio]-5-(3,4-difluorophenyl)-4-methyl-4H-1,2,4-triazole and was obtained as a faint yellow slightly hygroscopic solid (0.11 mmol).

NMR (1H, CD3OD): δ 7.78 (m, 1H), 7.6-7.58 (m, 2H), 7.55 (s, 1H), 7.52 (s, 1H), 3.87 (m, 2H), 3.76 (s, 3H), 3.43 (m, 6H), 3.3 (m, 2H), 3.15 (m, 2H), 3.00 (q, 2H), 2.37 (m, 2H), 1.45 (t, 3H), acidic proton not observed. MS (m/z): 484 [MH]+.

EXAMPLE 27

7-(3-{[4-methyl-5-(2-methyl-5-quinolinyl)-4H-1,2,4-triazol-3-yl]thio}propyl)-2-(1-piperidinyl)-6,7,8,9-tetrahydro-5H-[1,3]oxazolo[4,5-h][3]benzazepine di-hydrochloride

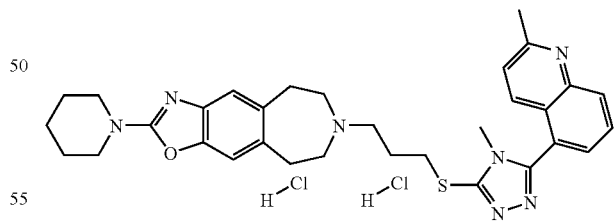

The title compound was prepared in analogy to General Procedure 1 from 2-(1-piperidinyl)-6,7,8,9-tetrahydro-5H-[1,3]oxazolo[4,5-h][3]benzazepine bis(trifluoroacetate) (0.130 mmol) and 5-(5-[(3-chloropropyl)thio]-4-methyl-4H-1,2,4-triazol-3-yl)-2-methylquinoline and was obtained as a white slightly hygroscopic solid (6.2 μmol).

NMR (1H, CD3OD): δ 9.13 (d, 1H), 8.44 (d, 1H), 8.35 (t, 1H), 8.24 (d, 1H), 8.06 (d, 1H), 7.53 (s, 1H), 7.36 (s, 1H), 3.92 (bdd, 2H), 3.81 (m, 4H), 3.67 (s, 3H), 3.6-3.4 (vm, 6H), 3.4-3.1 (vm, 4H), 3.09 (s, 3H), 2.44 (quint., 2H), 1.84 (bm, 6H) acidic protons not observed. MS (m/z): 568 [MH]+.

EXAMPLE 28

N,N-dimethyl-7-(3-{[4-methyl-5-(2-methyl-5-quinolinyl)-4H-1,2,4-triazol-3-yl]thio}propyl)-6,7,8,9-tetrahydro-5H-[1,3]oxazolo[4,5-h][3]benzazepin-2-amine dihydrochloride

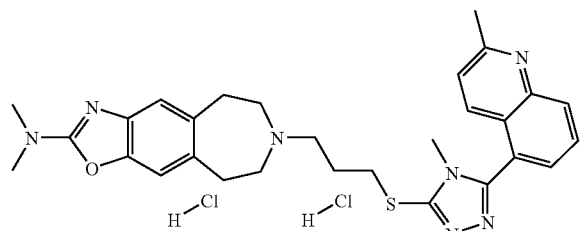

The title compound was prepared in analogy to General Procedure 1 from N,N-dimethyl-6,7,8,9-tetrahydro-5H-[1,3]oxazolo[4,5-h][3]benzazepin-2-amine (0.18 mmol) and 5-{5-[(3-chloropropyl)thio]-4-methyl-4H-1,2,4-triazol-3-yl}-2-methylquinoline and was obtained as a white slightly hygroscopic solid (0.045 mmol).

NMR (1H, CD$_3$OD): δ 9.16 (d, 1H), 8.47 (dd, 1H), 8.36 (t, 1H), 8.28 (dd, 1H), 8.08 (d, 1H), 7.57 (s, 1H), 7.39 (s, 1H), 3.91 (m, 2H), 3.6-3.31 (vm, 12H), 3.7 (s, 3H), 3.4 (m, 6H), 3.1 (s, 3H), 2.45 (m, 2H), acidic protons not observed. MS (m/z): 528 [MH]+.

EXAMPLES 29-36

The following examples were prepared in analogy to General Procedure 1 from the corresponding secondary amine (Preparations 33, 34, 35, 38 and 39) and chloropropyl derivatives (Preparations 1 or 2).

| Example N. | Name, Structure, Appearance | Analytical data |
|---|---|---|
| 29 | 3-Ethyl-7-(3-{[4-methyl-5-(2-methyl-5-quinolinyl)-4H-1,2,4-triazol-3-yl]thio}propyl)-6,7,8,9-tetrahydro-5H-isoxazolo[4,5-h][3]benzazepine hydrochloride<br><br>yellow solid | NMR (¹H, CD$_3$OD): δ 8.26 (m, 2H), 8.0 (dd, 1H), 7.83 (dd, 1H), 7.73 (s, 1H), 7.61 (d, 1 H), 7.55 (s, 1H), 3.9-4 (bs, 2H), 3.55 (s, 3H), 3.1-3.6 (vbm, 6H), 3.5-3.6 (m, 4H), 3.05 (q, 2H), 2.82 (s, 3H), 2.42 (m, 2H), 1.44 (t, 3H), acidic proton not observed. MS (m/z): 513 [MH]+. |
| 30 | 2-(1,3-Dimethyl-1H-pyrazol-5-yl)-7-(3-{[4-methyl-5-(2-methyl-5-quinolinyl)-4H-1,2,4-triazol-3-yl]thio}propyl)-6,7,8,9-tetrahydro-5H-[1,3]oxazolo[4,5-h][3]benzazepine hydrochloride<br><br>yellow solid | NMR (¹H, CD$_3$OD): δ 8.33 (d, 1H), 8.26 (d, 1H), 8.01 (dd, 1H), 7.86 (d, 1H), 7.7 (s, 1H), 7.63 (d, 1H), 7.63 (s, 1H), 6.88 (s, 1H), 4.3 (s, 3H), 3.95 (bs, 2H), 3.56 (s, 3H), 3.49 + 3.3 + 3.2 (3m, 10H), 2.84 (s, 3H), 2.43 (m, 2H), 2.33 (s, 3H), acidic proton not observed. MS (m/z): 579 [MH]+. |
| 31 | 2-(1,3-Dimethyl-1H-pyrazol-5-yl)-7-(3-{[4-methyl-5-(4-methyl-1,3-oxazol-5-yl)-4H-1,2,4-triazol-3-yl]thio}propyl)-6,7,8,9-tetrahydro-5H-[1,3]oxazolo[4,5-h][3]benzazepine hydrochloride<br><br>colourles solid | NMR (¹H, CD$_3$OD): δ 8.4 (s, 1H), 7.7 (s, 1H), 7.63 (s, 1H), 6.89 (s, 1H), 4.3 (s, 3H), 3.9 (m, 2H), 3.82 (s, 3H), 3.3-3.6 + 3.16 (multiple m, 10H), 2.47 (s, 3H), 2.35 (m, 2H), 2.33 (s, 3H), acidic proton not observed. MS (m/z): 519 [MH]+. |

| Example N. | Name, Structure, Appearance | Analytical data |
|---|---|---|
| 32 | 7-(3-{[4-Methyl-5-(2-methyl-5-quinolinyl)-4H-1,2,4-triazol-3-yl]thio}propyl)-2-(pentafluoroethyl)-6,7,8,9-tetrahydro-5H-[1,3]oxazolo[4,5-h][3]benzazepine hydrochloride<br><br>faint yellow solid | NMR ($^1$H, CD$_3$OD): δ 8.25 (m, 2H), 7.99 (dd, 1H), 7.86 (s, 1H), 7.83 (d, 1H), 7.79 (d, 1H), 7.6 (s, 1H), 3.95 (bs, 2H), 3.55 (s, 3H), 3.49 + 3.3 + 3.2 (3m, 10H), 2.82 (s, 3H), 2.43 (m, 2H), acidic proton not observed. MS (m/z): 603 [MH]$^+$. |
| 33 | 7-(3-{[4-Methyl-5-(4-methyl-1,3-oxazol-5-yl)-4H-1,2,4-triazol-3-yl]thio}propyl)-2-(pentafluoroethyl)-6,7,8,9-tetrahydro-5H-[1,3]oxazolo[4,5-h][3]benzazepine hydrochloride<br><br>colourless solid | NMR ($^1$H, CD$_3$OD): δ 8.4 (s, 1H), 7.86 (s, 1H), 7.75 (s, 1H), 3.9 (m, 2H), 3.82 (s, 3H), 3.3-3.6 + 3.2 (multiple m, 10H), 2.47 (s, 3H), 2.36 (m, 2H), acidic proton not observed. MS (m/z) 543 [MH]$^+$. |
| 34 | 3-Ethyl-1-methyl-7-(3-{(4-methyl-5-(2-methyl-5-quinolinyl)-4H-1,2,4-triazol-3-yl]thio}propyl)-1,5,6,7,8,9-hexahydroazepino[4,5-f]indazole hydrochloride<br><br>colourless film | NMR ($^1$H, CD$_3$OD): δ 8.23 (d, 1H), 8.18 (d, 1H), 7.95 (m, 1H), 7.79 (d, 1H), 7.64 (s, 1H), 7.55 (d, 1H), 7.41 (s, 1H), 3.99 (s, 3H), 3.54 (s, 3H), 3.9 + 3.6-3.0 (multiple m, 12H), 2.97 (q, 2H), 2.79 (s, 3H), 2.42 (m, 2H), 1.38 (t, 3H), acidic proton not observed. MS (m/z): 526 [MH]$^+$. |
| 35 | 2-(1,1-Difluoroethyl)-7-(3-{(4-methyl-5-(2-methyl-5-quinolinyl)-4H-1,2,4-triazol-3-yl]thio}propyl)-6,7,8,9-tetrahydro-5H-[1,3]oxazolo[4,5-h][3]benzazepine hydrochloride<br><br>yellow powder | NMR ($^1$H, CD$_3$OD): δ 8.24 (d, 1H), 8.22 (d, 1H), 7.96 (t, 1H), 7.81 (d, 1H), 7.73 (s, 1H), 7.67 (s, 1H), 7.57 (d, 1H), 3.53 (s, 3H), 3.48 (t, 2H), 3.44 (t, 2H), 3.0-4.0 (m, 8H), 2.79 (s, 3H), 2.4 (q, 2H), 2.16 (t, 3H), acidic proton not observed. MS (m/z): 549 [MH]$^+$. |
| 36 | 2-(1,1-Difluoroethyl)-7-(3-{[4-methyl-5-(4-methyl-1,3-oxazol-5-yl)-4H-1,2,4-triazol-3-yl]thio}propyl)-6,7,8,9-tetrahydro-5H-[1,3]oxazolo[4,5-h][3]benzazepine hydrochloride<br><br>colourless powder | NMR ($^1$H, CD$_3$OD): δ 8.30 (s, 1H), 7.65 (s, 1H), 7.60 (s, 1H), 3.75-3.85 (m, 2H), 3.68 (s, 3H), 3.17-3.50 (m, 8H), 2.95-3.10 (m, 2H), 2.31 (s, 3H), 2.18-2.29 (m, 2H), 2.07 (t, 3H), acidic proton not observed. MS (m/z): 489 [MH]$^+$. |

EXAMPLE 37

2-methyl-7-(3-{[4-methyl-5-(2-methyl-5-quinolinyl)-4H-1,2,4-triazol-3-yl]thio}propyl)-6,7,8,9-tetrahydro-5H-[1,3]thiazolo[4,5-h][3]benzazepine hydrochloride

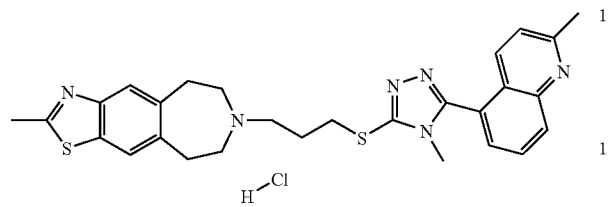

The title compound was prepared in analogy to General Procedure 1 from 2-methyl-6,7,8,9-tetrahydro-5H-[1,3]thiazolo[4,5-h][3]benzazepine (0.13 mmol) and 5-{5-[(3-chloropropyl)thio]-4-methyl-4H-1,2,4-triazol-3-yl}-2-methylquinoline (0.16 mmol) and was obtained as a colourless slightly hygroscopic solid (24 mg).

NMR ($^1$H, DMSO): δ 10.45 (bs, H$^+$), 8.25 (bd, 1H), 8.17 (d, 1H), 7.9 (t+s, 2H), 7.8 (m, 2H), 7.5 (d, 2H), 3.7-3.0 (bm, 12H), 3.44 (s, 3H), 2.77-2.73 (2s, 6H), 2.27 (quint, 2H).

MS (m/z): 515 [MH]$^+$.

EXAMPLE 38

2-methyl-7-(3-{[4-methyl-5-(4-methyl-1,3-oxazol-5-yl)-4H-1,2,4-triazol-3-yl]thio}propyl)-6,7,8,9-tetrahydro-5H-[1,3]thiazolo[4,5h][3]benzazepine hydrochloride

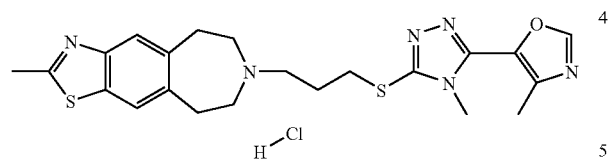

The title compound was prepared in analogy to General Procedure 1 from 2-methyl-6,7,8,9-tetrahydro-5H-[1,3]thiazolo[4,5-h][3]benzazepine (0.15 mmol) and 3-[(3-chloropropyl)thio]-4-methyl-5-(4-methyl-1,3-oxazol-5-yl)-4H-1,2,4-triazole (0.18 mmol) and was obtained as a colourless slightly hygroscopic solid (24 mg).

NMR ($^1$H, DMSO): δ 10.6 (bs, H$^+$), 8.58 (s, 1H), 7.9 (s, 1H), 7.8 (s, 1H), 3.8-3.7 (bs, 2H), 3.7 (s, 3H), 3.4-3.0 (bm, 12H), 2.78 (s, 3H), 2.39 (s, 3H), 2.20 (m, 2H)

MS (m/z): 455 [MH]$^+$..

EXAMPLE 39

2-ethyl-7-(3-{[4-methyl-5-(2-methyl-5-quinolinyl)-4H-1,2,4-triazol-3-yl]thio}propyl)-4,7,8,9-tetrahydro-5H-[1,3]thiazolo[4,5-h][3]benzazepine hydrochloride

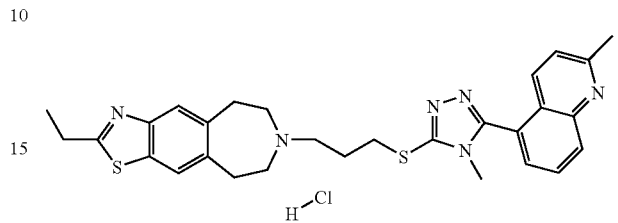

The title compound was prepared in analogy to General Procedure 1 from: 2-ethyl-6,7,8,9-tetrahydro-5H-[1,3]thiazolo[4,5-h][3]benzazepine (0.43 mmol) and 5-{5-[(3-chloropropyl)thio]-4-methyl-4H-1,2,4-triazol-3-yl}-2-methylquinoline (0.52 mmol) and was obtained as a colourless slightly hygroscopic solid (60 mg).

NMR ($^1$H, CD$_3$OD): δ 8.26 (m, 2H), 7.99 (t, 1H), 7.87 (s, 1H), 7.8 (m, 1H), 7.82 (s, 1H), 7.6 (d, 1H), 4-3.1 (bm, 12H), 3.55 (s, 3H), 3.18 (quart, 2H), 2.82 (s, 3H), 2.42 (quint, 2H), 1.47 (t, 3H). MS (m/z): 529 [MH]$^-$.

EXAMPLE 40

2-ethyl-7-(3-{[4-methyl-5-(4-methyl-1,3-oxazol-5-yl)-4H-1,2,4-triazol-3-yl]thio}propyl)-6,7,8,9-tetrahydro-5H-[1,3]thiazolo[4,5-h][3]benzazepine hydrochloride

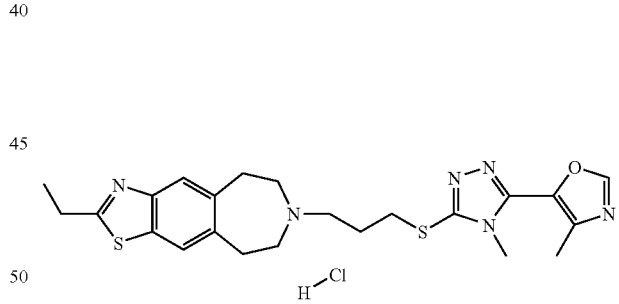

The title compound was prepared in analogy to General Procedure 1 from 2-ethyl-6,7,8,9-tetrahydro-5H-[1,3]thiazolo[4,5-h][3]benzazepine (0.14 mmol) and 3-[(3-chloropropyl)thio]-4-methyl-5-(4-methyl-1,3-oxazol-5-yl)-4H-1,2,4-triazole (0.16 mmol) and was obtained as a colourless slightly hygroscopic solid (13 mg).

NMR ($^1$H, CD3OD): δ 8.4 (s, 1H), 7.87 (s, 1H), 7.82 (s, 1H), 4-3.1 (bm, 8H), 3.81 (s, 3H), 3.45-3.39 (2t, 4H), 3.18 (quart, 2H), 2.47 (s, 3H), 2.35 (quint, 2H), 1.48 (t, 3H).

MS (m/z): 469 [MH]$^+$.

EXAMPLE 41

10-bromo-2-methyl-7-(3-{[4-methyl-5-(2-methyl-5-quinolinyl)-4H-1,2,4-triazol-3-yl]thio}propyl)-6,7,8,9-tetrahydro-5H-[1,3]oxazolo[4,5-h][3]benzazepine hydrochloride

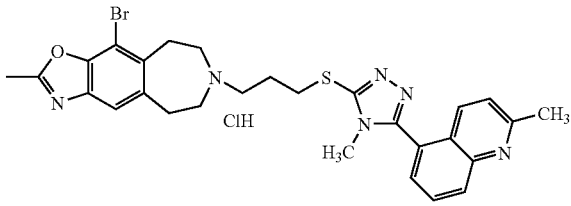

The title compound was prepared in analogy to General Procedure 1 from 10-bromo-2-methyl-6,7,8,9-tetrahydro-5H-[1,3]oxazolo[4,5-h][3]benzazepine (52 mg) and 5-{5-[(3-chloropropyl)thio]-4-methyl-4H-1,2,4-triazol-3-yl}-2-methylquinoline (73 mg) and was obtained as a colourless slightly hygroscopic solid (48 mg).

($^1$H-NMR, CDCl$_3$): 8.18 (d, 1H); 8.13 (d, 1H); 7.78 (dd, 1H); 7.56 (d, 1H); 7.32 (d, 1H); 7.26 (s, 1H); 3.44 (dd, 2H); 3.41 (s, 3H); 3.30 (m, 2H); 3.08 (m, 2H); 2.77 (s, 3H); 2.74 (m, 6H); 2.65 (s, 3H); 2.10 (m, 2H). MS (m/z): 578 [MH]$^+$.

EXAMPLE 42

10-bromo-7-(3-{[4-methyl-5-(2-methyl-5-quinolinyl)-4H-1,2,4-triazol-3-yl]thio}propyl)-2-(trifluoromethyl)-6,7,8,9-tetrahydro-5H-[1,3]oxazolo[4,5-h][3]benzazepine hydrochloride

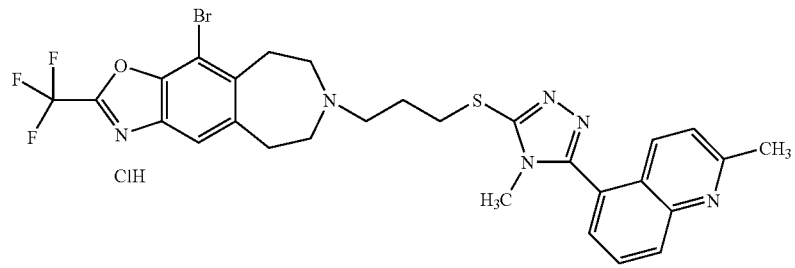

The title compound was prepared in analogy to General Procedure 1 from 10-bromo-2-(trifluoromethyl)-6,7,8,9-tetrahydro-5H-[1,3]oxazolo[4,5-h][3]benzazepine (58 mg) and 5-{5-[(3-chloropropyl)thio]-4-methyl-4H-1,2,4-triazol-3-yl}-2-methylquinoline and was obtained as a colourless slightly hygroscopic solid (20 mg).

($^1$H-NMR, CD$_3$OD): 8.20 (d, 1H); 8.14 (d, 1H); 7.92 (dd, 1H); 7.81 (s, 1H); 7.75 (d, 1H); 7.51 (d, 1H); 3.86-3.36 (m, 12H); 3.50 (s, 3H); 2.76 (s, 3H); 2.39 (m, 2H). MS (m/z): 632 [MH]$^+$.

EXAMPLE 43

10-bromo-2-methyl-7-(4-{[4-methyl-5-(2-methyl-5-quinolinyl)-4H-1,2,4-triazol-3-yl]thio}butyl)-6,7,8,9-tetrahydro-5H-[1,3]oxazolo[4,5-h][3]benzazepine hydrochloride

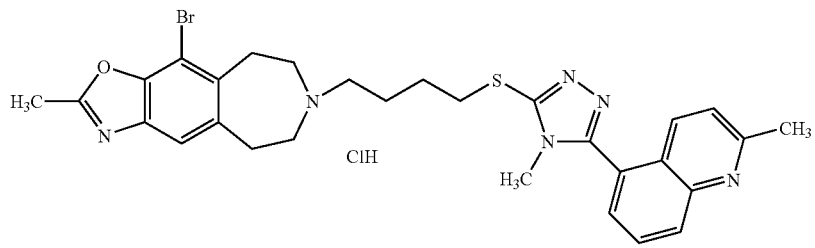

The title compound was prepared in analogy to General Procedure 1 from 10-bromo-2-methyl-6,7,8,9-tetrahydro-5H-[1,3]oxazolo[4,5-h][3]benzazepine (100 mg) and 5-{5-[(4-chlorobutyl)thio]-4-methyl-4H-1,2,4-triazol-3-yl}-2-methylquinoline (177 mg) and was obtained as a colourless slightly hygroscopic solid (127 mg).

($^1$H-NMR, CD$_3$OD): 8.41 (d, 1H); 8.25 (d, 1H); 8.03 (dd, 1H); 7.88 (d, 1H); 7.66 (d, 1H); 7.50 (s, 1H); 3.86 (m, 2H); 3.53 (s, 3H); 3.50 (m, 2H); 3.40-3.28 (m, 6H); 3.10 (m, 2H); 2.84 (s, 3H); 2.66 (s, 3H); 2.11-1.90 (m, 4H). MS (m/z): 592 [MH]$^+$.

EXAMPLE 44

10-bromo-2-ethyl-7-(4-{[4-methyl-5-(2-methyl-5-quinolinyl)-4H-1,2,4-triazol-3-yl]thio}butyl)-6,7,8,9-tetrahydro-5H-[1,3]oxazolo[4,5-h][3]benzazepine hydrochloride

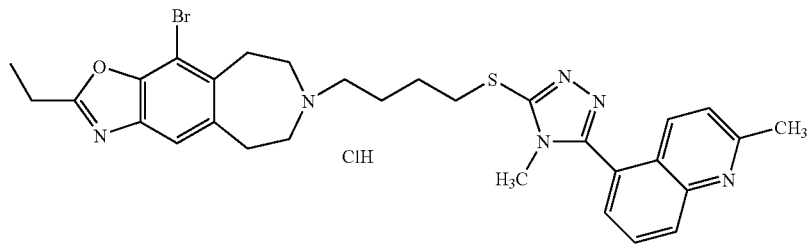

The title compound was prepared in analogy to General Procedure 1 from 10-bromo-2-ethyl-6,7,8,9-tetrahydro-5H-[1,3]oxazolo[4,5-h][3]benzazepine (105 mg) and 5-{5-[(4-chlorobutyl)thio]-4-methyl-4H-1,2,4-triazol-3-yl}-2-methylquinoline (177 mg) and was obtained as a colourless slightly hygroscopic solid (115 mg).

($^1$H-NMR, CD$_3$OD): 8.36 (d, 1H); 8.24 (d, 1H); 8.01 (dd, 1H); 7.85 (d, 1H); 7.63 (d, 1H); 7.51 (s, 1H); 3.86 (m, 2H); 3.63-3.46 (m, 2H); 3.52 (s, 3H); 3.46-3.25 (m, 6H); 3.09 (m, 2H); 3.00 (q, 2H); 2.83 (s, 3H); 2.16-1.90 (m, 4H); 1.42 (t, 3H). MS (m/z): 606 [MH]$^+$.

EXAMPLE 45

10-bromo-7-(4-{[4-methyl-5-(2-methyl-5-quinolinyl)-4H-1,2,4-triazol-3-yl]thio}butyl)-2-(trifluoromethyl)-6,7,8,9-tetrahydro-5H-[1,3]oxazolo[4,5-h][3]benzazepine hydrochloride

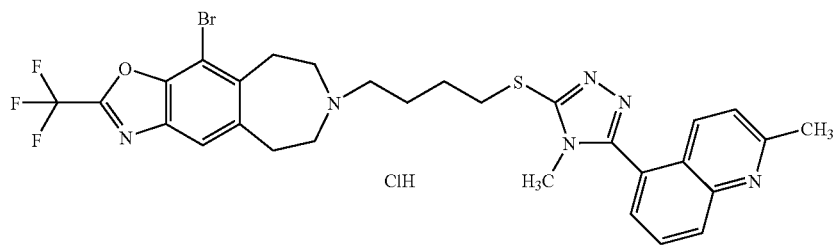

The title compound was prepared in analogy to General Procedure 1 from 10-Bromo-2-(trifluoromethyl)-6,7,8,9-tetrahydro-5H-[1,3]oxazolo[4,5-h][3]benzazepine (120 mg) and 5-{5-[(4-chlorobutyl)thio]-4-methyl-4H-1,2,4-triazol-3-yl}-2-methylquinoline (177 mg) and was obtained as a colourless slightly hygroscopic solid (66 mg).

($^1$H-NMR, CD$_3$OD): 8.44 (d, 1H); 8.25 (d, 1H); 8.04 (dd, 1H); 7.89 (d, 1H); 7.80 (s, 1H); 7.67 (d, 1H); 3.89 (m, 2H); 3.55 (m, 2H); 3.53 (s, 3H); 3.42-3.31 (m, 6H); 3.15 (m, 2H); 2.85 (s, 3H); 2.14-1.90 (m, 4H). MS (m/z): 646 [MH]$^+$.

EXAMPLE 46

2,10-dimethyl-7-(4-{[4-methyl-5-(2-methyl-5-quinolinyl)-4H-1,2,4-triazol-3-yl]thio}butyl)-6,7,8,9-tetrahydro-5H-[1,3]oxazolo[4,5-h][3]benzazepine hydrochloride

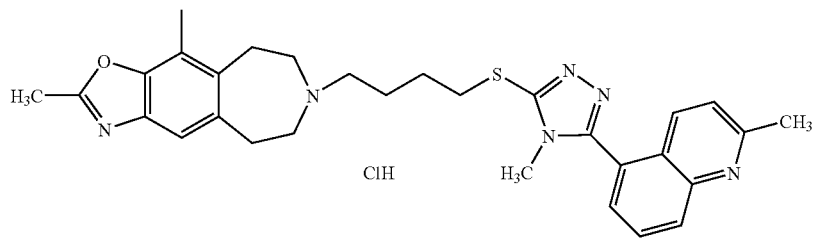

The title compound was prepared in analogy to General Procedure 1 from 2,10-dimethyl-6,7,8,9-tetrahydro-5H-[1,3]oxazolo[4,5-h][3]benzazepine (80 mg) and 5-{5-[(4-chlorobutyl)thio]-4-methyl-4H-1,2,4-triazol-3-yl}-2-methylquinoline (153 mg) and was obtained as a colourless slightly hygroscopic solid (146 mg).

($^1$H-NMR, CD$_3$OD): 8.57 (d, 1H); 8.28 (d, 1H); 8.09 (dd, 1H); 7.95 (d, 1H); 7.74 (d, 1H); 7.33 (s, 1H); 3.86 (m, 2H); 3.55 (s, 3H); 3.55-3.41 (m, 2H); 3.40-3.13 (m, 6H); 3.04 (m, 2H); 2.89 (s, 3H); 2.62 (s, 3H); 2.50 (s, 3H); 2.13-1.89 (m, 4H). MS (m/z): 527 [MH]$^+$.

EXAMPLE 47

2-Ethyl-10-methyl-7-(4-{[4-methyl-5-(2-methyl-5-quinolinyl)-4H-1,2,4-triazol-3-yl]thio}butyl)-6,7,8,9-tetrahydro-5H-[1,3]oxazolo[4,5-h][3]benzazepine hydrochloride

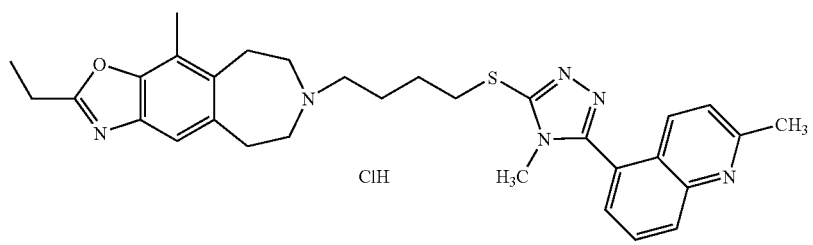

The title compound was prepared in analogy to General Procedure 1 from 2-ethyl-10-methyl-6,7,8,9-tetrahydro-5H-[1,3]oxazolo[4,5-h][3]benzazepine (85 mg) and 5-{5-[(4-chlorobutyl)thio]-4-methyl-4H-1,2,4-triazol-3-yl}-2-methylquinoline (153 mg) and was obtained as a colourless slightly hygroscopic solid (136 mg).

(¹H-NMR CD₃OD): 8.35 (d, 1H); 8.23 (d, 1H); 8.00 (dd, 1H); 7.85 (d, 1H); 7.62 (d, 1H); 7.34 (s, 1H); 3.86 (m, 2H); 3.52 (s, 3H); 3.45 (m, 2H); 3.44 (m, 2H); 3.36 (m, 2H); 3.23 (m, 2H); 3.06 (m, 2H); 2.96 (q, 2H); 2.84 (s, 3H); 2.50 (s, 3H); 2.12-1.90 (m, 4H); 1.42 (t, 3H).
MS (m/z): 541 [MH]⁺.

EXAMPLE 48

10-methyl-7-(4-{[4-methyl-5-(2-methyl-5-quinolinyl)-4H-1,2,4-triazol-3-yl]thio}butyl)-2-(trifluoromethyl)-6,7,8,9-tetrahydro-5H-[1,3]oxazolo[4,5-h][3]benzazepine hydrochloride

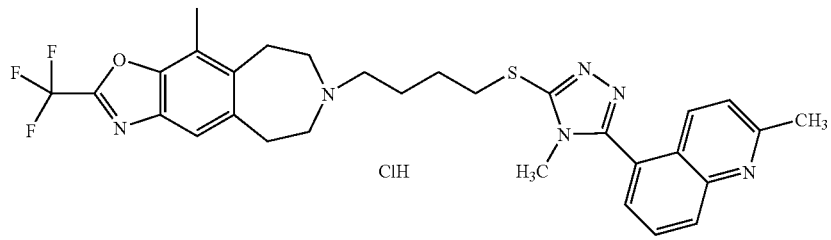

The title compound was prepared in analogy to General Procedure 1 from 10-methyl-2-(trifluoromethyl)-6,7,8,9-tetrahydro-5H-[1,3]oxazolo[4,5-h][3]benzazepine (120 mg) and 5-{5-[(4-chlorobutyl)thio]-4-methyl-4H-1,2,4-triazol-3-yl}-2-methylquinoline (224 mg) and was obtained according as a colourless slightly hygroscopic solid (163 mg).

(¹H-NMR, CD₃OD): 8.23 (d, 1H); 8.20 (d, 1H); 7.95 (dd, 1H); 7.79 (d, 1H); 7.62 (s, 1H); 7.56 (d, 1H); 3.88 (m, 2H); 3.62-3.44 (m, 2H); 3.51 (s, 3H); 3.42-3.30 (m, 6H); 3.10 (m, 2H); 2.78 (s, 3H); 2.57 (s, 3H); 2.13-1.90 (m, 4H). MS (m/z): 581 [MH]⁺.

EXAMPLE 49

2,10-dimethyl-7-(3-{[4-methyl-5-(2-methyl-5-quinolinyl)-4H-1,2,4-triazol-3-yl]thio}propyl)-6,7,8,9-tetrahydro-5H-[1,3]oxazolo[4,5-h][3]benzazepine hydrochloride

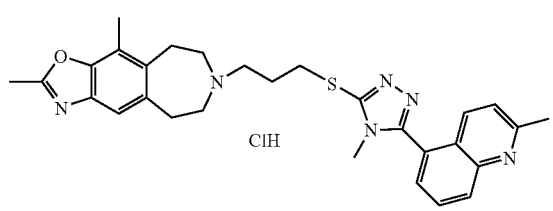

The title compound was prepared in analogy to General Procedure 1 from 2,10-dimethyl-6,7,8,9-tetrahydro-5H-[1,3]oxazolo[4,5-h][3]benzazepine (80 mg) and 5-{5-[(3-chloropropyl)thio]-4-methyl-4H-1,2,4-triazol-3-yl}-2-methylquinoline (147 mg) and was obtained as a colourless slightly hygroscopic solid (175 mg).

(¹H-NMR, CD₃OD): 8.79 (d, 1H); 8.34 (d, 1H); 8.18 (dd, 1H); 8.04 (d, 1H); 8.55 (d, 1H); 7.34 (s, 1H); 3.88 (m, 2H); 3.59 (s, 3H); 3.55-3.37 (m, 6H); 3.24 (m, 2H); 3.08 (m, 2H); 2.96 (s, 3H); 2.62 (s, 3H); 2.51 (s, 3H); 2.39 (m, 2H). MS (m/z): 513 [MH]⁺.

EXAMPLE 50

2-ethyl-10-methyl-7-(3-{[4-methyl-5-(2-methyl-5-quinolinyl)-4H-1,2,4-triazol-3-yl]thio}propyl)-6,7,8,9-tetrahydro-5H-[1,3]oxazolo[4,5-h][3]benzazepine hydrochloride

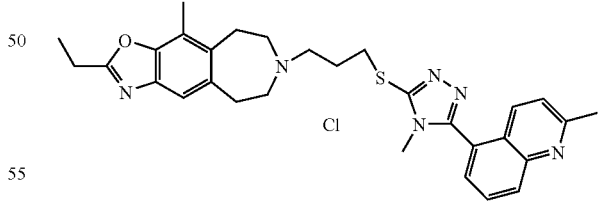

The title compound was prepared in analogy to General Procedure 1 from 2-ethyl-10-methyl-6,7,8,9-tetrahydro-5H-[1,3]oxazolo[4,5-h][3]benzazepine (85 mg) and 5-{5-[(3-chloropropyl)thio]-4-methyl-4H-1,2,4-triazol-3-yl}-2-methylquinoline (147 mg) and was obtained as a colourless slightly hygroscopic solid (150 mg).

(¹H-NMR, CD₃OD): 8.28 (d, 1H); 8.23 (d, 1H); 7.97 (dd, 1H); 7.82 (d, 1H); 7.59 (d, 1H); 7.36 (s, 1H); 3.88 (m, 2H);

3.52 (s, 3H); 3.51-3.37 (m, 6H); 3.23 (m, 2H); 3.09 (m, 2H); 2.97 (q, 2H); 2.80 (s, 3H); 2.51 (s, 3H); 2.38 (m, 2H); 1.41 (t, 3H). MS (m/z): 527 [MH]⁺.

EXAMPLE 51

10-Methyl-7-(3-{[4-methyl-5-(2-methyl-5-quinolinyl)-4H-1,2,4-triazol-3-yl]thio}propyl)-2-(trifluoromethyl)-6,7,8,9-tetrahydro-5H-[1,3]oxazolo[4,5-h][3]benzazepine hydrochloride

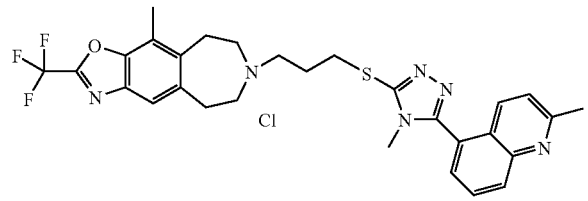

The title compound was prepared in analogy to General Procedure 1 from 10-methyl-2-(trifluoromethyl)-6,7,8,9-tetrahydro-5H-[1,3]oxazolo[4,5-h][3]benzazepine (120 mg) was reacted with 5-{5-[(3-chloropropyl)thio]-4-methyl-4H-1,2,4-triazol-3-yl}-2-methylquinoline (212 mg) and was obtained as a colourless slightly hygroscopic solid (115 mg).

(¹H-NMR, CD₃OD): 8.30 (d, 1H); 8.23 (d, 1H); 7.98 (dd, 1H); 7.83 (d, 1H); 7.64 (s, 1H); 7.60 (d, 1H); 3.91 (m, 2H); 3.63-3.32 (m, 8H); 3.52 (s, 3H); 3.12 (m, 2H); 2.81 (s, 3H); 2.58 (s, 3H); 2.39 (m, 2H). MS (m/z): 567 [MH]⁺.

EXAMPLE 52

10-bromo-7-(1-methyl-3-{[4-methyl-5-(2-methyl-5-quinolinyl)-4H-1,2,4-triazol-3-yl]thio}propyl)-2-(trifluoromethyl)-6,7,8,9-tetrahydro-5H-[1,3]oxazolo[4,5-h][3]benzazepine hydrochloride

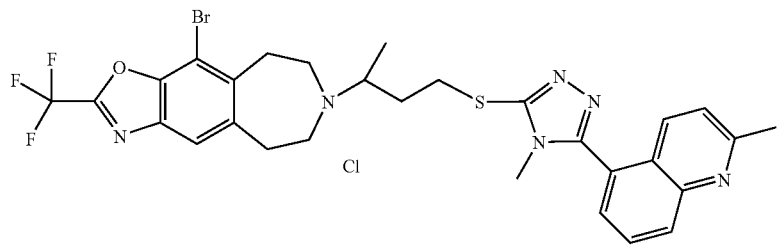

To a stirred solution of 3-{10-bromo-2-(trifluoromethyl)-6,7,8,9-tetrahydro-5H-[1,3]oxazolo[4,5-h][3]benzazepine}-butan-1-ol (218 mg) in chloroform (6 ml), thionyl chloride (0.078 ml) was added dropwise. After 2 hours additional thionyl chloride (2 eq) was added. After 1 hour the solvent was evaporated and the residue was triturated with a mixture of ethyl ether and petroleum ether (1/1) and decanted affording 10-bromo-(3-chloro-1-methyl-propyl)-2-(trifluoromethyl)-6,7,8,9-tetrahydro-5H-[1,3]oxazolo[4,5h][3]benzazepine hydrochloride as white solid (195 mg).

A mixture of 10-bromo-(3-chloro-1-methyl-propyl)-2-trifluoromethyl-6,7,8,9-tetrahydro-5H-[1,3]oxazolo[4,5h][3]benzazepine hydrochloride (195 mg), 4-methyl-5-(2-methyl-5-quinolinyl)-2,4-dihydro-3H-1,2,4-triazole-3-thione (130 mg), triethylamine (0.148 ml) and sodium iodide (63 mg) in dry DMF (0.8 ml) was heated at 70° C. for 24 hours. The mixture was cooled to room temperature, diluted with ethyl acetate and washed with 5% NaHCO₃. The organic phase was dried (Na₂SO₄) and concentrated. The residue was purified on silica gel (DCM/MeOH/NH₄OH: 100/1.5/0.15). The obtained product was treated with HCl (1N/ether) affording the title compound as a colourless slightly hygroscopic solid (46 mg).

(¹H-NMR, CD₃OD): 8.18 (d, 1H); 8.09 (d, 1H); 7.90 (dd, 1H); 7.74 (d, 1H); 7.62 (s, 1H); 7.49 (d, 1H); 3.47 (s, 3H); 3.43-3.26 (m, 4H); 3.16 (m, 2H); 3.00 (m, 1H); 2.82 (m, 2H); 2.75 (s, 3H); 2.64 (m, 2H); 2.03 (m, 1H); 1.80 (m, 1H); 0.98 (d, 3H). MS (m/z): 646 [MH]⁺.

EXAMPLE 53

10-bromo-2-ethyl-7-(1-methyl-3-{[4-methyl-5-(2-methyl-5-quinolinyl)-4H-1,2,4-triazol-3-yl]thio}propyl)-6,7,8,9-tetrahydro-5H-[1,3]oxazolo[4,5-h][3]benzazepine hydrochloride

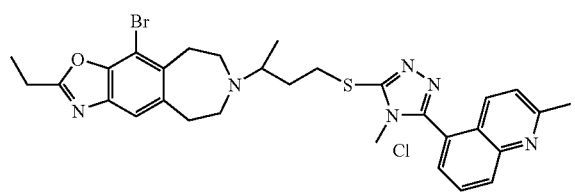

The title compound was synthesized in analogy to Example 52 from 3-{10-bromo-2-ethyl-6,7,8,9-tetrahydro-5H-[1,3]oxazolo[4,5-h][3]benzazepine}-butan-1-ol (211 mg) in 90 mg yield.

(¹H-NMR, CD₃OD): 8.29 (d, 1H); 8.22 (d, 1H); 7.96 (dd, 1H); 7.82 (d, 1H); 7.58 (d, 1H); 7.51 (s, 1H); 4.00-3.67 (m,

4H); 3.61-3.06 (m, 7H); 3.52 (s, 3H); 2.99 (q, 2H); 2.79 (s, 3H); 2.50 (m, 1H); 2.17 (m, 1H); 1.43 (d, 3H); 1.42 (t, 3H). MS (m/z): 606 [MH]+.

EXAMPLE 54

10-bromo-2-methyl-7-(1-methyl-3-{[4-methyl-5-(2-methyl-5-quinolinyl)-4H-1,2,4-triazol-3-yl]thio}propyl)-6,7,8,9-tetrahydro-5H-[1,3]oxazolo[4,5-h][3]benzazepine hydrochloride

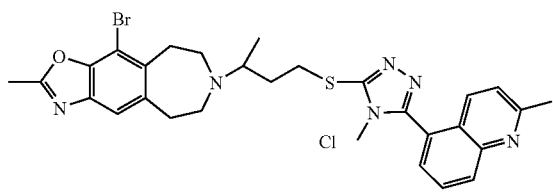

The title compound was synthesized in analogy to Example 52 from 3-{10-bromo-2-methyl-6,7,8,9-tetrahydro-5H-[1,3]oxazolo[4,5-h][3]benzazepine}-butan-1-ol (167 mg) in 60 mg yield.

($^1$H-NMR, CD$_3$OD): 8.46 (d, 1H); 8.26 (d, 1H); 8.03 (dd, 1H); 7.89 (d, 1H); 7.67 (d, 1H); 7.49 (s, 1H); 3.81 (m, 4H); 3.61-3.48 (m, 1H); 3.54 (s, 3H); 3.36 (m, 1H); 3.27-3.04 (m, 2H); 2.85 (s, 3H); 2.65 (s, 3H); 2.50 (m, 1H); 2.18 (m, 1H); 1.42 (d, 3H). MS (m/z): 592 [MH]+.

EXAMPLE 55

10-methyl-7-(1-methyl-3-{[4-methyl-5-(2-methyl-5-quinolinyl)-4H-1,2,4-triazol-3-yl]thio}propyl)-2-(trifluoromethyl)-6,7,8,9-tetrahydro-5H-[1,3]oxazolo[4,5-h][3]benzazepine hydrochloride

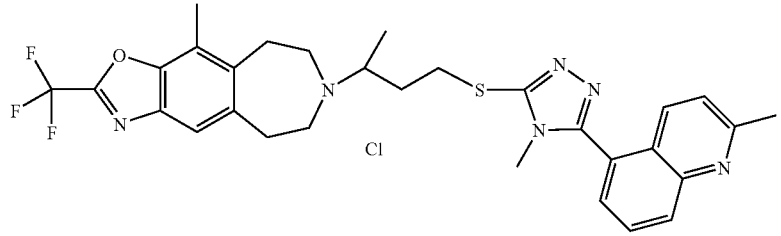

The title compound was synthesized in analogy to Example 52 from 3-{10-methyl-2-(trifluoromethyl)-6,7,8,9-tetrahydro-5H-[1,3]oxazolo[4,5-h][3]benzazepine}-butan-1-ol (253 mg) in 93 mg yield.

($^1$H-NMR, CDCl$_3$): 8.51 (d, 1H); 8.26 (d, 1H); 8.05 (dd, 1H); 7.91 (d, 1H); 7.69 (d, 1H); 7.63 (s, 1H); 3.81 (m, 3H); 3.61-3.03 (m, 8H); 3.55 (s, 3H); 2.87 (s, 3H); 2.58 (s, 3H); 2.51 (m, 1H); 2.19 (m, 1H); 1.43 (d, 3H). MS (m/z): 581 [MH]+.

EXAMPLE 56

2-(1-methylethyl)-7-(3-{[4-methyl-5-(2-methyl-5-quinolinyl)-4H-1,2,4-triazol-3-yl]thio}propyl)-3,5,6,7,8,9-hexahydroazepino[4,5-f]isoindol-1(2H)-one hydrochloride

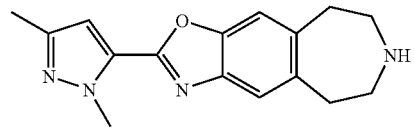

The title compound was prepared in analogy to General Procedure 1 from 2-(1-methylethyl)-3,5,6,7,8,9-hexahydroazepino[4,5-f]isoindol-1(2H)-one (80 mg) and 5-{5-[(3-chloropropyl)thio]-4-methyl-4H-1,2,4-triazol-3-yl}-2-methylquinoline (130 mg) and was obtained as a colourless slightly hygroscopic solid (120 mg).

($^1$H-NMR, CD$_3$OD): 8.20 (d, 1H); 8.17 (d, 1H); 7.92 (dd, 1H); 7.76 (d, 1H); 7.61 (s, 1H); 7.52 (d, 1H); 7.47 (s, 1H); 4.54 (m, 1H); 4.45 (s, 2H); 3.86 (m, 2H); 3.51 (s, 3H); 3.51-2.99 (m, 10H); 2.74 (s, 3H); 2.39 (m, 2H); 1.31 (d, 6H). MS (m/z): 541 [MH]+.

EXAMPLE 57

2-(1-methylethyl)-7-(4-{[4-methyl-5-(2-methyl-5-quinolinyl)-4H-1,2,4-triazol-3-yl]thio}butyl)-3,5,6,7,8,9-hexahydroazepino[4,5-f]isoindol-1(2H)-one hydrochloride

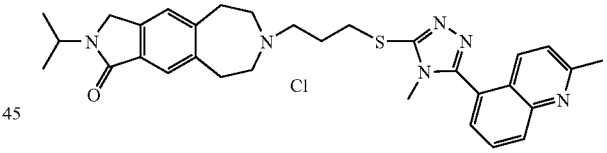

The title compound was prepared in analogy to General Procedure 1 from 2-(1-methylethyl)-3,5,6,7,8,9-hexahydroazepino[4,5-f]isoindol-1(2H)-one (80 mg) and 5-{5-[(4-chlorobutyl)thio]-4-methyl-4H-1,2,4-triazol-3-yl}-2-methylquinoline (135 mg) and was obtained as a colourless slightly hygroscopic solid (90 mg).

($^1$H-NMR, CD$_3$OD): 8.20 (d, 1H); 8.20 (d, 1H); 7.94 (dd, 1H); 7.80 (d, 1H); 7.60 (s, 1H); 7.54 (d, 1H); 7.46 (s, 1H); 4.54 (m, 1H); 4.44 (s, 2H); 3.85 (m, 2H); 3.57-3.32 (m, 6H); 3.50 (s, 3H); 3.23 (m, 2H); 3.10 (m, 2H); 2.78 (s, 3H); 2.13-1.89 (m, 4H); 1.30 (d, 6H). MS (m/z): 555 [MH]$^+$.

The invention claimed is:
1. A compound of formula (I) or a salt thereof:

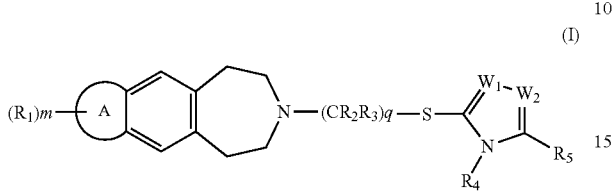

wherein
A is a 5 or 6 membered heteroaromatic ring or a 5 or 6 membered heterocyclic ring;
m is 0, 1, 2 or 3;
$R_1$ is independently halogen; oxo; hydroxy; cyano; nitro; $C_{1-4}$alkyl; halo$C_{1-4}$-alkyl; $C_{3-6}$cycloalkyl; $C_{1-4}$alkoxy; halo$C_{1-4}$alkoxy; $C_{1-4}$alkoxy$C_{1-4}$alkoxy; $C_{1-4}$alkylenedioxy; $C_{1-4}$alkylthio; $C_{1-4}$alkoxy$C_{1-4}$alkyl; $C_{3-6}$cycloalkyl$C_{1-4}$alkoxy; $C_{3-6}$cycloalkyl$C_{1-4}$alkyl; $C_{1-4}$alkanoyl; $C_{1-4}$alkoxycarbonyl; $C_{1-4}$alkoxycarbonyl$C_{1-4}$alkyl; $C_{1-4}$alkylsulfonyl; $C_{1-4}$alkylsulfonyloxy; halo$C_{1-4}$alkylsulfonyl; halo$C_{1-4}$alkylsulfonyloxy; $C_{1-4}$alkylsulfonyl$C_{1-4}$-alkyl; $C_{1-4}$alkylsulfonamido; $C_{1-4}$alkylsulfonamido$C_{1-4}$alkyl; heterocyclyl; aryl; aryl$C_{1-4}$alkoxy; aryloxy; arylthio; arylmethyl; aroyl; aryloxymethyl; arylsulfonyl; arylNR' wherein R' is hydrogen or $C_{1-4}$alkyl; arylsulfonyloxy; arylsulfonyl$C_{1-4}$alkyl; arylsulfonamido; arylcarboxamido; arylsulfonamido$C_{1-4}$alkyl; arylcarboxamido$C_{1-4}$alkyl; aroyl$C_{1-4}$alkyl; aryl$C_{1-4}$alkanoyl; or a group $R_6CON(R_7)(CH_2)_r$, $R_6R_7NCO(CH_2)_r$, $R_6R_7NSO_2(CH_2)_r$ in which each r is independently 0, 1, 2, 3 or 4, or —NR$_6$R$_7$; where each of the four preceding groups $R_6$ and $R_7$ are independently hydrogen or $C_{1-4}$alkyl; or in the groups NR$_6$R$_7$, R$_6$CON(R$_7$)(CH$_2$)$_r$, R$_6$R$_7$NCO(CH$_2$)$_r$ or R$_6$R$_7$NSO$_2$(CH$_2$)$_r$, R$_8$CONR$_7$ or NR$_6$R$_7$ together form a 4-, 5-, 6- or 7-membered azacyclic group may contain one additional O, N or S atom in the azacyclic group and having 3-8 carbon atoms including the carbon atoms contained in any optional substituent(s) of the azacyclic ring; wherein in any group containing an aryl moiety, the aryl moiety is unsubstituted or substituted by one, two or three substituents selected from the group consisting of halogen, hydroxy, cyano, nitro, amino, $C_{1-4}$alkyl, $C_{1-4}$alkoxy, halo$C_{1-4}$-alkoxy, $C_{1-4}$alkylenedioxy, $C_{1-4}$alkanoyl, $C_{1-4}$alkylsulfonyl, halo$C_{1-4}$alkylsulfonyl, $C_{1-4}$alkylamino, R$_8$R$_9$NCO in which R$_8$ and R$_9$ are independently hydrogen or $C_{1-4}$alkyl, or R$_8$R$_9$N together form a 4-, 5-, 6- or 7-membered azacyclic group which may contain one additional O, N or S atom in the azacyclic group and having 3-8 carbon atoms including the carbon atoms contained in any optional substituent(s) of the azacyclic group;
$R_2$ and $R_3$ are independently hydrogen or methyl;
q is 2, 3 or 4;
$W_1$ and $W_2$ are independently N, CH or —C($C_{1-4}$alkyl)-;
$R_4$ is hydrogen or $C_{1-4}$alkyl;
$R_5$ is a group of the formula (a) or (b):

—Z (a)

—(CR$_{10}$R$_{11}$)$_t$Z (b)

wherein
Z is $C_{1-4}$alkyl, halo$C_{1-4}$alkyl, $C_{3-8}$cycloalkyl, phenyl, heterocyclyl, a 5- or 6-membered heteroaromatic group or a 8- to 11-membered bicyclic group, any of which is unsubstituted or substituted by 1, 2, 3 or 4 substituents selected from the group consisting of: halogen, hydroxy, oxo, cyano, nitro, $C_{1-4}$alkyl, $C_{1-4}$alkoxy, halo$C_{1-4}$alkyl, halo$C_{1-4}$alkoxy, $C_{1-4}$alkylenedioxy, $C_{1-4}$alkanoyl, $C_{1-4}$alkylsulfonyl, $C_{1-4}$alkylsulfonyloxy, halo$C_{1-4}$-alkylsulfonyl, halo$C_{1-4}$alkylsulfonyloxy, $C_{1-4}$alkylsulfinyl, $C_{1-4}$alkylthio, R$_{12}$SO$_2$NR$_{13}$—, R$_{12}$R$_{13}$NSO$_2$—, R$_{12}$R$_{13}$NCO—, R$_{12}$CONR$_{13}$— and a 5- or 6-membered heteroaromatic group which is unsubstituted or substituted by one or two groups selected from the group consisting of $C_{1-2}$alkyl, halo$C_{1-2}$alkyl and R$_{12}$R$_{13}$N—; and wherein substituents positioned ortho to one another may be linked to form a 5- or 6-membered ring;
$R_{10}$ and $R_{11}$ are independently hydrogen or $C_{1-4}$alkyl and t is 1, 2, 3 or 4, or —(CR$_{10}$R$_{11}$)$_t$— forms a $C_{3-6}$cycloalkylene linker; and
$R_{12}$ and $R_{13}$ are independently hydrogen or $C_{1-4}$alkyl, or $R_{12}$ and $R_{13}$ together form $C_{3-6}$alkylene.

2. A compound or salt according to claim 1 wherein m is 0 or 1.

3. A compound or salt according to claim 1 wherein $R_1$ is halogen; oxo; cyano; $C_{1-4}$-alkyl; halo$C_{1-4}$alkyl; $C_{3-6}$cycloalkyl; $C_{1-4}$alkylsulfonyl; $C_{1-4}$alkylsulfonyloxy; R$_6$R$_7$NSO$_2$ where each of R$_6$ and R$_7$ is independently hydrogen or $C_{1-4}$alkyl; or R$_6$R$_7$N together form a 4-, 5-, 6- or 7-membered azacyclic group which may contain one additional O, N or S atom in the azacyclic group and having 3-8 carbon atoms; a heterocyclyl selected from pyrrolidinyl, imidazolidinyl, pyrazolidinyl, tetrahydrofuranyl, dioxolanyl, piperidinyl, piperazinyl, morpholinyl, thiomorpholinyl, tetrahydrothienyl, dioxanyl, tetrahydro-2H-pyranyl and dithianyl, oxazolinyl, isoaxazolinyl, imidazolinyl, pyrazolinyl, 1,2,3,6-tetrahydropyridyl and 3,6-dihydro-2H-pyranyl.

4. A compound or salt according to claim 3 wherein $R_2$ and $R_3$ are hydrogen at each occurrence.

5. A compound or salt according to claim 4 wherein q is 2 or 3.

6. A compound or salt according to claim 5 wherein $W_1$ and $W_2$ are both N.

7. A compound or salt according to claim 6 wherein $R_4$ is hydrogen or methyl.

8. A compound or salt according to claim 7 wherein $R_5$ is formula (a).

9. A compound or salt according to claim 1 which is:
2-methyl-7-(3-{[4-methyl-5-(2-methyl-5-quinolinyl)-4H-1,2,4-triazol-3-yl]thio}propyl)-6,7,8,9-tetrahydro-5H-[1,3]oxazolo[4,5-h][3]benzazepine;
7-(3-{[4-methyl-5-(2-methyl-5-quinolinyl)-4H-1,2,4-triazol-3-yl]thio}propyl)-6,7,8,9-tetrahydro-5H-[1,3]oxazolo[4,5-h][3]benzazepine;
2-(1-methylethyl)-7-(3-{[4-methyl-5-(4-methyl-1,3-oxazol-5-yl)-4H-1,2,4-triazol-3-yl]thio}propyl)-6,7,8,9-tetrahydro-5H-[1,3]oxazolo[4,5-h][3]benzazepine;
2-(1-methylethyl)-7-(3-{[4-methyl-5-(2-methyl-5-quinolinyl)-4H-1,2,4-triazol-3-yl]thio}propyl)-6,7,8,9-tetrahydro-5H-[1,3]oxazolo[4,5-h][3]benzazepine;

2-(1,1-dimethylethyl)-7-(3-{[4-methyl-5-(2-methyl-5-quinolinyl)-4H-1,2,4-triazol-3-yl]thio}propyl)-6,7,8,9-tetrahydro-5H-[1,3]oxazolo[4,5-h][3]benzazepine;

7-(3-{[4-methyl-5-(2-methyl-5-quinolinyl)-4H-1,2,4-triazol-3-yl]thio}propyl)-2-propyl-6,7,8,9-tetrahydro-5H-[1,3]oxazolo[4,5-h][3]benzazepine;

7-(3-{[4-methyl-5-(2-methyl-5-quinolinyl)-4H-1,2,4-triazol-3-yl]thio}propyl)-2-(2,2,2-trifluoroethyl)-6,7,8,9-tetrahydro-5H-[1,3]oxazolo[4,5-h][3]benzazepine;

7-(3-{[4-methyl-5-(2-methyl-5-quinolinyl)-4H-1,2,4-triazol-3-yl]thio}propyl)-2-(trifluoromethyl)-6,7,8,9-tetrahydro-5H-[1,3]oxazolo[4,5-h][3]benzazepine;

8-(3-{[4-methyl-5-(2-methyl-5-quinolinyl)-4H-1,2,4-triazol-3-yl]thio}propyl)-2,3,4,6,7,8,9,10-octahydro[1,4]oxazino[2,3-h][3]benzazepine;

4-methyl-8-(3-{[4-methyl-5-(2-methyl-5-quinolinyl)-4H-1,2,4-triazol-3-yl]thio}propyl)-4,6,7,8,9,10-hexahydro[1,4]oxazino[2,3-h][3]benzazepin-3(2H)-one;

4-methyl-8-(3-S-methyl-5-{[4-methyl-1,3-oxazol-5-yl)-4H-1,2,4-triazol-3-yl]thio}propyl)-4,6,7,8,9,10-hexahydro[1,4]oxazino[2,3-h][3]benzazepin-3(2H)-one;

2-(cyclopropylmethyl)-7-(3-{[4-methyl-5-(2-methyl-5-quinolinyl)-4H-1,2,4-triazol-3-yl]thio}propyl)-6,7,8,9-tetrahydro-5-H-[1,3]oxazolo[4,5-h][3]benzazepine;

2-(cyclopropylmethyl)-7-(3-{[4-methyl-5-(4-methyl-1,3-oxazol-5-yl)-4H-1,2,4-triazol-3-yl]thio}propyl)-6,7,8,9-tetrahydro-5H-[1,3]oxazolo[4,5-h][3]benzazepine;

2-ethyl-7-(3-{[4-methyl-5-(4-methyl-1,3-oxazol-5-yl)-4H-1,2,4-triazol-3-yl]thio}propyl)-6,7,8,9-tetrahydro-5H-[1,3]oxazolo[4,5-h][3]benzazepine;

2-ethyl-7-(3-{[4-methyl-5-(2-methyl-5-quinolinyl)-4H-1,2,4-triazol-3-yl]thio}propyl)-6,7,8,9-tetrahydro-5H-[1,3]oxazolo[4,5-h][3]benzazepine;

3-methyl-7-(3-{[4-methyl-5-(2-methyl-5-quinolinyl)-4H-1,2,4-triazol-3-yl]thio}propyl)-6,7,8,9-tetrahydro-5H-isoxazolo[4,5-h][3]benzazepine;

3-methyl-7-(3-{[4-methyl-5-(4-methyl-1,3-oxazol-5-yl)-4H-1,2,4-triazol-3-yl]thio}propyl)-6,7,8,9-tetrahydro-5H-isoxazolo[4,5-h][3]benzazepine;

2-cyclopropyl-7-(3-{[4-methyl-5-(2-methyl-5-quinolinyl)-4H-1,2,4-triazol-3-yl]thio}propyl)-6,7,8,9-tetrahydro-5H[1,3]oxazolo[4,5-h][3]benzazepine;

2-methyl-7-(2-{[4-methyl-5-(2-methylquinolin-5-yl)-4H-1,2,4-triazol-3-yl]thio}ethyl)-6,7,8,9-tetrahydro-5H-[1,3]oxazolo[4,5-h][3]benzazepine;

2-methyl-7-(3-{[4-methyl-5-(3-pyridinyl)-4H-1,2,4-triazol-3-yl]thio}propyl)-6,7,8,9-tetrahydro-5H-[1,3]oxazolo[4,5-h][3]benzazepine;

2-methyl-7-(3-{[4-methyl-5-[4-(trifluoromethyl)phenyl]-4H-1,2,4-triazol-3-yl}thio)propyl]-6,7,8,9-tetrahydro-5H-[1,3]oxazolo[4,5-h][3]benzazepine;

7-(3-{[5-(3,4-Difluorophenyl)-4-methyl-4H-1,2,4-triazol-3-yl]thio}propyl)-2-methyl-6,7,8,9-tetrahydro-5H-[1,3]oxazolo[4,5-h][3]benzazepine;

2-methyl-7-(3-{[4-methyl-5-(tetrahydro-2H-pyran-4-yl)-4H-1,2,4-triazol-3-yl]thio}propyl)-6,7,8,9-tetrahydro-5H-[1,3]oxazolo[4,5-h][3]benzazepine;

2-ethyl-7-(3-{[4-methyl-5-(3-pyridinyl)-4H-1,2,4-triazol-3-yl]thio}propyl)-6,7,8,9-tetrahydro-5H-[1,3]oxazolo[4,5-h][3]benzazepine;

2-ethyl-7-(3-{[4-methyl-5,4-(trifluoromethyl)phenyl]-4H-1,2,4-triazol-3-yl}thio)propyl]-6,7,8,9-tetrahydro-5H-[1,3]oxazolo[4,5-h][3]benzazepine; or 7-(3-O-(3,4-difluorophenyl)-4-methyl-4H-1,2,4-triazol-3-yl]thio}propyl)-2-ethyl-6,7,8,9-tetrahydro-5H-[1,3]oxazolo[4,5-h][3]benzazepine;

or a salt thereof.

10. A pharmaceutical composition comprising a compound or salt of formula (I) according to claim 1 and a pharmaceutically acceptable excipient.

11. A method for treating schizophrenia, schizo-affective disorders, psychotic depression, mania, paranoid or delusional disorders in a human, the method comprising administering a therapeutically effective amount of a compound of formula (I) according to claim 1, or a salt thereof, neat or as a pharmaceutically acceptable composition, to a patient in need thereof.

* * * * *